(12) United States Patent
Tran

(10) Patent No.: US 11,298,063 B2
(45) Date of Patent: Apr. 12, 2022

(54) HYDROGEN POWERED DEVICE

(71) Applicant: Bao Q Tran, Saratoga, CA (US)

(72) Inventor: Bao Q Tran, Saratoga, CA (US)

( * ) Notice: Subject to any disclaimer, the term of this patent is extended or adjusted under 35 U.S.C. 154(b) by 338 days.

(21) Appl. No.: 16/658,148

(22) Filed: Oct. 20, 2019

(65) Prior Publication Data

US 2021/0113130 A1 Apr. 22, 2021

(51) Int. Cl.

| | | |
|---|---|---|
| *A61B 5/20* | (2006.01) | |
| *A61B 5/145* | (2006.01) | |
| *A61B 5/0205* | (2006.01) | |
| *A61B 5/01* | (2006.01) | |
| *A61B 5/11* | (2006.01) | |
| *A61B 5/00* | (2006.01) | |
| *A61B 5/103* | (2006.01) | |
| *A61F 13/84* | (2006.01) | |
| *A61F 5/453* | (2006.01) | |
| *A61F 5/44* | (2006.01) | |
| *A61F 5/455* | (2006.01) | |
| *H01M 8/065* | (2016.01) | |
| *A61B 5/024* | (2006.01) | |
| *A61B 5/08* | (2006.01) | |
| *A61B 5/021* | (2006.01) | |

(52) U.S. Cl.
CPC ............ *A61B 5/201* (2013.01); *A61B 5/0077* (2013.01); *A61B 5/01* (2013.01); *A61B 5/02055* (2013.01); *A61B 5/1032* (2013.01); *A61B 5/1118* (2013.01); *A61B 5/14532* (2013.01); *A61B 5/14546* (2013.01); *A61B 5/6808* (2013.01); *A61F 5/4404* (2013.01); *A61F 5/453* (2013.01); *A61F 5/4556* (2013.01); *A61F 13/8405* (2013.01); *H01M 8/065* (2013.01); *A61B 5/021* (2013.01); *A61B 5/024* (2013.01); *A61B 5/0816* (2013.01); *A61F 2013/8479* (2013.01); *A61F 2013/8494* (2013.01)

(58) Field of Classification Search
None
See application file for complete search history.

(56) References Cited

U.S. PATENT DOCUMENTS

| | | | |
|---|---|---|---|
| 3,353,539 A * | 11/1967 | Preston | ..................... A61F 2/00 607/2 |
| 5,695,947 A | 12/1997 | Guo | |
| 5,876,952 A | 3/1999 | Shieh | |
| 5,893,176 A | 4/1999 | Magiera | |
| 6,706,027 B2 | 2/2004 | Harvie | |
| 7,018,366 B2 | 3/2006 | Easter | |
| 7,097,813 B2 * | 8/2006 | Ord | ....................... H01M 8/065 422/129 |

(Continued)

OTHER PUBLICATIONS

Sutrisno, Noninvasive and Painless Urine Glucose Detection by Using Computer-based Polarimeter, IOP Conf. Series Materials Science and Engineering 202 (2017) 012030 doi:10.1088/1757-899X/202/1/012030.

(Continued)

*Primary Examiner* — Carl H Layno
*Assistant Examiner* — Manolis Pahakis
(74) *Attorney, Agent, or Firm* — Patent PC; Bao Tran

(57) ABSTRACT

A system and method to handle urine includes collecting urine using a pad or garment, exposing the urine to an aluminum alloy to generate hydrogen gas and heat in an exothermic reaction, and storing the hydrogen in a sealed chamber.

19 Claims, 9 Drawing Sheets

(56) References Cited

U.S. PATENT DOCUMENTS

| | | | |
|---|---|---|---|
| 8,895,204 B2 | 11/2014 | Wallace | |
| 9,029,028 B2 | 5/2015 | Eickhoff | |
| 9,345,361 B2 | 5/2016 | Pollock | |
| 9,492,333 B2* | 11/2016 | Uda | A61F 13/539 |
| 9,502,730 B2* | 11/2016 | Wang | H01M 8/0239 |
| 9,587,915 B2 | 3/2017 | Hagen | |
| 10,383,606 B1 | 8/2019 | Mccord | |
| 10,932,503 B2* | 3/2021 | Fallis | H02J 7/022 |
| 2003/0044656 A1* | 3/2003 | Wood | C01B 3/065 |
| | | | 429/421 |
| 2004/0161646 A1* | 8/2004 | Rezachek | C01B 3/065 |
| | | | 429/421 |
| 2005/0231855 A1* | 10/2005 | Tran | G11C 11/21 |
| | | | 360/324.1 |
| 2007/0237994 A1* | 10/2007 | Nakai | H01M 8/04216 |
| | | | 429/421 |
| 2008/0091089 A1* | 4/2008 | Guillory | A61B 5/4094 |
| | | | 600/301 |
| 2008/0202174 A1* | 8/2008 | Fabbro | D06F 39/006 |
| | | | 68/212 |
| 2010/0099010 A1* | 4/2010 | Niessen | H01M 6/34 |
| | | | 429/506 |
| 2012/0244765 A1* | 9/2012 | Huang | H01M 8/065 |
| | | | 441/89 |
| 2013/0321168 A1* | 12/2013 | Mahony | A61B 5/318 |
| | | | 340/870.09 |
| 2014/0235965 A1 | 8/2014 | Tran | |
| 2014/0275923 A1* | 9/2014 | Haffner | A61B 5/6867 |
| | | | 600/377 |
| 2015/0126834 A1* | 5/2015 | Wang | B32B 38/145 |
| | | | 600/345 |
| 2015/0351690 A1* | 12/2015 | Toth | A61B 5/296 |
| | | | 600/373 |
| 2016/0045841 A1* | 2/2016 | Kaplan | B01D 53/48 |
| | | | 429/49 |
| 2016/0106577 A1* | 4/2016 | Moreshead | A61F 13/0233 |
| | | | 607/96 |
| 2016/0338626 A1* | 11/2016 | Wang | A61B 5/14507 |
| 2017/0086714 A1* | 3/2017 | Nothacker | A61B 5/4023 |
| 2017/0214076 A1* | 7/2017 | Dhawan | H02J 1/00 |
| 2017/0325724 A1* | 11/2017 | Wang | A61B 5/14521 |
| 2018/0199873 A1* | 7/2018 | Wang | C12Q 1/54 |
| 2018/0219267 A1 | 8/2018 | Martin | |
| 2018/0233761 A1* | 8/2018 | Slaughter | H01M 8/16 |
| 2019/0024216 A1* | 1/2019 | Giri | C01B 3/08 |
| 2019/0104936 A1* | 4/2019 | Gunn | A61B 3/0025 |
| 2019/0117083 A1* | 4/2019 | Wang | A61B 5/0205 |
| 2019/0239786 A1* | 8/2019 | Burnett | H01M 8/065 |
| | | | 422/129 |
| 2019/0247050 A1* | 8/2019 | Goldsmith | A61B 17/00491 |
| 2019/0341637 A1* | 11/2019 | Fine | C01B 3/08 |
| 2020/0309753 A1* | 10/2020 | Mamerow | G01N 30/04 |
| 2020/0353239 A1* | 11/2020 | Daniels | A61B 5/296 |
| 2021/0113130 A1* | 4/2021 | Tran | A61B 5/201 |

OTHER PUBLICATIONS

Martinez, Can Photoplethysmography Replace Arterial Blood Pressure in the Assessment of Blood Pressure?J. Clin. Med. 2018, 7, 316; doi:10.3390/jcm7100316.

* cited by examiner

FIG. 1I

| |
|---|
| Generate a blood pressure model of a patient (2002); |
| Determine a heart rate and/or blood flow velocity using an optical PPG transducer near a blood vessel (2004); |
| Provide the heart rate and/or blood flow velocity to the blood pressure model to continuously estimate blood pressure (2006) |

FIG. 1J

| |
|---|
| During an initialization mode, a monitoring device and calibration device are attached to patient (2010) |
| The monitoring device generates patient heart rate and/or blood flow velocity using PPG sensors, while actual blood pressure is measured by a gold standard calibration device (2012) |
| System generates a blood pressure model based on the heart rate or blood flow velocity and the actual blood pressure (2014) |
| The calibration device can be removed (2016) |
| During an operation mode, the process periodically samples heart rate or blood flow velocity from the monitoring device on a real-time basis (2018) and provides the heart rate or blood flow velocity as input information to the blood pressure model to estimate blood pressure (2020) |

FIG. 2A

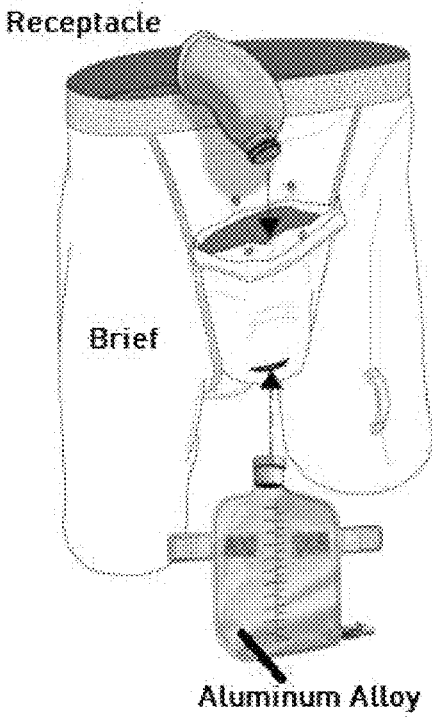

FIG. 2B

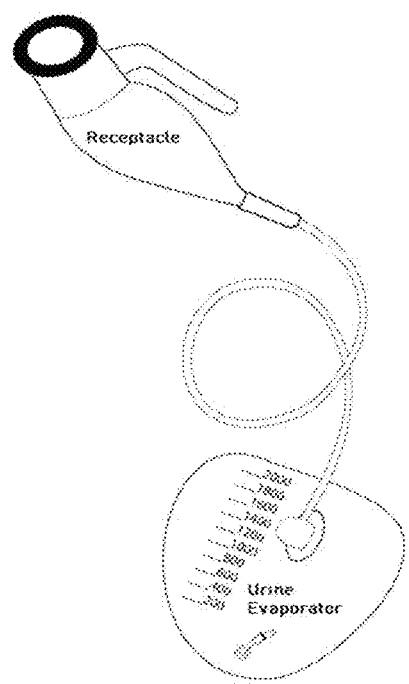

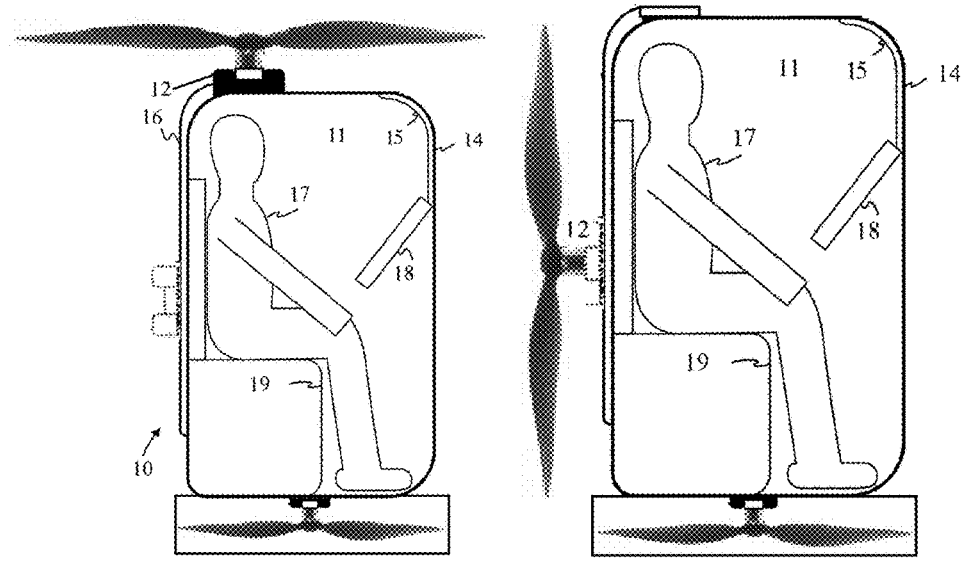

| |
|---|
| Upload a flight plan to the flight control system of the vehicle and get authorization (21) |
| Lift vehicle into the air in a vertical takeoff and landing mode (22) |
| Transition the vehicle from the vertical takeoff and landing mode to a forward flight mode (23) |
| Transport the vehicle to the desired destination location (24) |
| Transition vehicle from the forward flight mode to the vertical takeoff and landing mode (25) |
| Land vehicle at destination (26) |

FIG. 5D

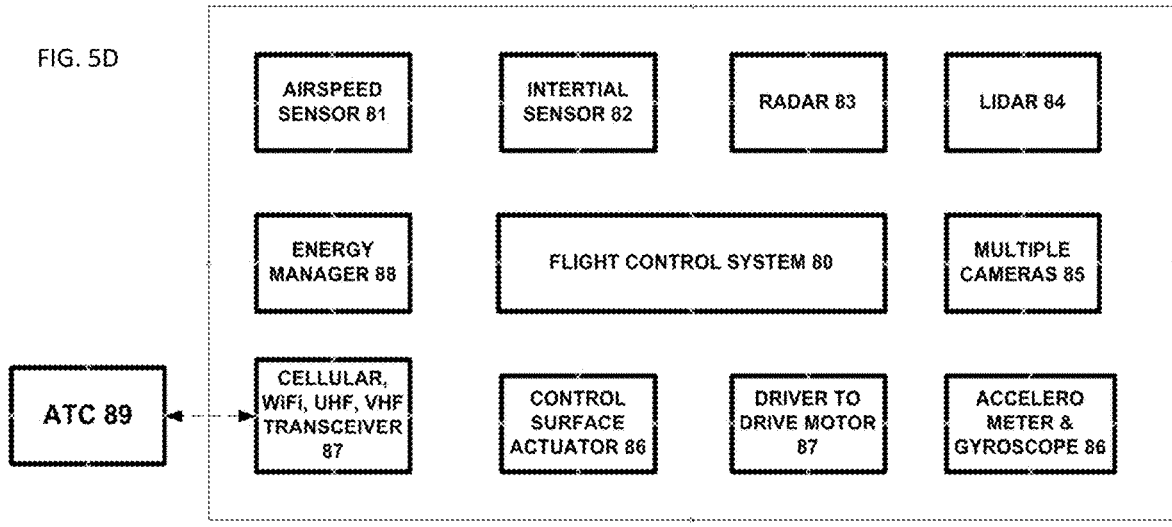

HYDROGEN POWERED DEVICE

BACKGROUND

Urinary incontinence affects more than 13 million Americans in community and institutional settings. Thirty-eight percent of non-institutionalized patients older than 60 years of age experienced urinary incontinence, and almost 50 percent of institutionalized patients. The annual costs of bladder control problems in the United States for people older than 65 years of age was estimated at $26.3 billion in 1995, or $3,565 per affected person. Many incontinent males use commercially available diapers, which cannot contain urine from multiple urinations, and become heavy and uncomfortable when wet.

The problem also shows up for athletes, astronauts, pilots, and others who are restricted from using a normal bathroom. One option is to pee in place, but the pilot suffers from skin exposure to urine for extended durations. To avoid this inconvenience, pilots often practice "tactical dehydration" by purposing not drinking water before a flight, but this practice can reduce one's situational awareness and decision-making abilities during long-duration operations. It can also affect a pilot's ability to withstand high G-forces, which can be fatal for fighter pilots in combat and thus good bladder relief device is important not just for the aircrew member's comfort, health and safety, but also for the safety of the aircraft and squadron.

Male aircrew members flying extended flight operations can use two types of bladder relief devices, "piddle pack" bag systems and uncomfortable external catheters with tubing. The entire procedure for using the piddle pack takes several minutes. During this procedure the pilot is distracted from flying the aircraft, which can place both himself and his aircraft in danger. The piddle pack bag system can also be dangerous to use if the pilot needs to eject from the aircraft while urinating. Similarly, there is also no acceptable bladder relief system for female aircrew members flying extended flight operations in aircraft that do not have toilet facilities. Male aircrew members use two types of bladder relief devices, piddle pack bag systems and external catheters with tubing.

Female aircrew members cannot use the catheter/tubing assemblies designed for males. Instead, most use commercially available adult diapers. These diapers have the following drawbacks:

1 Neither the Disposable Absorption Containment Device (DACD) developed by NASA nor commercially available diapers have the capacity to hold the 1000 cc of urine produced during some long duration flights.

2 High g maneuvers force the female aircrew member downward into the seat, displacing urine from the diaper and leaving the female to sit in a wet flight suit and seat for the duration of the flight.

3 Prolonged exposure to urine can cause skin irritation and may develop into more serious conditions such as ulcers.

The unsatisfactory urine collection options available, especially for female aviators, has created a culture of intentional dehydration prior to and during flight to avoid discomfort and risk of infection.

SUMMARY

In one aspect, a bladder relief system includes a urine receptacle; a sealed chamber with an alloy therein to generate hydrogen from a liquid; and a pump coupled to the urine receptacle and the sealed chamber to expose the urine to the alloy to generate hydrogen gas in the sealed chamber. In a corresponding method, urine is handled by collecting urine using a pad or garment; exposing the urine to an aluminum alloy to generate hydrogen gas and heat in an exothermic reaction; and storing the hydrogen in a sealed chamber.

In another aspect, a bladder relief system includes a urine receptacle; a sealed chamber with an alloy therein to generate hydrogen gas from a liquid; a pump coupled to the urine receptacle and the sealed chamber to expose the urine to the alloy to generate hydrogen gas in the sealed chamber; and a fuel cell coupled to the sealed chamber to generate electricity from the hydrogen.

In a further aspect, a bladder relief system for a wearer includes an inflatable underwear garment with an inner portion; a plurality of one way valves to move urine away from a skin of the wearer toward the inner portion; a sealed chamber with an alloy to generate hydrogen gas when the alloy is exposed to a liquid; a pump to transfer urine from the inner portion to the sealed chamber; and a fuel cell coupled to the sealed chamber to generate electricity from the hydrogen.

In another aspect, a bladder relief system for a wearer includes an inflatable underwear garment with an inner portion; a plurality of one-way valves to move urine away from a skin of the wearer toward the inner portion; a sealed chamber with an alloy to generate hydrogen gas when the alloy is exposed to a liquid; and a pump to transfer urine from the inner portion to the sealed chamber.

In another aspect, a water powered system includes an aluminum alloy source to expose a liquid to an aluminum alloy to generate hydrogen gas; a hydrogen tank to store the hydrogen gas; a fuel cell stack to receive hydrogen gas from the hydrogen gas tank and oxygen from the atmosphere, the fuel cell stack generating electricity; and an energy storage device to receive electricity.

Advantages of the vehicle may include one or more of the following. The system offers high performance in terms of emission rate, performance, fuel efficiency, durability, size, weight, cost, safety, and comfort. The relief system is easy to use and helps users to relax and use the device, as urination begins from a relaxation process not contraction process. The system provides wide social acceptance whether it be for an astronaut, wheelchair victim, emergency vehicle driver, long distance cyclist, triathlete, glider pilot, recreational pilot, bed-ridden patient, incontinence, or someone with other bladder problems. For pilots, the system handles leakage in adverse aircraft orientation and also address the issues of fit and comfort. The system supports a full-dress hands-free operation, and is easy to put on, comfortable to wear, and easy to remove. The system can be comfortably worn by pilots and passengers of both genders (as well as hospital patients, the incontinent, and animals) while removing urine away from the body without irritating the skin or creating discomfort. The system reduces the pilot's distraction or downtime during bladder relief, which improves pilot and aircraft safety.

BRIEF DESCRIPTION OF THE DRAWINGS

FIG. 1H shows an illustrative urine powered medical test system in a garment, while FIGS. 1I-1J show exemplary PPG based blood pressure sensor in FIG. 1H;

FIGS. 2A-2C show exemplary urine capture systems for power generation;

FIGS. 5A-5D show exemplary flying vehicles that use the water power generator.

DESCRIPTION

Figure 1A:
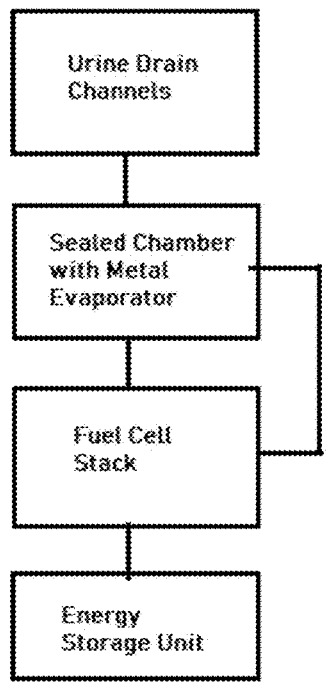
FIGS. 1A-1G show exemplary urine handling systems with undergarments and various sensor configurations in the undergarments.

FIG. 1A shows an exemplary a bladder relief system with a urine receptacle; a sealed and thermally insulated chamber with an alloy therein to generate hydrogen gas from a liquid; a pump coupled to the urine receptacle and the sealed chamber to expose the urine to the alloy to generate hydrogen gas in the sealed chamber; and a fuel cell coupled to the sealed chamber to generate electricity from the hydrogen. The fuel cell and energy store/battery is optional for portable embodiments such as diapers that need to be thin and does not need to generate electricity. Water generated by the fuel cell is fed back into the chamber to generate more electricity if needed.

For urine evaporation one embodiment uses a nanogalvanic structured aluminum-based particulate material that can convert urine into hydrogen very rapidly by hydrolysis reaction at room temperature without chemicals, catalysts, or externally supplied power. The method applies urine to the particulate material with aluminum, an aluminum alloy or another aluminum-based composition with a second metal, second alloy or other second metal-based composition. The allow is made by applying a milling machine to the aluminum, aluminum alloy or other aluminum-based composition and a second metal, alloy or other metal-based composition to produce a powder with grains or subgrains of aluminum with individual grains or subgrains of the dispersed second metal, second alloy or other second metal-based composition having atomic to nano-scale or micro-scale dimensions. In one embodiment, heat generated by the liquid to hydrogen process (exothermic) is captured and circulated in the diaper by a fan that drives air through heated air channels after suitable temperature regulation.

For the optional fuel cell, a fuel cell works much like an electric battery, converting chemical energy into electrical energy using the movement of charged hydrogen ions across an electrolyte membrane to generate current. There they recombine with oxygen to produce water—a fuel cell's only emission, alongside hot air. One type is Proton-exchange membrane fuel cells, also known as polymer electrolyte membrane (PEM) fuel cells (PEMFC). PEMFCs are built out of membrane electrode assemblies (MEA) which include the electrodes, electrolyte, catalyst, and gas diffusion layers. An ink of catalyst, carbon, and electrode are sprayed or painted onto the solid electrolyte and carbon paper is hot pressed on either side to protect the inside of the cell and also act as electrodes. The pivotal part of the cell is the triple phase boundary (TPB) where the electrolyte, catalyst, and reactants mix and thus where the cell reactions actually occur. Importantly, the membrane must not be electrically conductive so the half reactions do not mix. The energy storage can be a supercapacitor or a lithium battery, for example.

Figure 1B:
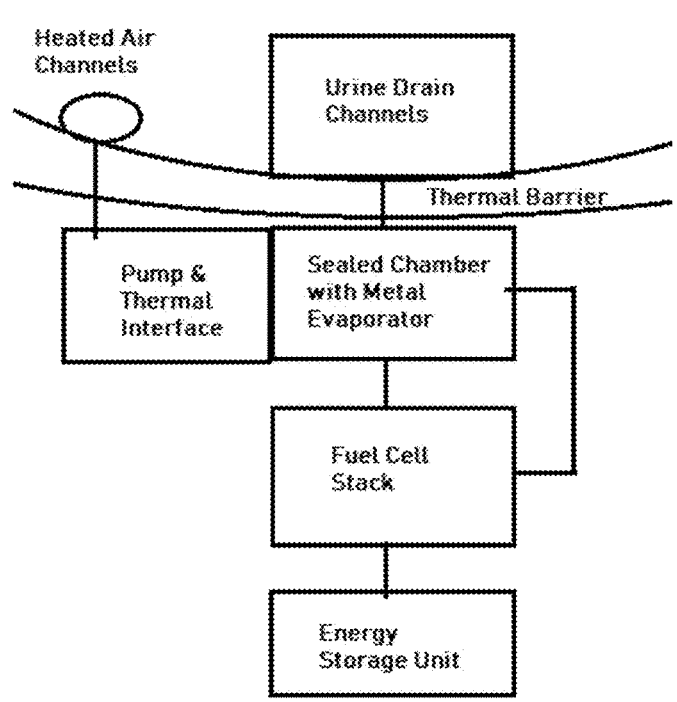

FIG. 1B shows an exemplary diaper embodiment with a plurality of air channels interdigitated with a plurality of urine drain channels. In this embodiment, liquid is removed by gravity or a pump and drained into the sealed and thermally insulated chamber with the urine evaporator containing a metallic compound to convert liquid into hydrogen gas. Heat generated during the exothermic reaction is used to dry the garment using a pump or a fan (FIG. 1F), for example.

Figure 1C:
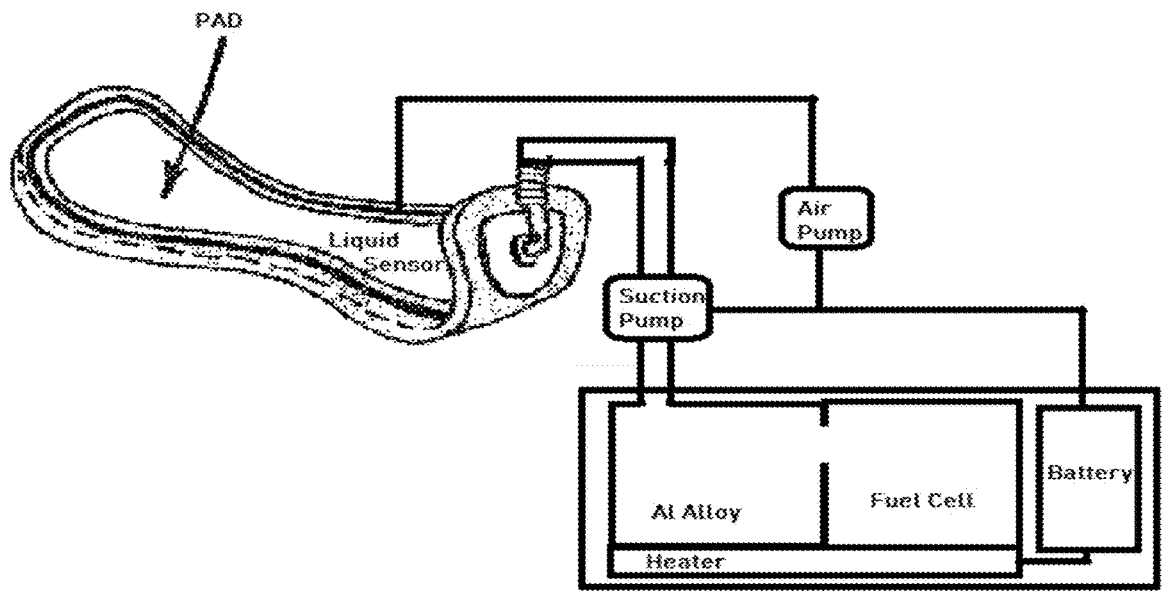

FIG. 1C shows an exemplary female pad receptacle that has an inflatable rim to provide space to receive urine when a female sits (such as in a flight seat). Urine drains down the receptacle via one way drains and pumped to a sealed ad thermally insulated chamber containing the aluminum compound to generate hydrogen, which is then provided to a fuel cell to generate electricity and water. The electricity is used to charge a battery, while the water can be fed back to the sealed chamber to generate more hydrogen.

In one implementation, a bladder relief system includes a urine receptacle; a sealed chamber with an alloy therein to generate hydrogen from a liquid; and a pump coupled to the urine receptacle and the sealed chamber to expose the urine to the alloy to generate hydrogen gas in the sealed chamber.

In a further implementation, a bladder relief system for a wearer includes an inflatable underwear garment with an inner portion; a plurality of one way valves to move urine away from a skin of the wearer toward the inner portion; a sealed chamber with an alloy to generate hydrogen gas when the alloy is exposed to a liquid; a pump to transfer urine from the inner portion to the sealed chamber; and a fuel cell coupled to the sealed chamber to generate electricity from the hydrogen.

In another implementation, a bladder relief system for a wearer includes an inflatable underwear garment with an inner portion; a plurality of one-way valves to move urine away from a skin of the wearer toward the inner portion; a sealed chamber with an alloy to generate hydrogen gas when the alloy is exposed to a liquid; and a pump to transfer urine from the inner portion to the sealed chamber.

In another implementation, a water powered system includes an aluminum alloy source to expose a liquid to an aluminum alloy to generate hydrogen gas; a hydrogen tank to store the hydrogen gas; a fuel cell stack to receive hydrogen gas from the hydrogen gas tank and oxygen from the atmosphere, the fuel cell stack generating electricity; and an energy storage device to receive electricity.

In yet another implementation, a bladder relief system includes a urine receptacle; a sealed chamber with an alloy therein to generate hydrogen from a liquid; and a pump coupled to the urine receptacle and the sealed chamber to expose the urine to the alloy to generate hydrogen gas in the sealed chamber.

In another implementation, a water powered system includes a sealed and insulated chamber with an aluminum alloy source; a control unit to selectively expose a predetermined amount of an aluminum alloy to to liquid to generate hydrogen gas; a fuel cell stack to receive hydrogen gas from the hydrogen gas tank and oxygen from the atmosphere, the fuel cell stack generating electricity; and an energy storage device to receive electricity. The control unit can be a motorized dispenser of pellets of the metal alloy that are then exposed to the urine, and the amount dispensed can be increased or decreased based on the temperature and gas generated to meet safety considerations. Alternatively, the user can manually dispense the alloy using a twist knob or push button that moves an actuator to deliver the pellet/grains of the metal alloy to contact the urine.

Figure 1D:
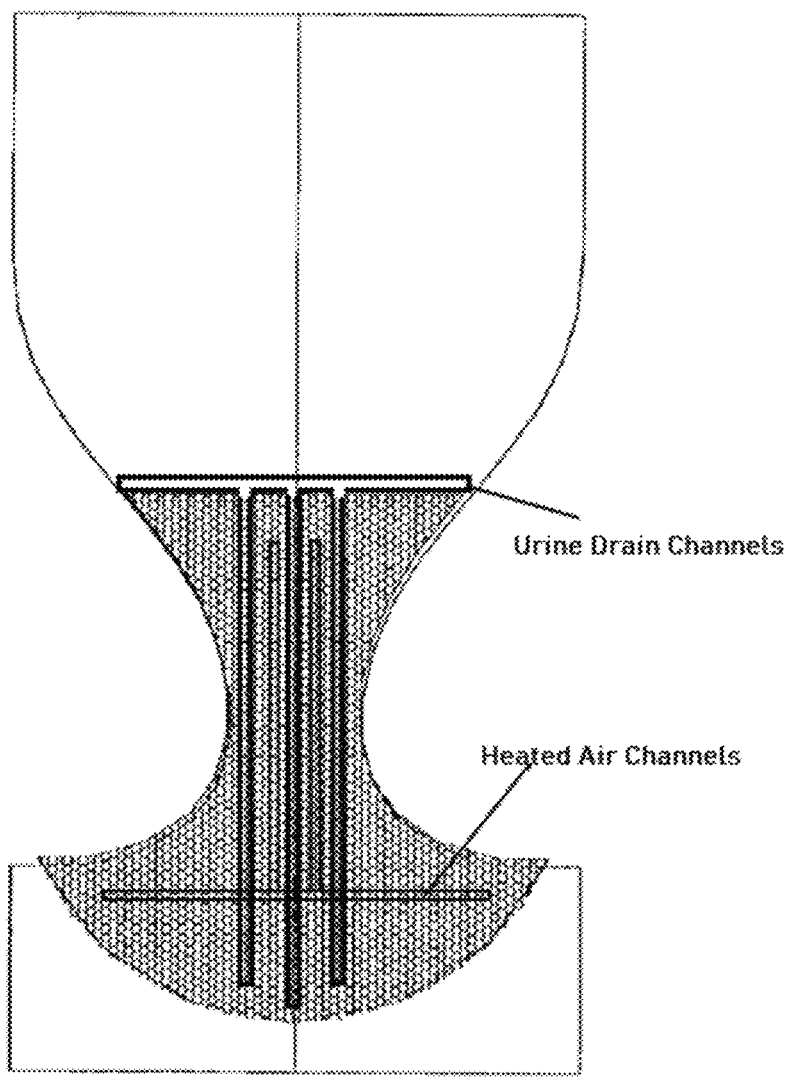

FIG. 1D shows an exemplary plan view of a pad/garment that can be used as washable underwear. The pad is shaped to wrap around the legs, and this shape is for illustration only. Numerous other diaper layout shapes can be used. In this plan view, two piping units are used, one for liquid capture, and one for heated air to dry the garment and provide comfort to the user. Each piping unit has an inlet manifold with a number of channels and inlet holes coupled together with a collector tube or channels. Due to the narrow region in the center, some of channels might not be routed directly through the center. Thus, a slightly larger collector tube or channel may be used at the extremities to act as a collector manifold to provide access to all regions and provide better surface coverage of the center area. The air piping unit is interdigitated with the urine piping unit in one embodiment. Flexible rubber tubes can be used for low volume production, and alternatively the channels can embedded or directly formed during manufacturing of the pad for high volume production. In another embodiment, one piping unit can alternatively be used for urine capture and for dispensing heated air to dry the garment.

Figure 1E:
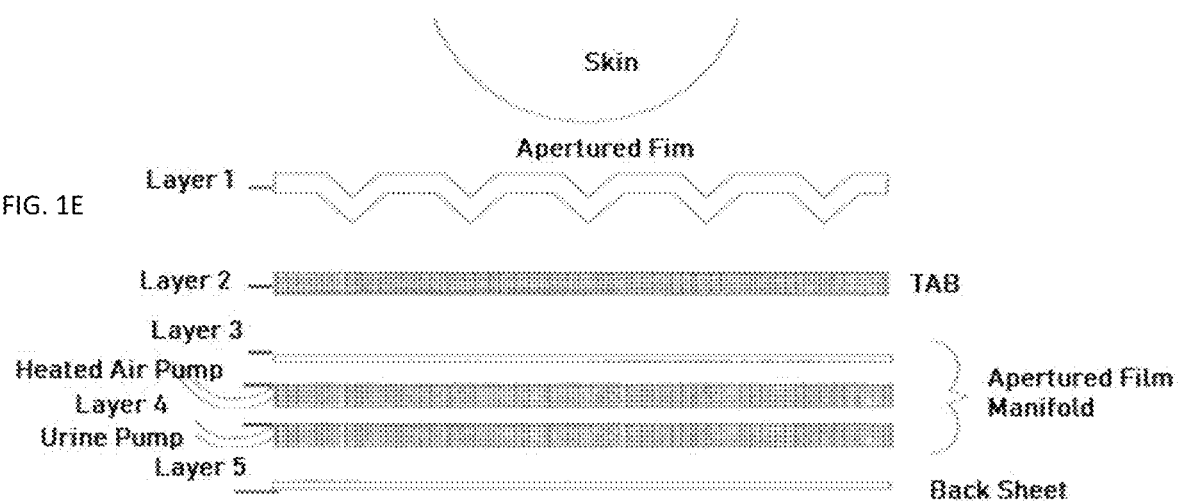
Figure 1F:
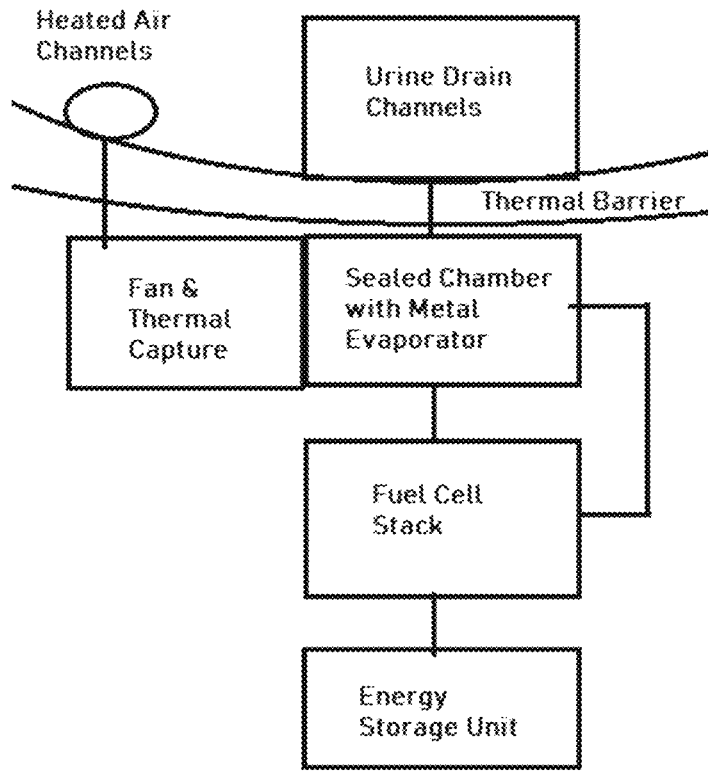

FIG. 1E is a cross-section view of the garment of the first embodiment of the present invention. The garment may have multiple layers of material with the manifold imbedded in between these layers. The production process may be similar to diaper production. The method of production may need to be modified slightly in order to imbed the manifold in the garment. For example, the manifold may be held and released from a production drum with a timed vacuum source.

Fabric selection will be made after consulting with experts in the undergarment fabric industry. Skin may come in contact with first layer. First layer may be formed of Guratex™, which is an aperture film with a non-woven scrim (AFW/NW) layer attached. Aperture film has small holes in it the shape of a funnel, which helps to move fluid in only one direction. We plan to design first layer with non-woven fibers passing over the holes of the aperture film. Proper orientation of this film is important such that the apertures point away from the body, allowing fluid to pass into the lower layers, but not to return.

Second layer may comprise a through air bonded (TAB) material which allows nesting of the apertures and the spreading of fluids to the manifold. Second layer 520 may be made from one to three plies of material. The through air bonded TAB 10 gram is a material similar to bleeder/breather that is used in the composite industry.

Third layer, an aperture film, is the start of the manifold. A porcupine type roller may be used to form the aperture film for forming the number of holes, or such holes may be punched or otherwise machine formed. The number of holes may be varied to determine optimum performance of the apparatus.

Fourth layer forms the center of the manifold and may comprise either TAB or bleeder/breather, a polyester non-woven fabric. The density of material may be increased around the tube exit area. In any event, the manifold nests in this material. Layer 4 has both air and urine piping units shown in FIG. 1D, but the piping units can be incorporated in any of layers 2-4. A single pump or 2 pumps can be used to pipe liquid and air to and from the garment.

Fifth layer, an outside layer back sheet (TBS) may comprise a treated breathable sheet or breathable polyethylene (PE) film.

Figure 1G:
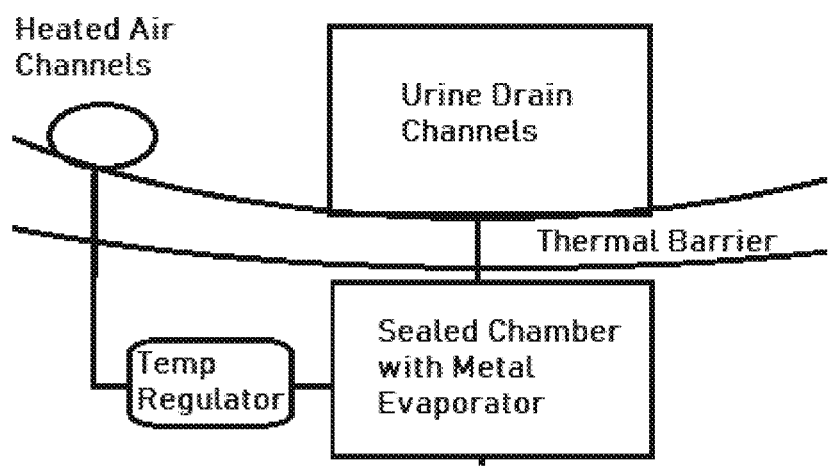

FIG. 1G shows a low-profile system with minimum components. In this version, the urine is fed through the thermal barrier to a sealed and thermally insulated chamber containing the metal evaporator. Hydrogen is generated, and heat is vented through a temperature regulator and the heated air is delivered to the heated air channels to dry the garment. While the embodiment of FIG. 1G uses separate air and urine channels, it can be one channel that is used at different times to save cost. The metal evaporator can be dispensed at a rate that is controlled using time release chemistry that controls the dissolution rate of the metal evaporator compound, thus controlling the amount of hydrogen and the heat generated to remain within safe human contact space. This embodiment is simple and inexpensive to make.

For aircraft usage or environments with explosive possibility, the presence of hydrogen is not desired. One embodiment stores the hydrogen in ruggedized gas containers that are safe. Another embodiment neutralizes the hydrogen gas with a suitable chemical. One embodiment uses an organic hydrogen getter of palladium-catalyst and a labile unsaturated hydrocarbon, e.g. buckminsterfullerene. These hydrogen getters are effective in air or inert gas at temperatures between about −20° C. and 150° C. When used in air the catalyst promotes the water-forming reaction in the container that is well removed from the skin, and thus there is a lot more hydrogen removal. Depending on the organic, we can provide gettering to lower temperatures or higher.

Figure 1H:
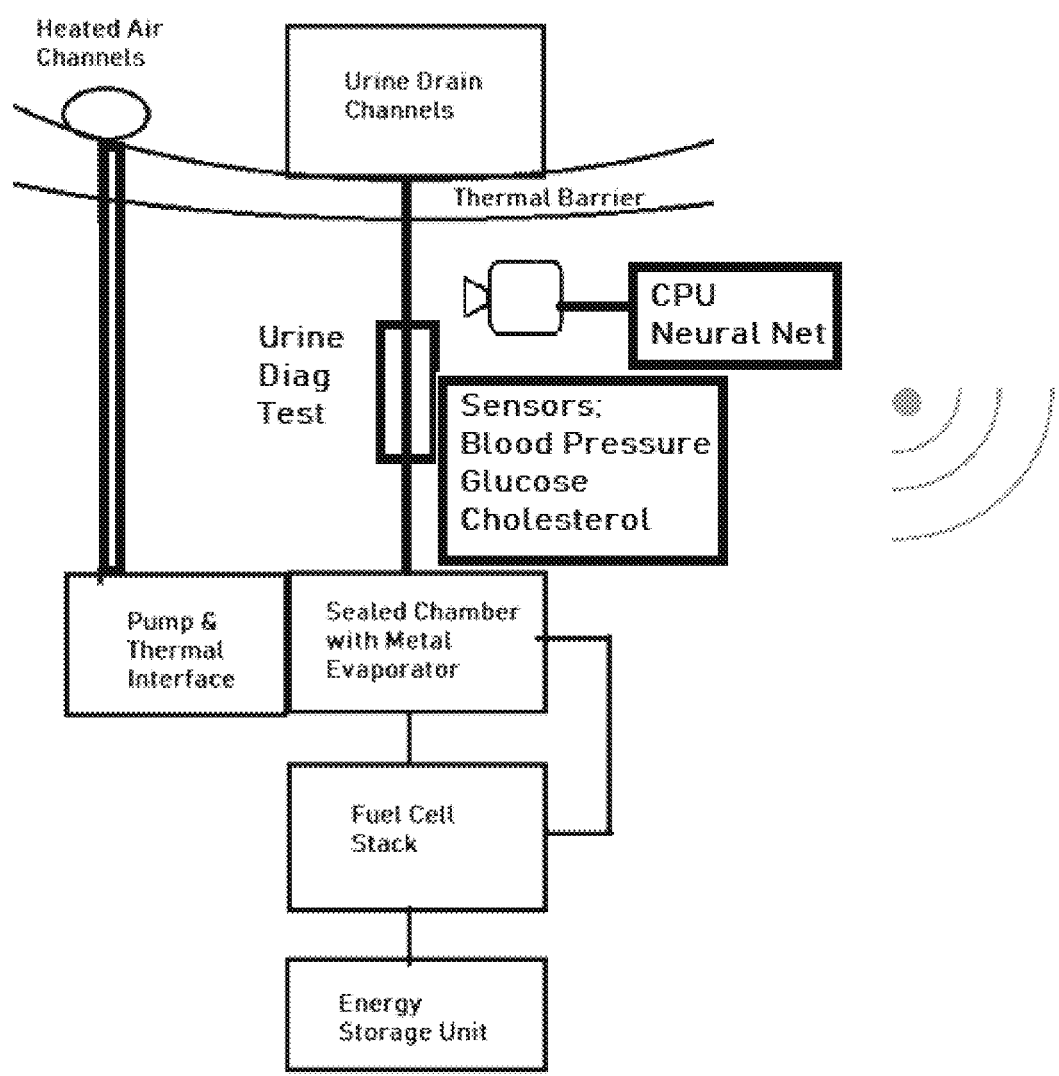

FIG. 1H shows an illustrative self-powered urine medical test system that may contain any number and any type or types of urine tests. The system includes a CPU with a neural network for visual image recognition of the liquid. The CPU receives data from a camera or imager taking images of urine flowing through the tubing. Raw images of urine are used to detect stones in the urine. Other sensors can be used such as glucose sensor and/or cholesterol sensor.

The camera can also analyze urine color. Normal urine color ranges from pale yellow to deep amber—the result of a pigment called urochrome and how diluted or concentrated the urine is. Pigments and other compounds in certain foods and medications can change urine color. Beets, berries and fava beans are among the foods most likely to affect the color. Many over-the-counter and prescription medications give urine vivid tones, such as red, yellow or greenish blue. An unusual urine color can be a sign of disease. For instance, deep red to brown urine is an identifying characteristic of porphyria, a rare, inherited disorder of red blood cells. The color also indicates hydration level: fluids dilute the yellow pigments in urine, so the more a person drinks, the clearer the urine looks, and when the person drinks less, the color becomes more concentrated—severe dehydration can produce urine the color of amber. But urine can turn colors far beyond what's normal, including red, blue, green, dark brown and cloudy white. Bloody urine is common in urinary tract infections and kidney stones. These problems usually cause pain. Painless bleeding might signal a more-serious problem, such as cancer.

Dark or orange urine. If urine is dark or orange—particularly with pale stools and yellow skin and eyes—the liver might be malfunctioning. Red or pink urine can be caused by: a) Blood. Factors that can cause urinary blood (hematuria) include urinary tract infections, an enlarged prostate, cancerous and noncancerous tumors, kidney cysts, long-distance running, and kidney or bladder stones; b) Foods. Beets, blackberries and rhubarb can turn urine red or pink; c) Medications. Rifampin (Rifadin, Rimactane), an antibiotic often used to treat tuberculosis, can turn urine reddish orange—as can phenazopyridine (Pyridium), a drug that numbs urinary tract discomfort, and laxatives containing senna.

Orange urine can result from medication such as the anti-inflammatory drug sulfasalazine (Azulfidine); phenazopyridine (Pyridium); some laxatives; and certain chemotherapy drugs. In some cases, orange urine can indicate a problem with your liver or bile duct, especially with light-colored stools. Dehydration, which can concentrate urine and make it much deeper in color, can also make urine appear orange.

Blue or green urine can be caused by dyes. Some brightly colored food dyes can cause green urine. Dyes used for some tests of kidney and bladder function can turn urine blue. A number of medications produce blue or green urine, including amitriptyline, indomethacin (Indocin, Tivorbex) and propofol (Diprivan). Familial benign hypercalcemia, a rare inherited disorder, is sometimes called blue diaper syndrome because children with the disorder have blue urine. Green urine sometimes occurs during urinary tract infections caused by pseudomonas bacteria.

Brown urine can result from: food. Eating large amounts of fava beans, rhubarb or aloe can cause dark brown urine. A number of drugs can darken urine, including the antimalarial drugs chloroquine and primaquine, the antibiotics metronidazole (Flagyl) and nitrofurantoin (Furadantin), laxatives containing cascara or senna, and methocarbamol—a muscle relaxant. Some liver and kidney disorders and some urinary tract infections can turn urine dark brown. Muscle injury from extreme exercise can result in pink or cola-colored urine and kidney damage.

Urinary tract infections and kidney stones can cause urine to appear cloudy or murky.

The camera can detect these conditions by examining images of urine over a period of time.

In other embodiments, a solid state sensor for glucose can be used. In embodiment, functionalization of GO nanosheets with MPHs is done using 200 μL of MPHs and 40 μL of 3-APTES which is added to a tube containing anhydrous $C_2H_5OH$ and kept for 10 h. After completion of the reaction process, FGO was drop-cast onto the oxygen plasma cleaned Au electrode PCB chip and allowed to evaporate at room temperature for 1 h. After modification of each Au electrode on the wafer, multiple layers were spin coated on the wafer. These layers were composed of a silane coupling layer on top of the FGO-Au electrode followed by GOX composites, nafion, a silane coupling layer, and a restricted permeable polymer layer to form the multilayer-FGO-Au electrode. Each electrode chip is composed of working, counter, and reference electrode. Prior to being diced into each chip, the glass wafer was spin coated with the aforementioned layers to form multilayers on top of the Au-electrode. The sensor collects amperometric data from Au PCBs implemented in each channel. In a single run, five different Au—PCB chips can be mounted and with the assistance of a lever each platform can be precisely inserted into the desired solutions in the tubing. Chemicals used include Silver nitrate ($AgNO_3$), tetraethoxysilane (TEOS), sodium borohydride ($NaBH_4$), ammonium hydroxide ($NH_4OH$), poly(ethylene glycol) (PEG) (Mn=10,000 g/mol), and 3-aminopropyltriethoxysilane (3-APTES); Glucose oxidase (GOx) (from *Aspergillus niger*, >100 U/mg), anhydrous ethanol ($C_2H_6O$), albumin from bovine serum (BSA), glutaraldehyde, Nafion® perfluorinated resin, 1H,1H,2H,2H-perfluorodecyl acrylate, 1,3-bis(trifluoromethyl) benzene, d-(+)-glucose (reagent grade), and N-[Tris(hydroxymethyl) methyl]-2-aminoethanesulfonic acid sodium salt (TES) buffer, all from Sigma-Aldrich. The amperometric response with glucose concentration has strong proportionality to the concentration as it increases. In one embodiment, the sensor output is compared and calibrated against a reference blood glucose test to improve accuracy, in a manner similar to blood pressure detection as detailed below.

Another glucose sensor uses a laser diode, a light dependent resistor (LDR), and a polarizer with digital output to be analyzed by a processor. The laser diode light source provides coherence radiation characteristic that is emited to the urine passing through the tube and then detected by the LDR. The LDR is able to transform light intensities to be output voltages. Upon digitization by an ADC, the processor can analyze and compare to the reference blood glucose output for calibration. The optical activity property of the glucose solution rotates the polarization direction of the polarized light when passing through the glucose solution. The amount of rotation is defined as a rotation angle which depends on (1) the nature of the solution, (2) the concentration of the solution, (3) the length of solution that is exceeded by light, (5) the wavelength of source light, and (6) the temperature of the solution. The change of angle of rotation ($\alpha$) correlates with glucose level.

In another glucose sensor embodiment, a biosensor strip comprises an electrically conductive carbon layer, having a first redox mediator, a reagent strip containing an enzyme system for the oxidation of glucose and a second redox mediator, and a silver/silver chloride reference electrode. In a preferred form of the sensor that has high sensitivity, a sensing electrode and a reference electrode are arranged so that the electrically conductive layers of the electrodes are face-to-face and sandwich the reagent strip between them. Screening for glucose is achieved by contacting the sensor with a drop of the patient's urine and comparing the current read-out with a standard calibration curve or by automatically converting the current flow generated by the test sample to units of glucose concentration. The sensor can measure urine glucose concentrations below 3 mg/dl. Measurement of urine glucose concentration with the sensor provides a non-invasive probe of a patient's blood glucose level since a linear relationship exists between blood glucose concentration and urine glucose concentration, approximately in the range between 0 to 400 mg/dl.

A solid state sensor for cholesterol can be used. The sensor performs amperometric assay of cholesterol using a sensing electrode containing a first redox mediator and a reference electrode in simultaneous contact with a reagent strip containing a second redox mediator. The presence of the second redox mediator amplifies the current flow produced by the presence of cholesterol and produces linear correlation of current flow with concentration over an extended range. The sensing electrode comprises a non-conductive support member having an electrically conductive layer containing the first redox mediator. The reference electrode is typically a Ag/AgCl electrode formed by coating an ink containing Ag/AgCl dispersed in a resin on a non-conductive base. The reagent strip is a porous or fibrous carrier, typically a paper, impregnated with a mixture containing the second redox mediator, cholesterol esterase, cholesterol oxidase, horseradish peroxidase, at least one surfactant and at least one stabilizer comprising an aqueous thickening agent. a sensing electrode having a redox mediator dispersed in an electrically conductive medium such as an electrically conductive graphite formulation; a reference electrode such as a standard silver-silver chloride (Ag/AgCl) or calomel electrode; and a reagent strip containing reagents and enzymes with the membrane reagent strip in simultaneous contact with the electrically conductive medium having the redox mediator dispersed therein and the reference electrode. The reagent strip contains a second redox mediator system, cholesterol esterase, cholesterol oxidase and horseradish peroxidase in a gel medium. The electrically conductive medium of the sensing electrode contains a redox mediator such as dimethylferrocene (DMF), 7,7,8,8-Tetracyanoquinodimethane (TCNQ), Tetrathiafulvalene (TTF), Nickelocene (Nc), N-methylacridnium (NMA+), Tetrathiatetracene (TTT), N-methylphenazinium (NMP+) or mixtures thereof. The second redox mediator contained in the reagent strip may comprise a) various dyes and mixtures such as 4-aminoantipyrine (AAP), 3,3',5,5'-tetramethylbenzidine (TMB), 2,2'-azino-di-3-ethyl-benzthiazoline sulfonate!; o-dianisidine, o-toluidine, benzidine, or b) various redox compounds, ions and complexes such as CN-, Fe(CN)6-4, I-, Co(NH3)6++, Sn++, S-2 or Tl+.

A solid-state heart rate, breathing rate, and blood pressure sensor can be used. The sensor captures optical blood flow using LED mounted near blood vessels and detect PPG output. A photoplethysmogram (PPG) is an optically obtained plethysmogram that can be used to detect blood volume changes in the microvascular bed of tissue. A PPG is often obtained by using a pulse oximeter which illuminates the skin and measures changes in light absorption. A conventional pulse oximeter monitors the perfusion of blood to the dermis and subcutaneous tissue of the skin. With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak. The change in volume caused by the pressure pulse is detected by illuminating the skin with the light from a light-emitting diode (LED) and then measuring the amount of light either transmitted or reflected to a photodiode. Each cardiac cycle appears as a peak, as seen in the figure. Because blood flow to the skin can be modulated by multiple other physiological systems, the PPG can also be used to monitor breathing, hypovolemia, and other circulatory conditions. Additionally, the shape of the PPG waveform differs from subject to subject, and varies with the location and manner in which the pulse oximeter is attached. PPG can also be configured as multi-site photoplethysmography (MPPG), e.g. making simultaneous measurements from the right and left ear lobes, index fingers and great toes, and offering further opportunities for the assessment of patients with suspected peripheral arterial disease, autonomic dysfunction, endothelial dysfunction, and arterial stiffness. In one embodiment, data mining, e.g. using deep learning, as well as a range of other pulse wave analysis techniques, is used to map the output to blood pressure. MPPG can be used for early detection and express-assessment of cardio-vascular pathologies. Direct measurements of the heartbeat pulse wave transit time (PWTT) can be used to estimate the arterial compliance, a physiologically significant parameter.

While PPG can be detected from ear lobes and fingers, such measurement restricts the user. Instead PPGs can also be obtained with sensors in the underwear from the following parts: the vagina (vaginal photoplethysmograph), the clitoris (clitoral photoplethysmograph), the esophagus, or major blood vessels in the leg portions near the underwear. One embodiment uses a vaginal photometer with a clear shell, inside of which is a light source and a photocell, which senses reflected light. The use of the device is done with the assumption that the more light that is scattered back, and that the photocell senses, the more blood is in the walls of the vagina. The output of the VPG can be filtered into two types of signals, which have different properties. The direct current signal is a measure of vaginal blood volume (VBV) and reflects the total blood volume in the vaginal tissues. The alternating current signal is a measure of vaginal pulse amplitude (VPA) and reflects the pressure change within the blood vessels of the vaginal wall associated with each heartbeat. VPA is defined as the peak-to-trough amplitude of the vaginal pulse wave. It is calculated by subtracting the means of all troughs from the means of all peaks experienced during stimulus presentation. Another embodiment uses remote photoplethysmography to determine physiological processes such as blood flow without skin contact. This is achieved by using leg camera, buttock camera, or face camera to analyze subtle momentary changes in the subject's skin color which are not detectable to the human eye. To reduce privacy issues, only PPG values are stored by the camera. Such camera-based measurement of blood oxygen levels provides a contactless alternative to conventional photoplethysmography.

FIG. 1I shows an exemplary process to continuously determine blood pressure of a patient. The process generates a blood pressure model of a patient (2002); determines a heart rate and/or blood flow velocity using an optical PPG transducer near a blood vessel (2004); and provides the heart rate and/or blood flow velocity to the blood pressure model to continuously estimate blood pressure (2006).

FIG. 1J shows another exemplary process to continuously determine blood pressure of a patient. First, during an initialization mode, a monitoring device and calibration device are attached to patient (2010). The monitoring device generates patient heart rate and/or blood flow velocity using PPG sensors, while actual blood pressure is measured by a gold standard calibration device (2012). Next, the process generates a blood pressure model based on the heart rate or blood flow velocity and the actual blood pressure (2014). Once this is done, the calibration device can be removed (2016). Next, during an operation mode, the process periodically samples heart rate or blood flow velocity from the monitoring device on a real-time basis (18) and provides the heart rate or blood flow velocity as input information to the blood pressure model to estimate blood pressure (20). This process can be done in continuously or periodically as specified by a user.

In one embodiment, to determine blood flow velocity, RF pulses are generated and transmitted into the artery. These pulses are reflected by various structures or entities within the artery (such as the artery walls, and the red blood cells within the subject's blood), and subsequently received as frequency shifts by the RF transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as RF energy (or alternatively infrared or ultrasound energy) at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and th SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart beats are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using the wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2.

The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2 P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, heart sound is captured using a sound transducer located near the heart or near the carotid artery. Once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponds to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2×N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations $O(1), O(2), \ldots O(t), \ldots, O(T)$, where each observation $O(t)$ may be either a discrete symbol under the VQ approach or a continuous vector. The sequence of observations may be modeled as a probabilistic function of an underlying Markov chain having state transitions that are not directly observable. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j)(O(t)], where the b(j)(O(t) term of the output symbol matrix is the probability of outputting observation O(t), given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of a(2,2), a probability a(2,3) of entering state 3 and a probability of a(2,4)=1−a(2,1)−a(2,2) of entering state 4. The probability a(2,1) of entering state 1 or the probability a(2,5) of entering state 5 is zero and the sum of the probabilities a(2,1) through a(2,5) is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

In one embodiment, a heart sound analyzer detects Normal S1, Split S1, Normal S2, Normal split S2, Wide split S2, Paradoxical split S2, Fixed split S2, S3 right ventricle origin, S3 left ventricle origin, opening snap, S4 right ventricle origin, S4 left ventricle origin, aortic ejection sound, and pulmonic ejection sound, among others. The sound analyzer can be an HMM type analyzer, a neural network type analyzer, a fuzzy logic type analyzer, a genetic algorithm type analyzer, a rule-based analyzer, or any suitable classifier. The heart sound data is captured, filtered, and the major features of the heart sound are determined and then operated by a classifier such as HMM or neural network, among others.

The analyzer can detect S1, whose major audible components are related to mitral and tricuspid valve closure. Mitral (MI) closure is the first audible component of the first sound. It normally occurs before tricuspid (T1) closure, and is of slightly higher intensity than T1. A split of the first sound occurs when both components that make up the sound are separately distinguishable. In a normally split first sound, the mitral and tricuspid components are 20 to 30 milliseconds apart. Under certain conditions a wide or abnormally split first sound can be heard. An abnormally wide split first sound can be due to either electrical or mechanical causes, which create asynchrony of the two ventricles. Some of the electrical causes may be right bundle branch block, premature ventricular beats and ventricular tachycardia. An apparently wide split can be caused by another sound around the time of the first. The closure of the aortic and pulmonic valves contributes to second sound production. In the normal sequence, the aortic valve closes before the pulmonic valve. The left sided mechanical events normally precede right sided events.

The system can analyze the second sound S2. The aortic (A2) component of the second sound is the loudest of the two components and is discernible at all auscultation sites, but especially well at the base. The pulmonic (P2) component of the second sound is the softer of the two components and is usually audible at base left. A physiological split occurs when both components of the second sound are separately distinguishable. Normally this split sound is heard on inspiration and becomes single on expiration. The A2 and P2 components of the physiological split usually coincide, or are less than 30 milliseconds apart during expiration and often moved to around 50 to 60 milliseconds apart by the end of inspiration. The physiological split is heard during inspiration because it is during that respiratory cycle that intrathoracic pressure drops. This drop permits more blood to return to the right heart. The increased blood volume in the right ventricle results in a delayed pulmonic valve closure. At the same time, the capacity of the pulmonary vessels in the lung is increased, which results in a slight decrease in the blood volume returning to the left heart. With less blood in the left ventricle, its ejection takes less time, resulting in earlier closing of the aortic valve. Therefore, the net effect of inspiration is to cause aortic closure to occur earlier, and pulmonary closure to occur later. Thus, a split second is heard during inspiration, and a single second sound is heard during expiration. A reversed (paradoxical) split of the second sound occurs when there is a reversal of the normal closure sequence with pulmonic closure occurring before aortic. During inspiration the second sound is single, and during expiration the second sound splits. This paradoxical splitting of the second sound may be heard when aortic closure is delayed, as in marked volume or pressure loads on the left ventricle (i.e., aortic stenosis) or with conduction defects which delay left ventricular depolarization (i.e., left bundle branch block). The normal physiological split second sound can be accentuated by conditions that cause an abnormal delay in pulmonic valve-1 closure. Such a delay may be due to an increased volume in the right ventricle as o compared with the left (atrial septal defect, or ventricular septal defect); chronic right ventricular outflow obstruction (pulmonic stenosis); acute or chronic dilatation of the. right ventricle due to sudden rise in pulmonary artery pressure (pulmonary embolism); electrical delay or activation of AA the right ventricle (right bundle branch block); decreased elastic recoil of the pulmonary artery (idiopathic dilatation of the pulmonary artery). The wide split has a duration of 40 to 50' milliseconds, compared to the normal physiologic split of 30 milliseconds. Fixed splitting of the second sound refers to split sound which displays little or no respiratory variation. The two components making up the sound occur in their normal sequence, but the ventricles are unable to change their volumes with respiration. This finding is typical in atrial septal defect, but is occasionally heard in congestive heart failure. The fixed split is heard best at base left with the diaphragm.

The third heart sound is also of low frequency, but it is heard just after the second heart sound. It occurs in early diastole, during the time of rapid ventricular filling. This sound occurs about 140 to 160 milliseconds after the second sound. The S3 is often heard in normal children or young adults but when heard in individuals over the age of 40 it usually reflects cardiac disease characterized by ventricular dilatation, decreased systolic function, and elevated ventricular diastolic filling pressure. The nomenclature includes the term ventricular gallop, protodiastolic gallop, S3 gallop, or the more common, S3. When normal it is referred to as a physiological third heart sound, and is usually not heard past the age of forty. The abnormal, or pathological third heart sound, may be heard in individuals with coronary artery disease, cardiomyopathies, incompetent valves, left to right shunts, Ventricular Septal Defect (VSD), or Patent Ductus Arteriosus (PDA). The pathological S3 may be the first clinical sign of congestive heart failure. The fourth heart sound is a low frequency sound heard just before the first heart sound, usually preceding this sound by a longer interval than that separating the two components of the normal first sound. It has also been known as an "atrial gallop", a "presystolic gallop", and an "S4 gallop". It is most commonly known as an "S4".

The S4 is a diastolic sound, which occurs during the late diastolic filling phase at the time when the atria contract. When the ventricles have a decreased compliance, or are receiving an increased diastolic volume, they generate a low frequency vibration, the S4. Some authorities believe the S4 may be normal in youth, but is seldom considered normal after the age of 20. The abnormal or pathological S4 is heard in primary myocardial disease, coronary artery disease, hypertension, and aortic and pulmonic stenosis. The S4 may have its origin in either the left or right heart. The S4 of left ventricular origin is best heard at the apex, with the patient supine, or in the left lateral recumbent position. Its causes include severe hypertension, aortic stenosis, cardiomyopathies, and left ventricular myocardial infarctions. In association with ischemic heart disease the S4 is often loudest during episodes of angina pectoris or may occur early after an acute myocardial infarction, often becoming fainter as the patient improves. The S4 of right ventricular origin is best heard at the left lateral sternal border. It is usually accentuated with inspiration, and may be due to pulmonary stenosis, pulmonary hypertension, or right ventricular myocardial infarction. When both the third heart sound and a fourth heart sound are present, with a normal heart rate, 60-100 heart beats per minute, the four sound cadence of a quadruple rhythm may be heard.

Ejection sounds are high frequency clicky sounds occurring shortly after the first sound with the onset of ventricular ejection. They are produced by the opening of the semilunar valves, aortic or pulmonic, either when one of these valves is diseased, or when ejection is rapid through a normal valve. They are heard best at the base, and may be of either aortic or pulmonic origin. Ejection sounds of aortic origin often radiate widely and may be heard anywhere on a straight line from the base right to the apex. Aortic ejection sounds are most typically heard in patients with valvular aortic stenosis, but are occasionally heard in various other conditions, such as aortic insufficiency, coarctation of the aorta, or aneurysm of the ascending aorta. Ejection sounds of pulmonic origin are heard anywhere on a straight line from base left, where they are usually best heard, to the epigastrium. Pulmonic ejection sounds are typically heard in pulmonic stenosis, but may be encountered in pulmonary hypertension, atrial septal defects (ASD) or in conditions causing enlargement of the pulmonary artery. Clicks are high frequency sounds which occur in systole, either mid, early, or late. The click generally occurs at least 100 milliseconds after the first sound. The most common cause of the click is mitral valve prolapse. The clicks of mitral origin are best heard at the apex, or toward the left lateral sternal border. The click will move closer to the first sound when volume to the ventricle is reduced, as occurs in standing or the Valsalva maneuver. The opening snap is a short high frequency sound, which occurs after the second heart sound in early diastole. It usually follows the second sound by about 60 to 100 milliseconds. It is most frequently the result of the sudden arrest of the opening of the mitral valve, occurring in mitral stenosis, but may also be encountered in conditions producing increased flow through this valve (i.e., VSD or PDA). In tricuspid stenosis or in association with increased flow across the tricuspid valve, as in ASD, a tricuspid opening snap may be heard. The tricuspid opening snap is loudest at the left lateral sternal border, and becomes louder with inspiration.

Murmurs are sustained noises that are audible during the time periods of systole, diastole, or both. They are basically produced by these factors: 1) Backward regurgitation through a leaking valve or septal defect; 2) Forward flow through a narrowed or deformed valve or conduit or through an arterial venous connection; 3) High rate of blood flow through a normal or abnormal valve; 4) Vibration of loose structures within the heart (i.e., chordae tendineae or valvular tissue). Murmurs that occur when the ventricles are contracting, that is, during systole, are referred to as systolic murmurs. Murmurs occurring when the ventricles are relaxed and filling, that is during diastole, are referred to as diastolic murmurs. There are six characteristics useful in murmur identification and differentiation:

1) Location or the valve area over which the murmur is best heard. This is one clue to the origin of the murmur. Murmurs of mitral origin are usually best heard at the apex. Tricuspid murmurs at the lower left lateral sternal border, and pulmonic murmurs at base left. Aortic systolic murmurs are best heard at base right, and aortic diastolic murmurs at Erb's point, the third intercostal space to the left of the sternum.

2) Frequency (pitch). Low, medium, or high.

3) Intensity.

4) Quality.

5) Timing. (Occurring during systole, diastole, or both).

6) Areas where the sound is audible in addition to the area over which it is heard best.

Systolic murmurs are sustained noises that are audible during the time period of systole, or the period between S1 and S2. Forward flow across the aortic or pulmonic valves, or regurgitant flow from the mitral or tricuspid valve may produce a systolic murmur. Systolic murmurs may be normal, and can represent normal blood flow, i.e., thin chest, babies and children, or increased blood flow, i.e., pregnant women. Early systolic murmurs begin with or shortly after the first sound and peak in the first third of systole. Early murmurs have the greatest intensity in the early part of the cycle. The commonest cause is the innocent murmur of childhood (to be discussed later). A small ventricular septal defect (VSD) occasionally causes an early systolic murmur. The early systolic murmur of a small VSD begins with S1 and stops in mid systole, because as ejection continues and the ventricular size decreases, the small defect is sealed shut, causing the murmur to soften or cease. This murmur is characteristic of the type of children's VSD located in the muscular portion of the ventricular septum. This defect may disappear with age. A mid-systolic murmur begins shortly after the first sound, peaks in the middle of systole, and does not quite extend to the second sound. It is the crescendo decrescendo murmur which builds up and decrease symmetrically. It is also known as an ejection murmur. It most commonly is due to forward blood flow through a normal, narrow or irregular valve, i.e., aortic or pulmonic stenosis. The murmur begins when the pressure in the respective ventricle exceeds the aortic or pulmonary arterial pressure. The most characteristic feature of this murmur is its cessation before the second sound, thus leaving this latter sound identifiable as a discrete entity. This type of murmur is commonly heard in normal individuals, particularly in the young, who usually have increased blood volumes flowing over normal valves. In this setting the murmur is usually short, with its peak intensity early in systole, and is soft, seldom over 2 over 6 in intensity. It is then designated as an innocent murmur. In order for a murmur to be classified as innocent (i.e. normal), the following are present:

1) Normal splitting of the second sound together with absence of abnormal sounds or murmurs, such as ejection sounds, diastolic murmurs, etc.

2) Normal jugular venus and carotid pulses

3) Normal precordial pulsations or palpation, and

4) Normal chest x-ray and ECG

Obstruction or stenosis across the aortic or pulmonic valves also may give rise to a murmur of this type. These murmurs are usually longer and louder than the innocent murmur, and reach a peak intensity in mid-systole. The murmur of aortic stenosis is harsh in quality and is heard equally well with either the bell or the diaphragm. It is heard best at base right, and radiates to the apex and to the neck bilaterally.

An early diastolic murmur begins with a second sound, and peaks in the first third of diastole. Common causes are aortic regurgitation and pulmonic regurgitation. The early diastolic murmur of aortic regurgitation usually has a high frequency blowing quality, is heard best with a diaphragm at Erb's point, and radiates downward along the left sternal border. Aortic regurgitation tends to be of short duration, and heard best on inspiration. This respiratory variation is helpful in differentiating pulmonic regurgitation from aortic regurgitation. A mid-diastolic murmur begins after the second sound and peaks in mid-diastole. Common causes are mitral stenosis, and tricuspid stenosis. The murmur of mitral stenosis is a low frequency, crescendo de crescendo rumble, heard at the apex with the bell lightly held. If it radiates, it does so minimally to the axilla. Mitral stenosis normally produces three distinct abnormalities which can be heard: 1) A loud first sound 2) An opening snap, and 3) A mid-diastolic rumble with a late diastolic accentuation. A late diastolic murmur occurs in the latter half of diastole, synchronous with atrial contraction, and extends to the first sound. Although occasionally occurring alone, it is usually a component of the longer diastolic murmur of mitral stenosis or tricuspid stenosis. This murmur is low in frequency, and rumbling in quality. A continuous murmur usually begins during systole and extends through the second sound and throughout the diastolic period. It is usually produced as a result of one of four mechanisms: 1) An abnormal communication between an artery and vein; 2) An abnormal communication between the aorta and the right side of the heart or with the left atrium; 3) An abnormal increase in flow, or constriction in an artery; and 4) Increased or turbulent blood flow through veins. Patent Ductus Arteriosus (PDA) is the classical example of this murmur. This condition is usually corrected in childhood. It is heard best at base left, and is usually easily audible with the bell or diaphragm. Another example of a continuous murmur is the so-called venous hum, but in this instance one hears a constant roaring sound which changes little with the cardiac cycle. A late systolic murmur begins in the latter half of systole, peaks in the later third of systole, and extends to the second sound. It is a modified regurgitant murmur with a backward flow through an incompetent valve, usually the mitral valve. It is commonly heard in mitral valve prolapse, and is usually high in frequency (blowing in quality), and heard best with a diaphragm at the apex. It may radiate to the axilla or left sternal border. A pansystolic or holosystolic murmur is heard continuously throughout systole. It begins with the first heart sound, and ends with the second heart sound. It is commonly heard in mitral regurgitation, tricuspid regurgitation, and ventricular septal defect. This type of murmur is caused by backward blood flow. Since the pressure remains higher throughout systole in the ejecting chamber than in the receiving chamber, the murmur is continuous throughout systole. Diastolic murmurs are sustained noises that are audible between S2 and the next S. Unlike systolic murmurs, diastolic murmurs should usually be considered pathological, and not normal. Typical abnormalities causing diastolic murmurs are aortic regurgitation, pulmonic regurgitation, mitral stenosis, and tricuspid stenosis. The timing of diastolic murmurs is the primary concern of this program. These murmurs can be early, mid, late and pan in nature. In a pericardial friction rub, there are three sounds, one systolic, and two diastolic. The systolic sound may occur anywhere in systole, and the two diastolic sounds occur at the times the ventricles are stretched. This stretching occurs in early diastole, and at the end of diastole. The pericardial friction rub has a scratching, grating, or squeaking leathery quality. It tends to be high in frequency and best heard with a diaphragm. A pericardial friction rub is a sign of pericardial inflammation and may be heard in infective pericarditis, in myocardial infarction, following cardiac surgery, trauma, and in autoimmune problems such as rheumatic fever.

In addition to heart sound analysis, the timing between the onset and offset of particular features of the ECG (referred to as an interval) provides a measure of the state of the heart and can indicate the presence of certain cardiological conditions.

In addition to providing beat-to-beat timing information for other sensors to use, the patterns of the constituent waveform features determined by the HMM or neural networks, among other classifiers, can be used for detecting heart attacks or stroke attacks, among others. For example, the detection and classification of ventricular complexes from the ECG data is can be used for rhythm and various types of arrhythmia to be recognized. The system analyzes pattern recognition parameters for classification of normal QRS complexes and premature ventricular contractions (PVC). Exemplary parameters include the width of the QRS complex, vectorcardiogram parameters, amplitudes of positive and negative peaks, area of positive and negative waves, various time-interval durations, amplitude and angle of the QRS vector, among others. The EKG analyzer can analyze EKG/ECG patterns for Hypertrophy, Enlargement of the Heart, Atrial Enlargement, Ventricular Hypertrophy, Arrhythmias, Ectopic Supraventricular Arrhythmias, Ventricular Tachycardia (VT), Paroxysmal Supraventricular Tachycardia (PSVT), Conduction Blocks, AV Block, Bundle Branch Block, Hemiblocks, Bifascicular Block, Preexcitation Syndromes, Wolff-Parkinson-White Syndrome, Lown-Ganong-Levine Syndrome, Myocardial Ischemia, Infarction, Non-Q Wave Myocardial Infarction, Angina, Electrolyte Disturbances, Heart Attack, Stroke Attack, Hypothermia, Pulmonary Disorder, Central Nervous System Disease, or Athlete's Heart, for example.

Other sensors can detect targets such vitamin level. The urine can be deposited onto a test matrix, which may be divided into regions, each of which is impregnated with reagents and materials that condition the sample and perform one or more specific test reactions. The system includes a camera that analyzes images of urine to detect stone conditions in the urine. The pump can provide different exposure times and for different urine volumes needed for different tests.

For example, a lateral flow assay that may be incorporated for example into the test matrix. Liquid sample and buffer are dispensed onto the pad. An absorbent pad on the opposite side of the lateral flow assay provides a pulling force that moves liquid through the stages of the test. First the sample liquid flows to conjugate pad, into which a detection conjugate is embedded. The sample and conjugate then flow into nitrocellulose membrane. As the lateral flow along membrane continues, the sample and conjugate reach the test line, which contains material that reacts with the analyte being tested for. If enough analyte is present, the test line may for example change color and the color change or intensity of the color may indicate whether the analyte is present and in what quantities. A benefit of one or more embodiments of the system is that test results may be quantitative, rather than simply binary (analyte present or not present); using the systems optical imaging for example combined with analysis software, the intensity of the color or other features of the test line may be analyzed to determine the amount of analyte present. One or more embodiments may incorporate lateral flow assays with multiple test lines that may for example test for multiple analytes on the same assay.

In one or more embodiments, test matrices may incorporate one or more tests that require a multistep chemical reaction. These tests may be performed for example using multiplexed lateral flow strip or vertical flow stacks. A multiplexed lateral flow strip may for example have multiple test lines per strip. In vertical flow stacks, sample and conjugate flow vertically and may be guided into multiple channels in parallel and into multiple test areas in series. Illustrative tests that may require multi-step assays include for example vitamins B7, B9, and B12, and other targets that cannot be measured with single step colorimetric tests.

In one or more embodiments, test matrices may be configured with perforations on the "exposure side" of the matrix through which urine is delivered, with optical imaging performed on the opposite "read side" of the matrix. For example, one or more embodiments may perform tests by clamping and sealing the test chamber against the exposure side (the side with holes) and filling the chamber with urine. Urine may for example flow through the holes at a controlled rate (based for example on hole size and pattern) and saturate the absorbent material. The sensor or sensors may look at the read side and record signals as each assay changes color/intensity over time after urine exposure; this approach may increase the reliability of the test results for example compared to taking a single reading after a countdown time. One or more embodiments may expose the tests to urine and take multiple readings at known time intervals as the test color/intensity changes. Since different tests may require different amounts of sample, flow rates may be controlled individually for each test in the test matrix.

In one or more embodiments the rate of filling of test chamber may be precisely controlled to provide precise urine exposure times for each test. In one or more embodiments, controlled filling of the test chamber may be further combined with differences in the perforation sizes or patterns behind each test to further control the exposure time and rate of urine flow for each test.

In one or more embodiments, rather than exposing all test pads to urine directly via the exposure side of a test matrix, a test matrix may for example have a single sample pad (or a limited number of sample pads), and the matrix may include fluid paths such as glass fibers through which urine is wicked to all of the tests, pulled for example by absorbent pads via capillary action. In general, the test matrix may have any number and configuration of fluidics paths integrated into the matrix to enable delivery of urine to tests. One or more embodiments may incorporate a lateral flow test that has one or more colorimetric tests located in the middle of the lateral flow strip, so that the lateral flow action itself delivers urine to multiple tests. In one or more embodiments, multiple fluidics paths may be integrated into the test chamber to enable separate delivery of urine to different tests or groups of tests, or to more precisely control the timing of urine delivery to each test.

One or more embodiments may illuminate the test matrix with selected wavelengths of light to maximize the sensitivity of one or more urine analysis tests. Different tests may respond to different wavelengths; therefore, one or more embodiments may provide several different wavelengths for illumination of the test matrix. Certain assays may respond better to different wavelengths; hence in one or more embodiments the optical capture system may provide various wavelengths for illumination. In one or more embodiments these different wavelengths may be provided for example by different LEDs, each emitting one of the desired wavelengths. In one or more embodiments a diffraction grating may split a single source of incident light into various wavelengths that may be used for test matrix illumination. A diffraction grating may also be used to divide reflected light into different wavelength components like a prism. Diffracting different wavelengths at different angles onto different regions of an optical sensor (such as for example a CMOS sensor) creates a type of spectrophotometer.

In one embodiment, the process can be initiated using a smart phone or computer. In step 401 the system accepts user input via a computer, such as a mobile device or remote computer or local button for example and initiates a test. In step 402 the system accepts a urine sample from the user, i.e., accepts urine into the collector. In step 403 an unused test matrix is cycled from the test matrix storage chamber into the test chamber. In step 404 a fluid transport system, such as for example a microfluidics system, transports urine from the tubings of FIG. 1A into the test chamber and dispenses urine onto the test matrix regions containing tests. In step 405, the optical system illuminates the test matrix and captures images with one or more sensors to detect changes in color or intensity from the reaction of urine with the reagents on the test matrix. In step 406, the data captured by the imaging sensor or sensors on color or intensity is transmitted to one or more image analysis elements. Image analysis elements may be integrated into the urine testing system or remote from the system. In step 407, the used test matrix is moved to the waste chamber. Then in step 408, the fluid transport system is flushed with cleaning solution. After cleaning, in step 409 the system is ready for a subsequent test. Images of the test matrix may be analyzed to determine the results of the urine tests embedded in the test matrix. An image or other signals to be analyzed may be any data captured by any sensor or sensors of the urine analysis system. Analysis of images or other signals may be performed local to the urine analysis system, remote from the system, or via a combination of local and remote analysis.

One or more embodiments may include or utilize a recommendation engine, which may for example incorporate algorithms that convert multi-point health data sets into dietary and lifestyle recommendations. Recommendations may be based on combined measurements of multiple factors over time. This approach provides several potential benefits since the body's absorption and use of specific vitamins or minerals may depend on the presence of other vitamins or minerals. An example is vitamin B9 which can't be effectively utilized without adequate levels of Vitamin B12 (as well as Vitamin B6 and Iron). Magnesium utilization depends on levels of Vitamin B6, Calcium, Potassium, Zinc, etc. Zinc utilization depends on levels of Copper. Copper utilization depends on levels of Vitamin C, Iron, and Zinc. Vitamin C utilization depends on levels of Iron. Since embodiments of the system may measure many of the body's important vitamins and minerals (along with hydration, amino acids, hormone levels, and other health metrics) on a daily basis, a new layer of data may be created as users implement dietary recommendations and see the results in real time. Providing continuously updated recommendations and daily monitoring of results offers significantly more potential than the current approach in the art of obtaining yearly test results at an annual checkup and rechecking results months later after recommended changes have been implemented. Results may be personalized to each unique individual based on sex, height, weight, and other factors. Actionable recommendations may be rapidly tested and validated or adjusted by a machine learning or artificial intelligence process coupled to the recommendation engine. The recommendation engine may be programmed with medical and nutritional input from health advisors and a machine learning system may be incorporated to update the recommendation engine as more data is collected.

By using the materials discussed above, the edges of the apparatus may be sealed together by heat bonding, melting adhesive (e.g., hot glue), air stitch, or other methods. Such garment construction lends itself to inexpensive mass production. The system does not require transferring aircraft control to the WSO or any amount of un-strapping. The collection bags are sealed and much easier to handle and stow in the cockpit than other systems. The unit is a key mission enabler/enhancer for long duration missions or missions where the amount of flight/survival gear makes using a traditional piddle pack close to impossible or cause safety of flight issues with disconnecting from the seat belts. The system helps promote staying well hydrated especially in the winter/cold weather environments when wearing additional gear makes using the traditional piddle pack near impossible.

The system is advantageous in that:

Garment provides bladder relief on typical missions up to 3 hours in duration and long-duration missions up to 16 hours without causing clinically significant skin irritation or physiological adverse side effects such as prolonged exposure to urine, infections, hot spots, pinching, rubbing, extreme heat, etc. This is achieved through the patent-pending inflatable garment concept.

Garment and pump are sized to collect 800 cc per individual use.

Garment does not restrict movement of aircrew before, during, or after flight, nor interfere with performance of duty or result in aircrew unstrapping neither from seat nor with emergency egress procedures, nor interfere with operation of the aircraft in flight, such as interfering with the aircraft controls.

Garment with Aluminum substrate is durable and can operate in an aircraft environment which include: exposure to Electro-magnetic Interference (EMI), high humidity, high and low temperatures (−20° C./−4° F. to +70° C./158° F.), dust, rain, static electricity, salt fog and environmental contaminants such as hydraulic fluid and will comply with applicable military standards (ex. MIL-STD 810D, 461G).

Garment is usable for the entire flight in conjunction with a flight uniform, anti-g suit, and exposure suit without unstrapping/releasing from a restraint system.

Diaper like garment is compatible with all aircraft ejection seats.

The inflatable bed frame enables hands-free urine collection.

Hydrogen is captured and neutralized to be flame resistant and not ignite in highly explosive atmospheres.

Garment allows the user to don the device or applicable components while donning flight gear without assistance, or don without undressing just prior to going to the flight line.

Garment is compatible with Life Support Systems flight gear and be discrete in appearance when worn.

Garment is disposable, and no maintenance other than battery replacement, battery charging, and system cleaning, all of which can be performed by the user, with no special disposal requirements (disposal shall be in regular trash service).

If components are to be cleaned and reused, the cleaning process should dry the components quickly, eliminate residual odor, and be a process that is conducted by the user.

Gases produced by water electrolysis is neutralized within the undergarment materials and not be released into the surrounding spaces.

Tubes may comprise Latex™ tubing with holes 750 approximately ⅛" in diameter punched along the inside. Tubes in turn are connected to a T fitting 770 at the front which goes to the pump. Tubes in manifold may be nested into 4.5 oz bleeder/breather cloth (non woven polyester) otherwise known as TAB. The outside layer, known as a back sheet, may comprise a plastic film or coated nylon for a waterproof backing that is breathable. A transition layer may be provided which allows the fluid to disperse and also prevents damage to the cones of the aperture film. The innermost layer is the aperture film which acts as a one way check valve allowing fluids to come in but not back out. The orientation of the cones is pointed toward the manifold. Additional layers may be added to improve wearability and comfort. In one embodiment, disposable protective underwear P/N PASPE630AA manufactured by Tyco/Healthcare/Kendall, 601 Allendale Road, King of Prussia, Pa. 19407, and distributed by Wal-Mart can be used where absorbent core is simply removed from this off-the-shelf product and directly replaced with the vacuum core, secured with spray adhesive, and then reassembled. The Tyco protective underwear has features like elastic bands to seal the edges and high waste band which are well known to this field and comes as a uni-sex garment, making it more than suitable for use in the present invention. The small/medium size fits anywhere from 34" to 46" hips, making it applicable to a broad range of users.

The apparatus of the present invention may be activated in a number of ways. In one embodiment, a timer or the like may be used to periodically activate the apparatus to remove any urine waste from the garment. In this manner, a simple, hands-free operation is assured. In an alternative embodiment, a manual switch may be provided to allow a user to manually evacuate the garment. A manual switch and timer may be used either alone or in combination. In another embodiment, which may be provided singularly, or in combination with the other activation means, a moisture sensor may be provided to allow the system to automatically activate when moisture is detected.

A ball check valve may be located between the pump and the garment. The ball check valve may prevent accidental spillage during inverted maneuvers. A similar system is used in aircraft lead acid battery vents. Quick-connects may be added to the hoses to ensure proper connection by either male or female connectors or by using different sizes of fittings for different connectors.

In addition, the present invention may also be used to form a device that can be used by hospitals in what is currently called a dead pad. This pad is placed under the patient. Presently body fluids are passed into this article and absorbed in an absorbent core requiring regular replacement. Bodily fluids could be removed allowing the patient to be more comfortable for longer periods of time. The present invention may also be used to obtain fluid samples (e.g., urine samples) for testing and analysis in a non-invasive manner. In addition, the present invention may also be used, in the same or modified form, to drain fluids from wounds and the like. The system can be in a form suitable for use with animals other than humans, including research animals, zoo animals, farm animals, animals in transport, and the like. The apparatus of the present invention may be used, for example, with horses and the like to capture urine in situations where such animal urine may be objectionable (e.g., city environment or the like).

Figure 2C:
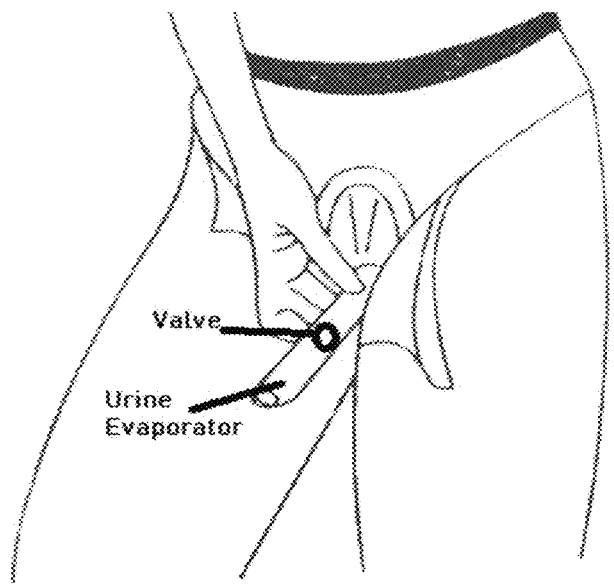

FIGS. 2A-2C show other exemplary garments to render urine inert. FIG. 2A shows a brief with a condom in a brief pocket. The condom is connected to a sealed chamber with aluminum compound (collectively a urine evaporator) to convert the urine hydrogen and byproducts. FIG. 2B shows a similar receptacle that is connected to a sealed urine evaporator containing the aluminum compound. During use the condom is applied to the penis, and urine flows to the sealed chamber containing the evaporation components and converted into gas which can be neutralized or used to generate electricity for field use.

FIG. 2C shows an exemplary urine capture device operable in a standing position by a female user. The female urine device generally comprises an inner sealing ring directed toward a funnel and an outer sealing ring that surrounds the inner sealing ring. The inner sealing ring has outer and inner walls. The outer wall is vertical and extends upward from the outer sealing ring to the perimeter of the inner sealing ring. The inner walls begin with a pronounced taper at the rear extending peak blending to a substantially vertical state at the front cap portion. The taper of the inner walls is designed to encompass the female human form. Specifically, the inner walls surround and are conformed to the exterior of the labia minora; the pronounced taper of the inner walls surrounds the rearmost portion of the labia minora where the labia minora are quite thin or of little mass (near the opening of the vagina) while the substantially vertical portion of the inner walls allows for the space to surround the larger or more massive front most portion of the labia minora (the point at which the labia minora join or meet). The inner walls of the inner sealing ring blend smoothly into an inner funnel portion of the funnel. The outer sealing ring is designed to encompass the female human form to cover the labia majora. The device funnel to a sealed chamber or urine evaporator through a valve that the user can selectively control when urine contacts the aluminum compound.

The system is ideal for harvesting energy for personal computing requirements such as AR/VR or for augmented robotic systems. A wearable liquid tank on an underwear, pant, vest, or strap-on pouch can hold water or any liquid with some water therein, such as gray water, rain water, urine, for example. The liquid contacts an aluminum galvanic alloy supplied by a tank connected to the liquid tank to dispense the liquid to the alloy, or to expose the liquid to the alloy. The resulting hydrogen is optionally stored in a hydrogen gas tank coupled to the aluminum galvanic alloy tank. On demand, a fuel cell stack can receive hydrogen gas from the hydrogen gas tank and oxygen from the atmosphere for generating electricity to power a motor electrically coupled to the fuel cell stack to rotate the wheels on the vehicle. Aluminum has the highest volumetric energy density among non-nuclear fuels—more than twice that of gasoline and more than five times that of methanol. If water is available, aluminum is a very desirable choice to generate power via hydrogen generation. If the total required volume of water is considered, the volumetric energy density of aluminum is 65% that of gasoline. However, when the hydrogen is used in fuel cell technology, 50% of the water can be reclaimed and utilized (i.e. removing half of the amount of water) then the energy density equals approximately that of gasoline. Such systems fueled with pure hydrogen emit no pollutants, only water and heat, while those using hydrogen-rich fuels and a reformer produce only small amounts of air pollutants. A power converter coupled to the fuel cell stack to regulate power to the motor. An energy storage device such as a supercapacitor or lithium battery, among others, can store power from the power converter. A solar panel can also be connected to the power converter. In another embodiment for distributed grid power, when the vehicle is parked, an AC converter coupled to the fuel cell stack and to an electrical grid, the AC converter controlled to provide energy to the grid on command. Liquid by-product (water) from the fuel cell stack is deposited into the liquid tank, thus completing a closed loop to minimize water waste.

In other implementations, the main energy source is assisted by one or more energy storage devices including fuel cell (FC), Aluminum Galvanic Fuel Cell, and Battery and/or supercapacitors. Thereby the system cost, mass, and volume can be decreased, and a significant better performance can be obtained. Two often used energy storage devices are batteries and SCS. They can be connected to the fuel cell stack in many ways. A simple configuration is to directly connect two devices in parallel, (FC/battery, FC/Aluminum, or battery/Aluminum). However, in this way the power drawn from each device cannot be controlled, but is passively determined by the impedance of the devices. The impedance depends on many parameters, e.g. temperature, state-of-charge, health, and point of operation. Each device might therefore be operated at an inappropriate condition, e.g. health and efficiency. The voltage characteristics also have to match perfectly of the two devices, and only a fraction of the range of operation of the devices can be utilized, e.g. in a fuel cell battery configuration the fuel cell must provide almost the same power all the time due to the fixed voltage of the battery, and in a battery/supercapacitor configuration only a fraction of the energy exchange capability of the supercapacitor can be used. This is again due to the nearly constant voltage of the battery. By introducing DC/DC converters one can chose the voltage variation of the devices and the power of each device can be controlled.

Urine or water is applied to the aluminum alloy to generate gas which is stored in a hydrogen tank. The hydrogen is provided to a fuel cell stack to generate electricity, which is regulated by the power converter and provided to battery or energy storage device. The battery output is further regulated by a power converter and provided to a motor to drive the vehicle. The vehicle dynamics are translated to torque control signals to the motor, and the power converter is controlled to supply power to the motor. The power consumption is monitored by a fuel management system which monitors the battery with a state of charge (SOC). If the battery requires charging, the water is exposed to the aluminum allow to generate hydrogen and provided to the fuel cell stack.

An on-board hydrogen generation system might utilize most, but not all, of the metal reactant. Refueling in this case entails not only supplying more aluminum or alloy, but also the removal of the aluminum hydroxide reaction product. Thus, when the liquid is supplied to the metal container, the system separates the reaction products from the unreacted aluminum on-board the vehicle so that waste products can be discharged from the vehicle at the same time that it is refueled with fresh quantities of aluminum alloy and water.

Next, the process of making a metal alloy for hydrogen production is detailed. Preferably, the alloy is aluminum, but other metals can be used. Aluminum powder produces the largest amount of hydrogen per unit mass throughout the temperature range, followed by the magnesium powder. Manganese powder, which produces the largest amount of hydrogen per unit volume at high temperatures, exhibits a sharp increase in yield between 120 and 150° C. The aluminum and magnesium powders exhibit high reaction rates, and together with the manganese powder, serve as fuels for in-situ hydrogen production. Other metal powders can be used, as noted in Yavor et al, Comparative reactivity of industrial metal powders with water for hydrogen production, Int'l Journal of Hydrogen Energy, Vol 40, Issue 2, 12 Jan. 2015, pp 1026-1036, the content of which is incorporated by reference.

The metal alloy can be carbon and a form of nitrogen called tetranitrogen and manganese. The result was a catalyst that's comparable in its ability to split water—the reaction needed to produce hydrogen—as platinum and other metal-based alternatives. The result is milled to produce powders reactive with water as detailed below.

Another exemplary process using metal alloy for generating hydrogen gas upon contact with water or other aqueous compositions is discussed next. The method applies a metal such as magnesium, manganese, aluminum, a metal alloy or another metal-based composition with a second metal, second alloy or other second metal-based composition. As noted above, the metal can be magnesium, manganese, among others A milling machine is applied to the aluminum, aluminum alloy or other aluminum-based composition and second metal, alloy or other metal-based composition to produce a powder with grains or subgrains of aluminum with individual grains or subgrains of the dispersed second metal, second alloy or other second metal-based composition having atomic to nano-scale or micro-scale dimensions.

In certain embodiments, the milling occurs at a temperature less than or equal to the ductile to brittle transition temperature of tin (Sn) 13.2° C. (286.2 K). In other embodiments, the milling occurs at a temperature 50° C. below the ductile to brittle transition temperature for Tin (Sn). In certain other embodiments, the milling occurs at a temperature 100° C. below the ductile to brittle transition temperature for tin (Sn). In other embodiments, the milling occurs at a temperature 150° C. below the ductile to brittle transition temperature for tin (Sn). In yet other embodiments the milling occurs at a temperature 270° C. below the ductile to brittle transition temperature for tin (Sn). In other embodiments, the milling occurs at a temperature within 25° C. of the ductile to brittle transition temperature for tin (Sn). In yet other embodiments, the milling occurs at a temperature within 50° C. of the ductile to brittle transition temperature for tin (Sn), or within 100° C. of the ductile to brittle transition temperature for tin (Sn) or is conducted over temperature range from about +100° C. to about −270° C. in which the aluminum (Al) undergoes embrittlement. certain embodiments, the milling occurs over temperature range from about +100° C. to about −270° C. and in which the dispersed phase or solute comprises tin (Sn), magnesium (Mg), silicon (Si), bismuth (Bi), lead (Pb), gallium (Ga), indium (In), zinc (Zn) carbon (C), or mixtures thereof and further wherein the disperse phase or solute undergoes embrittlement. In some embodiments, the milling occurs under or in a low temperature liquid or fluid that is at a temperature ≤24° C. or under or in a cryogenic liquid that is at a temperature ≤−75° C.

In some embodiments the milled, powder composition comprises at least 0.1 atomic percent tin (Sn), magnesium (Mg), silicon (Si), bismuth (Bi), lead (Pb), gallium (Ga), indium (In), zinc (Zn) or carbon (C), or a mixture thereof. In other embodiments, the milled, powder composition comprises at least 1 atomic percent tin (Sn), magnesium (Mg), silicon (Si), bismuth (Bi), lead (Pb), gallium (Ga), indium (In), zinc (Zn) or carbon (C), or a mixture thereof. In yet other embodiments, the milled, powder composition comprises at least 2.5 atomic percent tin (Sn), magnesium (Mg), silicon (Si), bismuth (Bi), lead (Pb), gallium (Ga), indium (In), zinc (Zn) or carbon (C), or a mixture thereof. In still yet other embodiments, the milled, powder composition comprises between about 0.1 atomic percent tin and about 49.99 atomic percent tin (Sn), magnesium (Mg), silicon (Si), bismuth (Bi), lead (Pb), gallium (Ga), indium (In), zinc (Zn) or carbon (C), or a mixture thereof.

In certain embodiments, the milled, powder composition comprises at least 0.1 atomic percent tin or bismuth or a mixture thereof. In certain other embodiments, the milled, powder composition comprises finely divided powder particles having diameters ranging from about 1 micron to about 10,000 microns. In other embodiments, the milled, powder composition comprises finely divided powder particles having diameters ranging from about 1 micron to about 1000 microns. In yet other embodiments, the milled, powder composition comprises finely divided powder particles having diameters ranging from about 10 nanometers to about 1000 nanometers.

In certain embodiments, the method further comprises adding a surfactant to prevent the powder from bonding to the milling container during milling. In certain embodiments, the present invention provides a dispersion of solutes in the solvent or matrix resulting in a reaction rate wherein the hydrogen production is greater than 74% of the theoretical yield for aluminum at 25° C. (298 K) and 1 atm. in less than or equal to 30 seconds. In certain embodiments, the present invention also provides a dispersion of solutes in the solvent or matrix resulting in a reaction rate wherein hydrogen production is greater than 74% of the theoretical yield for aluminum at 25° C. (298 K) and 1 atm. in 5 minutes. In yet other embodiments, the present invention provides a dispersion of solutes in the solvent or matrix resulting in a reaction rate wherein the hydrogen production is greater than 74% of the theoretical yield for aluminum at 25° C. (298 K) and 1 atm. in 50 minutes. In still yet other embodiments, the present invention provides a dispersion of solutes in the solvent or matrix resulting in a reaction rate wherein the hydrogen production is greater than 74% of the theoretical yield for aluminum at 25° C. (298 K) and 1 atm. in 500 minutes. And in other embodiments, a dispersion of solutes in the solvent or matrix results in a reaction rate wherein the hydrogen production is greater than 74% of the theoretical yield for aluminum at 25° C. (298 K) and 1 atm. in 5000 minutes.

In some embodiments, the method further includes compacting the milled, powder composition into a densified structure. And in some embodiments, the method includes compacting the milled, powder composition into a tablet, a rod, a pellet or a bulk part wherein the tablet, rod, pellet or bulk part generates hydrogen when the tablet, rod, pellet or bulk part contacts water or a water containing liquid.

A galvanic metal microstructure can be produced with: an anodic matrix comprising aluminum, an aluminum alloy or another aluminum-based composition; and a cathodic disperse phase comprising a second metal, second alloy or other second metal-based composition is selected from the group consisting of: tin (Sn), magnesium (Mg), silicon (Si), bismuth (Bi), lead (Pb), gallium (Ga), indium (In), zinc (Zn), carbon (C), and mixtures and alloys thereof wherein said cathodic disperse phase forms galvanic couples with the anodic matrix and produce hydrogen gas when said galvanic metal microstructure contacts with water, a water containing liquid or another electrolyte. In some embodiments, the cathodic disperse phase comprises a plurality of discreet particles having a length of less than 1 millimeter. In other embodiments, the cathodic disperse phase comprises a plurality of discreet particles having a length of less than 1000 nanometers. In yet other embodiments, the cathodic disperse phase comprises a plurality of discreet particles having a length of less than 500 nanometers, or a length of less than 200 nanometers, or less than 100 nanometers or even less than 50 nanometers. In certain embodiments, the cathodic disperse phase comprises tin (Sn). In certain other embodiments, the cathodic disperse phase consists primarily of tin (Sn) or an alloy of tin. In some embodiments, galvanic metal microstructures of the present invention are made by melt spinning, spray atomization, inert gas condensation, solution precipitation, physical vapor deposition, or electrodeposition.

Embodiments described herein provide compositions useful for generating hydrogen gas when contacted with water or water containing liquids including but not limited to gray water, urine, pond water and so forth. Aluminum based alloys can be made to generate hydrogen very rapidly by reaction with water at room temperature by forming galvanic cells. The galvanic effect continuously allows the exposure of new unoxidized metallic surface thus allowing for further hydrolysis at room temperature. The alloys may be composed of primarily aluminum and other metals including, but not limited to, tin (Sn), magnesium (Mg), silicon (Si), bismuth (Bi), lead (Pb), Gallium (Ga), Indium (In), Zinc (Zn), Carbon (C), or the like and mixtures thereof.

Certain desirable embodiments the present invention provides nanostructured aluminum-based alloys for spontaneous, facile and rapid generation of hydrogen at room or elevated temperatures without externally applied power, by reacting the composition, for example in powder form, with water and/or liquids containing water. By coupling compositions of the present invention with fuel cells or a hydrogen internal combustion engine the compositions will enable effortless generation of power to run electronic equipment, transportation vehicles, and powered mechanisms and so forth. This will be useful for various products and services for defense and civilian applications. Actuation and propulsion systems that require rapid pressurization may also be benefitted. Thus, hydrogen generation from water or water-based reactions with compositions of the present invention can replace or supplement hydrocarbon fuels.

A method of producing nanogalvanic structured aluminum based particulate material includes high energy ball milling of aluminum and other optional metals at room temperature, preferably at reduced temperatures and more preferably at cryogenic temperatures. Thus, in certain embodiments the method of the present invention includes ball milling of aluminum at temperatures below about 30° C., more preferably below about 25° C., still more preferably below about 20° C., still more preferably below about 10° C., still more preferably below about 5° C., still more preferably below about 0° C., still more preferably below about −25° C., still more preferably below about −50° C., still more preferably below about −100° C., still more preferably below about −150° C., still more preferably below about −200° C. and still more preferably below about −250° C. Milling of aluminum and aluminum alloys at reduced temperatures is capable of producing nanogalvanic alloys that can produce hydrogen very rapidly by the hydrolysis reaction with water at room temperature without an externally coupled power supply. Thus, the method of making compositions of the present invention may include cooling the metal or metallic powders from ambient temperature to cryogenic temperatures during processing of the powders. This can be achieved by cooling the milting device or milling device chamber with coolant fluids or coolant cryogens such as liquid nitrogen, liquid oxygen, liquid argon or even liquid helium.

The aluminum may be essentially pure aluminum (i.e. greater than 98 atomic percent of aluminum and preferably greater than 99 atomic percent of aluminum), an alloy of aluminum, preferably an alloy of aluminum containing greater than 90 atomic percent of aluminum, more preferably greater than 70 percent of aluminum and more still preferably greater than 50 atomic percent of aluminum, and scrap aluminum for example aluminum cans. Suggested examples of aluminum alloys include but are not limited to, Al5056 and aluminum alloys of 1000, 2000, 3000, 5000, 6000, and 7000 series. Preferably the aluminum alloy contains at least 99, 98, 95, 90, and at least 80 atomic percent aluminum. Scrap aluminum powders were used to produce scrap Al—Sn alloys that produced hydrogen when the scrap Al—Sn alloys reacted with water.

Nanogalvanic cells with aluminum as the anode can be coupled with another element acting as the cathode e.g. metals including, but not limited to, tin (Sn), magnesium (Mg), silicon (Si), bismuth (Bi), lead (Pb), gallium (Ga), indium (In), zinc (Zn), carbon (C), or the like and mixtures thereof. The galvanic couple is made by the close and intimate contact of the two dissimilar metals which have different corrosion potentials (i.e. one acting as an anode and other as a cathode). The nanogalvanic effect disrupts the oxide layer rapidly exposing new metallic surfaces and thus enhances the hydrolysis reaction at room temperature which in turn rapidly accelerates hydrogen production.

Galvanic corrosion occurs when two dissimilar metals make contact with one another in the presence of an electrolyte thereby forming a galvanic couple. The more noble metal (more cathodic on the galvanic series) provides additional surface area for the reduction reaction to occur on. This accelerates the oxidation/corrosion of the less noble metal (more anodic on the galvanic series). The extent of corrosion is greatest at the interface of the two metals, but may also occur at some distance away from the actual interface. In addition, the cell kinetics in this case are enhanced when the cathode is smaller in surface area relative to the anode.

Nanostructured nanogalvanic binary or higher order alloys consisting of aluminum (Al) metal comprising 50 to 99.9 atomic percent (at. %) as one of the constituents were processed by a non-equilibrium process. The other constituent(s) may be one or a combination of the following elements including, but not limited to: tin (Sn), magnesium (Mg), silicon (Si), bismuth (Bi), lead (Pb), gallium (Ga), indium (In), zinc (Zn), carbon (C) and mixtures thereof ranging from about 0.1 to about 50 atomic percent of the constituent(s).

The processing techniques that may be used may include but are not limited to, milling/machining (including ball milling and especially high energy ball milling), melt spinning, spray atomization, inert gas condensation, solution precipitation, physical vapor deposition, and electrodeposition. Melt spinning forms thin ribbons of material. Examples of milling apparatuses can be far ranging to include but not limited to: The SPEX Industries, Edison, N.J. series of mills or Zoz GmbH, Germany, series of mills. Relatively lower energy types include the Pulverisette planetary ball mills from Fritsch GmbH, Idar-Oberstein, Germany; the PM series of planetary ball milk from Retsch GmbH, Dusseldorf, Germany; or the attritor type mills from Union Process, Akron, Ohio, Jet Mill and Jar Mill from Glen Mills, Clifton, N.J. Relatively lower energy types of suggested milling apparatuses include the Pulverisette planetary ball mills from Fritsch. GmbH. War-Oberstein, Germany; the PM series of planetary hail mills from Retsch GmbH Dusseldorf, Germany; or the attritor type mills from Union Process, Akron, Ohio, Jet Mill and Jar Mill from Glen Mills, Clifton, N.J. To avoid cold welding and sticking to the vial and milling media, the milling process can be carried out at liquid nitrogen temperatures and/or with surfactants/additives. Suggested additives and surfactants include, but are not limited to, stearic acid, oleic acid, oleyl amine, valeric acid, octanoic acid, decanoic acid, undecanoic acid, palmitic acid, ethanol, hexane, dodecane and other long chain hydrocarbon compounds and mixtures thereof. Surfactants and additives can be utilized with the metallic powders and milling media and vials during the milling process. Desirably, the surfactant is a solid or a liquid at room temperature particularly when the milling is performed at ambient or room temperature. Desirably, the milling balls and the mixing vials are comprised of hard wear-resistant materials including, but not limited to, metals, ceramics, oxides and combinations thereof. Enhanced reaction kinetics are achieved through processing of nanostructured aluminum based galvanic alloys by high energy ball milling at cryogenic temperature. The Al-alloy powders may be produced by ball milling pure aluminum with other metals including but not limited to, tin (Sn), magnesium (Mg), silicon (Si), bismuth (Bi), lead (Pb), gallium (Ga), indium (In), zinc (Zn), carbon (C), for 0.01 to 8 hours at cryogenic temperature such as at −100° C. and −196° C. Pure aluminum may be substituted by or commercially available aluminum alloys e.g. AA5056, AA5083, etc. The individual powder particulate size can be in the range of 0.01 µm-6 mm in diameter. Additionally, the powder could be consolidated to form compacts or functional parts for tuning the hydrogen generation rate and yield. For example, powders of the present invention could be consolidated to produce a tablet, a rod, a pellet or a bulk part. Additionally, powders of the present invention would be coated on to the surface of a component or part. Suggested processes include, but are not limited to, metal injection molding, cold and hot isostatic pressing, additive manufacturing techniques including laser and non-laser techniques, thermal and cold spray and additive friction stir welding, powder forging, hot pressing, pressure less sintering, shock consolidation and field assisted sintering.

During the high-energy milling process, the metal powder may be subjected to a low or cryogenic temperatures to embrittle the constituents. In general all metals become more brittle with decrease in temperature, because their active slip systems (relating to dislocation and other thermally activated processes governing their mechanical behavior become statistically less active). The type of embrittlement is clearly demonstrated by the well-known ductile-to-brittle transition (DTBT) of ferritic steels. Low temperature processing is defined by processing that occurs at temperature ranging from just below room temperature (24° C.) down to −270° C. Low temperature ball milling here is utilized in this example to keep the powders (AA5056, Al, Sn, and Bi) cold, such that they remain as brittle as possible and thereby preventing or, more precisely, reducing and minimizing the powder from adhering to the milling media and walls of the vial. An additional benefit of low temperature milling is that certain metals or metal powders will undergo a temperature induced crystallographic transformation, also known as an allotropic transformation, from a ductile to a brittle state. For example, pure tin transforms from the silvery, ductile metallic allotrope of β-form white tin to the brittle, nonmetallic, α-form grey tin with a diamond cubic structure at a temperature that is equal to or less than 13.2° C. (286.2 K). Specifically, this brittle transformation induces advantageous milling kinetics, resulting in a favorable dispersion of Sn in Al that would otherwise not be possible and or as optimized for producing a dispersed galvanic couple (a microstructural building box required for successful hydrogen production) having reduced length scales. In this example, cryogenic temperature is typically defined as temperature below about −150° C. Liquid nitrogen, for instance, having a temperature as low as −196° C. (77K), may be supplied to provide such cooling. Liquid nitrogen milling was made possible by placing the sealed vial in a thick nylon sleeve modified to allow placement into the high energy mill as well as to allow the in-flow and out-flow of liquid nitrogen. The vial was allowed to cool to liquid nitrogen temperature before starting the mill. Mechanical alloying at liquid nitrogen temperatures in the SPEX shaker mill for approximately 4 hours was performed. After the ball milling procedure was completed, the alloyed AA5056-Sn (or Al—Sn) powder was removed from the steel vial in an Ar glove box and stored. This milling procedure resulted in a finely divided powder mass, consisting of particulates in the micron range i.e. diameters between 1 and 10,000 microns. While 4 hours of cryogenic milling was used in this example, it doesn't define the time range over which hydrogen producing powders can be synthesized. This is the same with, the milling energy, ball-to-powder ratio and/or other generic aspects of the milling process including composition.

Galvanic corrosion occurs when two dissimilar metals make contact with one another in the presence of an electrolyte thereby forming a galvanic couple. The more noble metal (more cathodic on the Galvanic Series) provides additional surface area for the reduction reaction to occur on. This accelerates the oxidation/corrosion of the less noble metal (more anodic on the Galvanic Series). The extent of corrosion is greatest at the interface of the two metals, but may also occur at some distance away from the actual interface. In addition, the cell kinetics are enhanced when the cathode is smaller in surface area relative to the anode. The smaller the size of the grains and the size of the dispersed phased, the higher is the galvanic reactivity. The cell kinetics are enhanced when the cathode is smaller in surface area relative to the anode. In general greater the difference of corrosion potential between the matrix and the dispersed phase higher is the galvanic reactivity.

A plurality of dispersed metallic particles formed of solute metal(s) in the solvent metal matrix. The dispersed solute particle reside within grains and along the grain boundaries. They typically have average diameters in the range 20-500 nm. However they could be smaller as well as larger than the given range. In addition at least some of the dispersed particles may further contain additional element(s) such as aspects of the matrix and or other advantageously included elemental species such as oxygen (O), nitrogen (N), carbon (C), sulfur (S), silicon (Si), bismuth (Bi), carbon (C), gallium (Ga), indium (In), lead (Pb) or other element(s) (i.e. from the remainder of the periodic table). Additionally, in some instances, due to processing or otherwise, the particles may comprise solute metal and some small amount of a solvent metal or alloy (such as Al).

In one embodiment, a nanogalvanic microstructure can be produced that includes providing a matrix phase material, a dispersed phase material and milling the combined phases to produce a material that spontaneously generates hydrogen when the material contacts water, urine or another water containing liquid.

Figure 3:
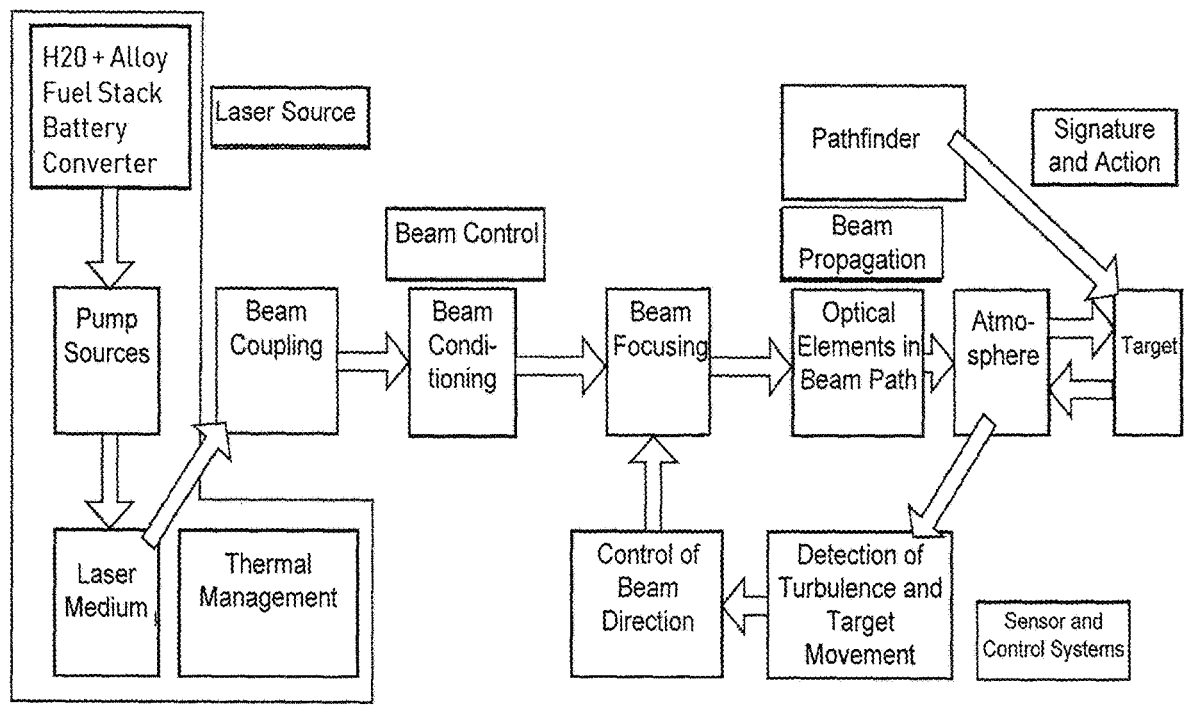
FIG. 3 shows an exemplary water powered laser gun.

FIG. 3 shows an exemplary laser weapon using the water power generator. The weapon can be large sized for aircraft use or shipboard use as a directed energy weapon, or can be miniaturized with lower power output for personal defense as a laser gun. In this case, the above water power energy supply and processing system acts on the pump sources, which use the laser medium to generate an active beam, which is then fed into the beam control unit. The beam control unit consists, for example, of beam coupling(-in) followed by beam conditioning and elements that enable alignment of the beam, for example, onto a target. The active beam then propagates over possible optical elements in the beam path and generally through the earth's atmosphere in the direction of the target, which can be marked by a pathfinder. An action by the beam is produced on the target. Sensor systems and electronic control systems can, e.g., detect turbulence in the atmosphere and movements of the target, and can reposition and/or redirect the active beam using a suitable control system. Another embodiment uses individual laser generating units connected to output stage elements using optical fibers arranged on the airborne part. Each of the output stage elements is connected to an (additional) beam coupling unit using an optical fiber or an optical free beam. The individual beam portions of the individual output stage elements are then combined in the beam coupling unit and are forwarded via an optical fiber or an additional optical free beam to a beam optics element for emitting the active beam. Various technologies may be used for data exchange, e.g. electromagnetic radio waves in the decameter to decimeter wavelength range, which propagate in the atmosphere. However, these may be detectable and, in particular, susceptible to jamming/interference, and may have a limited range and/or a limited data rate. Also possible are electromagnetic waves in the decimeter to millimeter wavelength range; however, these are practicable only with a line of sight connection between transmitter and receiver. Another option is (laser) light propagating through the atmosphere, which is subject to essentially the same limitations as electromagnetic waves. A further option is electrical signals transmitted via lines, which may also involve risk due to the conductive connection, e.g. via high-voltage towers. Particularly preferable in the scope of the invention are optical signals transmitted via optical waveguides ("optical fiber guided"), the range of which may be limited to a certain extent, but may be greater than that of electrical lines. In this case, the exchange of data via optical waveguides can be a viable compromise that will allow particularly airborne weapon systems to be equipped with such data transmission systems. In particular, it is also possible for an airborne platform, e.g. a guided missile, flying at high speed, to tow an optical waveguide over great distances, e.g. several tens of kilometers, without the waveguide becoming detached or the transmission breaking down.

According to one embodiment, an airborne laser weapon has at least one laser generating unit, at least one output stage element, a beam optics element, and a water-based power generator. The system is small enough for aircraft mounting.

In another embodiment for missile defense, high power lasers are needed. A high-powered laser of the 100 kW class, e.g. a chemical laser—COIL, may be installed on board a transport aircraft, and its generated radiation may be focused on a target by means of a beam focusing unit that projects out of the fuselage of the aircraft. The laser can be diode pumped laser, e.g. designed as a solid-state laser, wherein liquid-, gas-, or metal vapor lasers may also be used, i.e., the primary energy in the form of electrical energy may be converted to radiant energy for the optical excitation of the laser-active medium using semiconductor lasers, diode lasers.

In this case, the system can be distributed into an airborne portion and a ground portion, wherein the water generator, the beam optics element and the at least one output stage element are arranged on the fully movable part, supplemented by power from an optical fiber for energy transmission from the ground-based part to the air-based part, and particularly provides a communications connection between ground-based part and air-based part. This configuration is designed such that a system is produced in which the output beam, which is ultimately directed toward a target, can be focused within the fully encompassing half space, or at least in large portions thereof, wherein power is transmitted between the elements in which energy is converted from another energy form into optical radiant energy, and the final opto-mechanical element that is responsible for focusing the beam onto the target by means of fiber-optic elements. The components of the beam sources are separated into components that essentially codetermine mode quality and/or beam divergence, spectral properties and/or optical power. The output stage that substantially determines the output beam quality, but which is responsible for only a fraction of the total volume and the total mass of a beam source may be coupled directly to a beam focusing unit, and may be situated on the airborne platform, while it continues to be supplied via fiber-optic elements with optical radiant power, which is generated in the pump sources which, together with the assigned ancillary units such as energy supply, cooling, etc., make up the majority of the total volume and the total mass of a beam source, wherein this second part may be arranged in a ground-based part of the system, and power and optical signals may be transmitted between these two parts via fiber-optic elements.

In this way, a tactical, personal laser weapon system having relatively small dimensions, long sustainability and low costs can be provided, which is not significantly restricted in terms of its mobility and range, does not sacrifice the advantages of fiber-optic power transmission as opposed to free-beam transmission, such as robustness, reliability, independent adjustment, resistance to harsh environmental factors, flexible geometric design and low volume and mass etc., and does not require reductions in terms of mode quality and/or beam divergence, spectral properties or optical power, and therefore in the spectral radiation intensity that is available for a target, and therefore ultimately the effect that can be achieved. Moreover, operational reliability is thereby increased.

In other embodiments, the metal alloy hydrogen generator can be used to power vehicles. In one aspect, a water powered system includes an aluminum alloy source to expose a liquid to an aluminum alloy to generate hydrogen gas; a hydrogen tank to store the hydrogen gas; a fuel cell stack to receive hydrogen gas from the hydrogen gas tank and oxygen from the atmosphere, the fuel cell stack generating electricity; and an energy storage device to receive electricity.

In another aspect, a vehicle includes a liquid tank to hold water or any liquid with some water therein, such as gray water, rain water, urine, for example. The liquid contacts an aluminum galvanic alloy supplied by a tank connected to the liquid tank to dispense the liquid to the alloy, or to expose the liquid to the alloy. The resulting hydrogen is optionally stored in a hydrogen gas tank coupled to the aluminum galvanic alloy tank. On demand, a fuel cell stack can receive hydrogen gas from the hydrogen gas tank and oxygen from the atmosphere for generating electricity to power a motor electrically coupled to the fuel cell stack to rotate the wheels on the vehicle.

In another aspect, a vehicle with refillable hydrogen tank can be supplemented with a hydrogen gas generator that includes a liquid tank to hold water or any liquid with some water therein, such as gray water, rain water, urine, for example. The liquid contacts an aluminum galvanic alloy and the resulting hydrogen is stored in the vehicle's existing hydrogen gas tank as a supplement fuel source.

Advantages of the vehicle may include one or more of the following. The system offers high performance in terms of emission rate, performance, fuel efficiency, durability, size, weight, cost, safety, and comfort. The system has the potential to compete the ICE vehicle in terms of performance and all driving profiles and offers advantages like extended electric range of operation, good fuel economy, higher efficiency, sufficient onboard power, and better dynamic response. As hydrogen can be generated very quickly, a small storage battery can be used and the downsized storage battery provides multiple benefits including smaller overall size for increased passenger and cargo space in the motor vehicle, increased freedom of vehicle design allowing enhanced functionality and aesthetic appeal and lower overall weight for better motor vehicle performance.

Figure 4A:
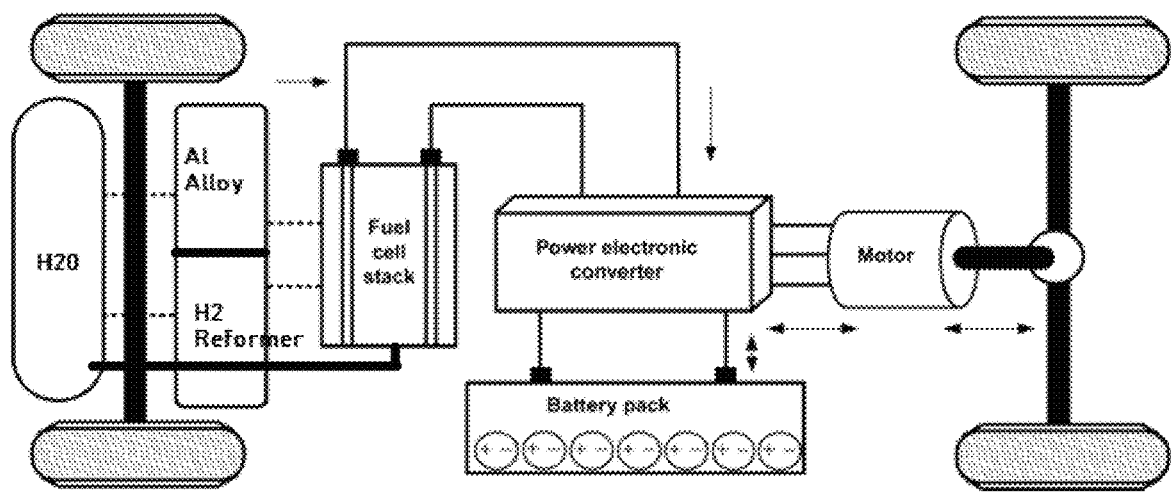
FIGS. 4A-4D show exemplary water powered vehicles and control systems.

FIG. 4A shows an exemplary water powered vehicle such as an air vehicle or a car/automobile, for example. The vehicle includes a liquid tank to hold water or any liquid with some water therein, such as gray water, rain water, urine, for example. The liquid contacts an aluminum galvanic alloy supplied by a tank connected to the liquid tank to dispense the liquid to the alloy, or to expose the liquid to the alloy. The resulting hydrogen is optionally stored in a hydrogen gas tank coupled to the aluminum galvanic alloy tank. On demand, a fuel cell stack can receive hydrogen gas from the hydrogen gas tank and oxygen from the atmosphere for generating electricity to power a motor electrically coupled to the fuel cell stack to rotate the wheels on the vehicle. Aluminum has the highest volumetric energy density among non-nuclear fuels—more than twice that of gasoline and more than five times that of methanol. If water is available, aluminum is a very desirable choice to generate power via hydrogen generation. If the total required volume of water is considered, the volumetric energy density of aluminum is 65% that of gasoline. However, when the hydrogen is used in fuel cell technology, 50% of the water can be reclaimed and utilized (i.e. removing half of the amount of water) then the energy density equals approximately that of gasoline. FCVs fueled with pure hydrogen emit no pollutants, only water and heat, while those using hydrogen-rich fuels and a reformer produce only small amounts of air pollutants. A power converter coupled to the fuel cell stack to regulate power to the motor. An energy storage device such as a supercapacitor or lithium battery, among others, can store power from the power converter. A solar panel can also be connected to the power converter. In another embodiment for distributed grid power, when the vehicle is parked, an AC converter coupled to the fuel cell stack and to an electrical grid, the AC converter controlled to provide energy to the grid on command. Liquid by-product (water) from the fuel cell stack is deposited into the liquid tank, thus completing a closed loop to minimize water waste.

Optionally, a hydrogen reformer can be used as an addition to the liquid tank to generate hydrogen gas. Fuel-cell vehicles (FCVs) can be fueled with pure hydrogen gas stored on board in high-pressure tanks. They can also be fueled with hydrogen-rich fuels including methanol, natural gas, or even gasoline; these fuels must first be converted into hydrogen gas by an onboard device called a "reformer" which may add cost, complexity, and weight to the vehicle but will make the fuel distribution easier.

Hydrogen gas is fed into a "stack" of fuel cells which consist of an anode (−) and cathode (+), separated by an electrolyte. Hydrogen is fed into the anode and the cathode is exposed to air (oxygen source). The anode causes the release of electrons from the hydrogen which travel towards the positive cathode to create an electric current. Hydrogen ions (missing an electron) are directed to the cathode via an alternate route where they regain electrons from/combine with oxygen to become water molecules. Such water is recycled in the liquid tank of FIG. 4A.

Figure 4B:
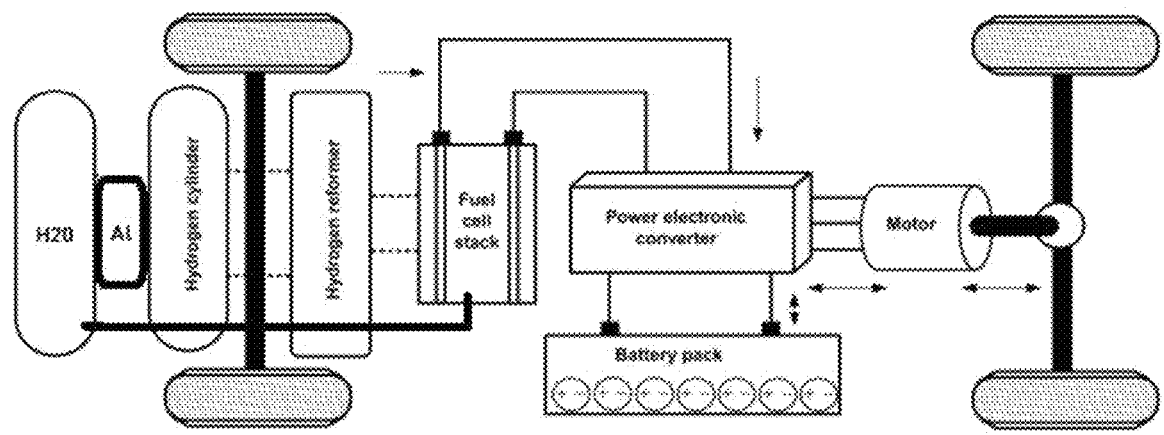

FIG. 4B shows an embodiment where the aluminum alloy is used to supplement a hydrogen vehicle that is conventionally recharged. Vehicles such as Toyota's Mirai is designed to receive hydrogen produced by powerplants and loaded like gas into the car. However, when hydrogen refueling infrastructure is not everywhere, the aluminum alloy hydrogen generator can refill the hydrogen cylinder. This method works also with reformers to convert regular gasoline into electricity as well. As shown in FIG. 1B, a hydrogen-enriched fuel can also be refined by the reformer to acquire pure hydrogen gas. This hydrogen gas is fed to fuel-cell stack where it directly meets oxygen of the atmosphere and undergoes a chemical reaction; consequently, electricity is produced. The output power of fuel-cell stack is processed by PEC to meet the power requirement of the EPS. Since the power flow from the fuel cell to propulsion unit is unidirectional, to recover the braking energy by means of regenerative braking, storage medium such as battery and ultracapacitor can be included in the system. The storage unit stores energy and supplies to propulsion system at the time of acceleration to assist the fuel cell. The integration of ICE and battery pack with fuel-cell system gives the concept of hybrid FCVs where all the configuration and advantages of HEVs can be utilized. With suitable power electronics arrangement, FCVs can also be operated as plug-in fuel-cell vehicles (PFCVs) where battery pack can be charged from grid or discharged to supply the grid.

Figure 4C:
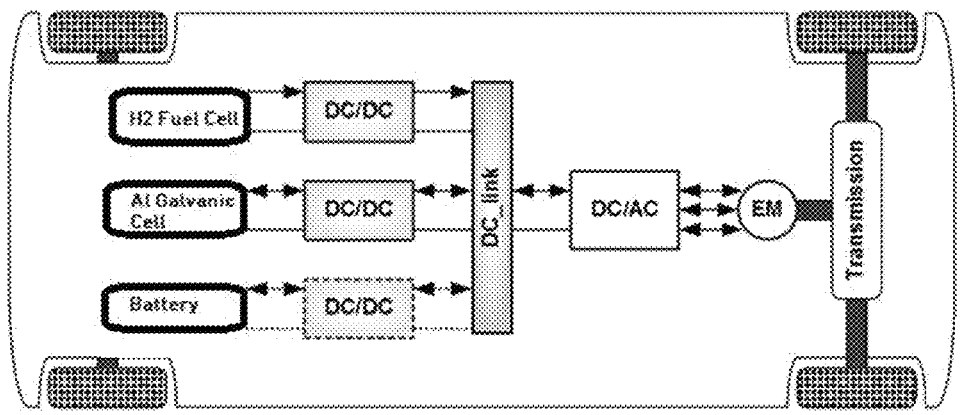

FIG. 4C shows an exemplary EV where main energy source is assisted by one or more energy storage devices including Hydrogen fuel cell, Aluminum Galvanic Fuel Cell, and Battery and/or supercapacitors. Thereby the system cost, mass, and volume can be decreased, and a significant better performance can be obtained. Two often used energy storage devices are batteries and SCS. They can be connected to the fuel cell stack in many ways. A simple configuration is to directly connect two devices in parallel, (FC/battery, FC/Aluminum, or battery/Aluminum). However, in this way the power drawn from each device cannot be controlled, but is passively determined by the impedance of the devices. The impedance depends on many parameters, e.g. temperature, state-of-charge, health, and point of operation. Each device might therefore be operated at an inappropriate condition, e.g. health and efficiency. The voltage characteristics also have to match perfectly of the two devices, and only a fraction of the range of operation of the devices can be utilized, e.g. in a fuel cell battery configuration the fuel cell must provide almost the same power all the time due to the fixed voltage of the battery, and in a battery/supercapacitor configuration only a fraction of the energy exchange capability of the supercapacitor can be used. This is again due to the nearly constant voltage of the battery. By introducing DC/DC converters one can chose the voltage variation of the devices and the power of each device can be controlled.

Figure 4D:
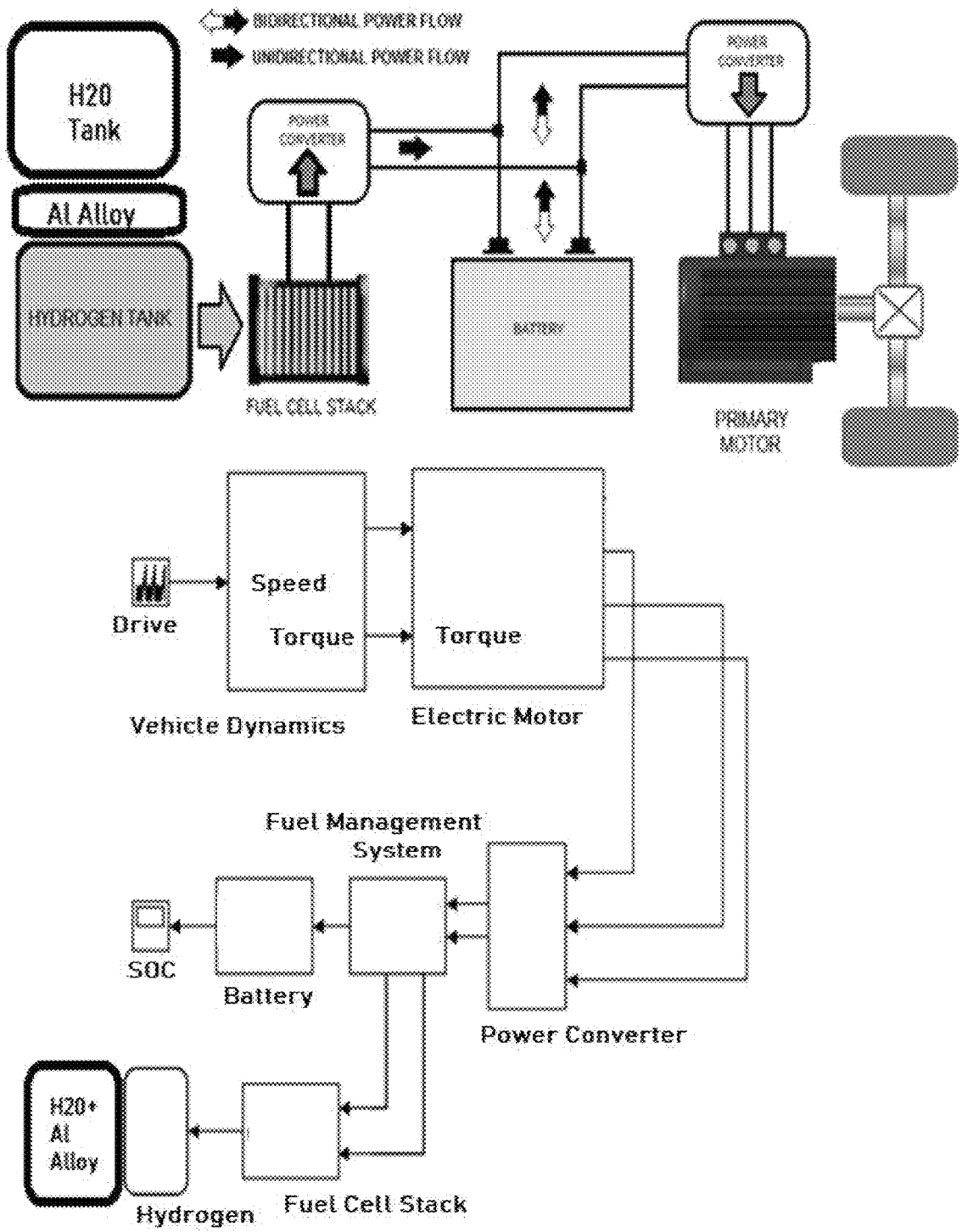

FIG. 4D shows a control system for the water vehicle. Water is applied to the aluminum alloy to generate gas which is stored in a hydrogen tank. The hydrogen is provided to a fuel cell stack to generate electricity, which is regulated by the power converter and provided to battery or energy storage device. The battery output is further regulated by a power converter and provided to a motor to drive the vehicle. The vehicle dynamics are translated to torque control signals to the motor, and the power converter is controlled to supply power to the motor. The power consumption is monitored by a fuel management system which monitors the battery with a state of charge (SOC). If the battery requires charging, the water is exposed to the aluminum allow to generate hydrogen and provided to the fuel cell stack.

An on-board hydrogen generation system might utilize most, but not all, of the metal reactant. Refueling in this case entails not only supplying more aluminum or alloy, but also the removal of the aluminum hydroxide reaction product. Thus, when the liquid is supplied to the metal container, the system separates the reaction products from the unreacted aluminum on-board the vehicle so that waste products can be discharged from the vehicle at the same time that it is refueled with fresh quantities of aluminum alloy and water.

In one embodiment, the motor vehicle includes a solar cell, which may take the form of a solar cell array or solar panel on the roof or other exposed surface of the motor vehicle. The solar cell generates free electrical energy when parked or driving outdoors and exposed to sunlight. The motor vehicle can also include a regenerative braking system of a type known in the art for generating electrical energy while slowing the motor vehicle.

The vehicle is managed by a controller such as a dedicated microprocessor or electronic control unit (ECU) operating in accordance with instructions from appropriate control software. The controller may comprise one or more processors, one or more memories and one or more network interfaces 38As should be appreciated, all of these components communicate with each other over a communication bus. The controller can be a body control module or BCM that also incorporates a human interface, a GPS, a display device and a speech processor that also communicate over the communication bus. In such an embodiment, the display device may comprise a multi-function display with touchscreen capability. The BCM controller performs a number of interior body electrically based functions including, for example, interior locking, remote key entry, interior lighting, exterior lighting, windshield wiper control and the like. In some embodiments, the BCM may also function to control entertainment functions (e.g. radio, CD player and communications such as telephone and Internet communication over a wireless network). In some embodiments the BCM is connected by a communication bus (not shown) to other control modules that provide one or more of these additional functions.

Water for the generation of hydrogen fuel for the hydrogen-powered energy source may be provided from the H2O tank or suitable water source on board the motor vehicle. As should also be appreciated, the system collects water from exhaust from a hydrogen power source of the motor vehicle or from an air conditioning system component, such as a condenser and/or an evaporator of the motor vehicle. Further, the system can refill its water tank by capturing rainwater from a rainwater collector carried on the motor vehicle. The water source may comprise an air conditioning system component of the motor vehicle such as a condenser and/or evaporator. The water source may also comprise a rainwater collector on the motor vehicle. For example, the rainwater collector may comprise (a) door seal area channels which provide gravity flow for rainwater to a collection tray, (b) a rainwater collection tray under the open cowl of the motor vehicle and/or other appropriate structure. The water source may also comprise water vapor in exhaust gases where the hydrogen-powered energy source is a hydrogen internal combustion engine. Alternatively, those exhaust gases may comprise the water vapor produced in the fuel cell where the hydrogen-powered energy source is a fuel cell. The water source may also comprise the air intake system of the motor vehicle. More specifically, cold parts or components of the air intake system collect condensation that may be collected.

FIGS. 5A-5D show exemplary flying vehicles that use the water power generator. In one aspect, a flying vehicle includes: a cab with an optional passenger seat with optional steering control; a propulsion unit having a rotating blade and an engine to rotate the blade; a rail from a cab top extending toward one external side of the cab, the cab having a moveable actuator coupled to the propulsion unit to move the propulsion unit between a first position above the cab during lift-off and a second position during lateral (forward or backward) flight. More details are disclosed in Provisional Application 62/902,541 filed Sep. 19, 2019, the content of which is incorporated by reference.

Implementations may include one or more of the following. The propulsion can be a propeller driven or jet driven unit. The engine can be electric, gas, fuel cell, or hybrid. The windshield can be an AR port, a touch screen, or combination thereof. The blades or wings can be folded. The vehicle can be stored compactly. For lift off, the blades move from a storage position to the top of cab, extends itself a predetermined height above the other vehicles, and the blades rotate to lift the unit above the other parked unit, and then moves to the side of the vehicle while retracting toward the sidewall of the vehicle for normal flight operation to allow compact storage.

FIG. 5A-5B show an exemplary flying vehicle 10 that includes a frame or cab 11 with a passenger seat 19 with optional steering control 18. Besides being used to transport passengers, vehicle 10 may be used to transport parcels which may be loaded in at an approved parcel bay by a qualified loader. For parcel transport, numerous cabins can be linked together for increased capacity. The vehicle 10 has a propulsion unit 12 having a rotating blade and an engine to rotate the blade. The vehicle includes a rail 16 from a cab top extending toward one external side of the cab. The rail or the cab has a moveable actuator coupled to the propulsion unit 12 to move the propulsion unit 12 between a first position above the cab during lift-off and a second position behind or in front of the passenger during forward flight or backward flight. A view port 14 can be provided with touchscreen capability to receive user input. The view port 14 can be a windshield with projectors to provide augmented reality. FIG. 4A shows a lift-off configuration, while FIG. 5B shows a forward thrust configuration. In either configuration, a bottom propulsion unit provides lift as needed during take-off and is turned off during forward motion to conserve energy.

The engines of the propulsion unit 12 are preferably electric motors for quiet operation, or they may be liquid fuel powered engines such as fuel cell, gasoline, jet fuel or diesel powered engines including rotary engines such as dual rotor or tri rotor engines or other high power-to-weight ratio engines. Perferably, the engines are powered using the water power generator. Alternatively, some or all of the engines of propulsion may be electric motors operated responsive to a distributed electrical system wherein battery systems are housed within each nacelle or wherein electrical power is supplied to the electric motors from a common electrical source integral to or carried by the frame. As another alternative, some or all of the engines of propulsion unit 12 may be hydraulic motors operated responsive to distributed hydraulic fluid system wherein high pressure hydraulic sources or generators are provided or a common hydraulic fluid system integral to or carried by the vehicle with cab 11.

The cab 11 includes a cockpit display device configured to display information to an onboard pilot. Cockpit display device may be configured in any suitable form, including, for example, as one or more display screens such as liquid crystal displays, light emitting diode displays and the like or any other suitable display type including, for example, a display panel or dashboard display. Audio output and input devices such as a microphone, speakers and/or an audio port enable an onboard pilot to communicate with, for example, an operator at a transportation services provider facility. Cockpit display device may also serve as a pilot input device if a touch screen display implementation is used, however, other user interface devices may alternatively be used to allow an onboard pilot to provide control commands to a vehicle being operated responsive to onboard pilot control including, for example, a control panel, mechanical control devices or other control devices. As should be apparent to those that are skilled in the art, the vehicle 10 can be operated responsive to a flight control protocol including autonomous flight control, remote flight control, onboard pilot flight control and combinations thereof.

As vehicle 10 transitions from vertical takeoff and landing mode to forward flight mode, vehicle 10 is maintained in a generally horizontal attitude for the safety and comfort of passengers, crew and/or cargo carried in cab 11. This may be achieved due to the shape and the center of gravity of cab 11 wherein aerodynamic forces and gravity tend to bias cab 11 toward the generally horizontal attitude. Alternatively, or additionally, a gear assembly, a clutch assembly or other suitably controllable rotating assembly may be utilized that allows for pilot controlled, remote controlled or autonomously controlled rotation of cab 11 relative to vehicle 10 as vehicle 10 transitions from vertical takeoff and landing mode to forward flight mode. Once vehicle 10 has completed the transition to forward flight mode, it may be desirable to adjust the center of gravity of the aircraft to improve its stability and efficiency. Once cab 11 is in the desired forward position, certain propulsion assemblies of vehicle 10 may be shut down as the thrust requirements in forward flight mode are reduced compared to the thrust requirements of vertical takeoff and landing mode. When vehicle 10 begins its approaches to the destination, inboard propulsion of vehicle 10 are reengaged to provide full propulsion capabilities and the vehicle 10 can begin its transition from forward flight mode to vertical takeoff and landing mode. During the transition from forward flight mode to vertical takeoff and landing mode, cab 11 is maintained in a generally horizontal attitude for the safety and comfort of passengers, crew and/or cargo carried in cab 11. Once vehicle 10 has completed the transition to vertical takeoff and landing mode, vehicle 10 may complete its descent to a surface and cab 11 may now lower wheel assemblies (not shown) to provide ground support to cab 11.

In one embodiment, the blade can be folded for storage, and the folding system may include, for example, a series of rapidly attachable "pitch lock" or flap lock assemblies, that together may form a flap lock system, that are easily attached to the rotor hub of the helicopter during a blade fold or unfold operation that remain in place for transport or storage, and are fully removed prior to flight after the blades have been restored to flight position. In certain embodiments, these mechanisms may be attached to the hub using quick release pins and a piston-style toggle clamping mechanism, requiring no external tools for attachment. In potential addition to the flap lock assemblies, an overhead lifting system support structure may be attached to the flap lock assemblies using similar quick-lock pins or other fasteners. This overhead lifting system support structure then attaches to a blade support beam assembly that is used to attach to a blade using an appropriate blade clamp and then used to lift or lower the main rotor blades as necessary to remove loads transmitted to the blade pins because of their static weight and other forces. More details are shown in U.S. Pat. No. 1,028,7009, the content of which is incorporated by reference. Further, when there are many other vehicles parked, when the vehicle lifts off, the blade can be extended above other vehicles during take-off, and then be retracted thereafter to save storage space.

A process for transporting the vehicle 10 performed by the flight control system of the vehicle is seen in FIG. 5C. The process includes: Upload a flight plan to the flight control system of the vehicle and get authorization (21); Lift vehicle into the air in a vertical takeoff and landing mode (22); Transition the vehicle from the vertical takeoff and landing mode to a forward flight mode (23); Transport the vehicle to the desired destination location (24); Transition vehicle from forward flight mode to vertical takeoff and landing mode (25); and Land vehicle at destination (26)

The first step involves uploading a flight plan to the flight control system of the vehicle 10 in 21. The authorization comes from a network of ground station ATCs, as detailed below. Once approved, the vehicle may then be operated responsive to autonomous flight control, remote flight control or a combination thereof. The vehicle then goes into the air in a vertical takeoff and landing mode, as indicated in block 22. During the vertical takeoff, the vehicle is preferably maintained in a generally horizontal attitude and each of the propulsion assemblies of the distributed propulsion system are independently operated using, for example, selective collective pitch and selective thrust vectoring as discussed herein. Once the vehicle has reached a desired altitude in vertical takeoff and landing mode, the next step is transitioning the vehicle from the vertical takeoff and landing mode to a forward flight mode, as indicate in block 23. Preferably, this transition involves rotating the vehicle to remain in the generally horizontal attitude. Once in forward flight mode, the next step is transporting the vehicle to the desired destination location, as indicated in block 24. Depending upon factors such as the distance of travel and environmental conditions, it may be desirable to shut down certain propulsion assemblies, as discussed herein, during forward flight. As the vehicle approaches the destination, the next step is transitioning the vehicle from the forward flight mode to the vertical takeoff and landing mode, as indicated in block 25. Preferably, this transition involves keeping the vehicle remains in the generally horizontal attitude. The next step is landing the vehicle at the destination, as indicated in block 26. This step may involve identifying a landing zone and performing an approach in the vertical takeoff and landing mode.

In one aspect, a vehicle includes: a cab with an optional passenger seat with optional steering control; a propulsion unit having a rotating blade and an engine to rotate the blade; a wing coupled to the vehicle having a folded arrangement for storage and an extended position for flight, the cab having a moveable actuator coupled to the propulsion unit to move the propulsion unit between a first position above the cab during lift-off and a second position during lateral flight.

Implementations may include one or more of the following. A pair of foldable, extensible wings are connected to each side the main body of the vehicle 10 can convert the vehicle 10 into a plane. Each wing is multiply folded so that when fully extended, the wing is at least 2 times the vehicle width, 3 times the vehicle width, 4 times the vehicle width, 5 times the vehicle width, 6 times the vehicle width, 7 times the vehicle width in one embodiment, and 10 times vehicle width in various embodiments. In operation, for deploying the vehicle 10 from a vertical state to forward flight state, wing rotates around an axis of a pivot pin for example counterclockwise until the wing is positioned perpendicular to the vehicle body and then the portions of the wing are unfolded using actuators to arrive at a fully extended position. A locking mechanism as known in the mechanical art can be used to place the foldable wings in a fully deployed position and to maintain the offset-x shaped wings during flight. In a fully deployed position each wing is arranged to be perpendicular to the vehicle body and each wing is arranged also perpendicular to its adjacent wing in one embodiment. The foldable/collapsible wings, propellers, stabilizers and flight control surfaces decrease the bulk of the vehicle during storage. The vehicle with foldable/collapsible wings, flight control surfaces, stabilizers, propellers and means to control and drive the wings, flight control surfaces, stabilizers, propellers and flight control surface can do rapid flights and rapid maneuvers/speed changes when the vehicle 10 is in a flight state. The wing can be a main wing or tail wing.

In one aspect, a vehicle includes: a cab with an optional passenger seat with optional steering control; a propulsion unit having a rotating blade and an engine to rotate the blade; a float coupled to the cab; the cab having a moveable actuator coupled to the propulsion unit to move the propulsion unit between a first position above the cab during lift-off and a second position during lateral flight.

Implementations may include one or more of the following. For amphibious operation the float can be pontoons or outrigger floats which are used to provide lateral stability so as to avoid dipping a wingtip, which can destroy an aircraft if it happens at speed, or can cause the wingtip to fill with water and sink if stationary. Other embodiments use stub wings called sponsons, mounted with their own lower surfaces nearly even with the ventral "boat-hull" shaped fuselage surface to provide the needed stability, while floatplane amphibians usually avoid the problem by dividing their buoyancy requirements between two floats, much like a catamaran.

In one aspect, a vehicle includes: a cab with an optional passenger seat with optional steering control; a propulsion unit having a rotating blade and an engine to rotate the blade; wheel(s) coupled to the cab; the cab having a moveable actuator coupled to the propulsion unit to move the propulsion unit between a first position above the cab during lift-off and a second position during lateral flight.

Implementations may include one or more of the following. In this embodiment, the wheels are motorized and can be controlled by steering wheel for short range driving if needed. While the above discussion shows architectural block diagrams of the air vehicle, the shape of the vehicle can be aerodynamically optimized.

In one aspect, a vehicle includes: a cab with an optional passenger seat with optional steering control; a propulsion unit having a rotating blade and an engine to rotate the blade; autonomous flight electronics to control the propulsion unit; the cab having a moveable actuator coupled to the propulsion unit to move the propulsion unit between a first position above the cab during lift-off and a second position during lateral flight.

Implementations may include one or more of the following. FIG. 5D shows exemplary control system for the vehicle 10. The vehicle 10 includes a flight control system 80 that may be disposed within the cab 11 that communicates with the electronics nodes of each propulsion assembly receiving sensor data from and sending flight command information to the electronics nodes, thereby individually and independently controlling and operating each propulsion assembly. The flight control system 80 receives data from various sensors such as air speed sensor 81, inertial sensor 82, radar 83, LIDAR 84, a plurality of cameras 85 positioned at various spots on the vehicle, accelerometer/gyroscope 86, and altimeter to determine height. The sensors provide orientation measurements and readings, including pitch angle, roll angle and heading of the vehicle and inertial measurements, including accelerations and angular rates of the vehicle. The control system 80 in turn drives the motors 87 with the propellers. The control system 80 also actuates the control surfaces (foldable wings, canards, etc) through actuator(s) 86. The control system receives communications from cellular, WiFi or 802.X protocol, and VHF/UHF transceivers through transceiver 87. Cellular communication can be 4G, 5G, or 6G, for example. Power for the vehicle is managed by an energy manager 88. In operation, the flight control system 80 under the control of flight control software, senses the flight control sensors and moves the control surfaces using the control surface actuators to maintain the vehicle on a desired trajectory. The vehicle can be guided via the cameras, radar, lidar, and can also be directed to coordinates using the Global Positioning System (GPS). Each vehicle 10 is configured with a unique identifier, such as a SIM card or the like. Similar to standard mobile phones, each device 10 is configured to maintain an association with a plurality of cell towers 90 based on a current geographic location. Using triangulation or other location identification techniques (GPS, GLONASS, etc.), the location, altitude, speed, and direction of each vehicle 10 can be continuously monitored and reported back to the servers to manage this data in real-time in an automated fashion to track and control all vehicles 10 in a geographic region. For example, the servers can manage and store the data in the data store.

In an embodiment, at least one vehicle may comprise various components including, but not limited to, an engine, a power source such as a battery, a memory unit, a clock, a Global Positioning System (GPS), a compass and a configuration of sensors. Specifically, the battery may provide electrical power to the various components of the at least one vehicle. In one embodiment, the configuration of sensors may comprise altimeters, accelerometers, gyroscopes, magnetometers, infrared sensors, LiDAR sensors, corona detectors, radiation detectors and so forth. According to an embodiment, the flight parameters may include at least one of a temperature of the engine of vehicle, a power consumption of the vehicle, a charging level of the battery of the vehicle, and sensor data measured by the configuration of sensors of the vehicle. In an embodiment, the plurality of flight parameters may further include Global Positioning System parameters (or GPS parameters) of the at least one vehicle. In an example, the statistical data may pertain to the GPS parameters obtained using the Global Positioning System (GPS) of the at least one vehicle. Examples of the GPS parameters include, but are not limited to, latitudinal and longitudinal coordinates of the at least one vehicle, uncertainty of estimated geo location of the at least one vehicle, and number of GPS satellites visible to the at least one vehicle for identifying the geo location thereof. In an example, the statistical data may pertain parameters and measurements of the radio communication path between the vehicle and GCS such as latency, signal strength, bandwidth, jitter and/or bit error rate. In another example, the statistical data may comprise navigation data of the at least one vehicle. Specifically, the navigation data may comprise various parameters captured through the flight duration such as compass reading, accelerometer reading, height above ground, angular velocity, angular acceleration, magnetic field and so forth.

During the flight, the ATC 89 can provide feedback such as speed, altitude, and heading, and the feedback can further include one or more of temperature, humidity, wind, and detected obstructions. The instructions, when executed, can further cause the one or more processors to: provide updates to the flying lane based on the feedback and based on feedback from other devices. The instructions, when executed, can further cause the one or more processors to based on the feedback, determine the one or more vehicles 10 at ready to descend or fly to the destination and providing authorization to the one or more vehicles 10 for a descent. The instructions, when executed, can further cause the one or more processors to—based on the feedback—detect a new obstruction and update the flying lane based on adjustments made by the one or more vehicles 10 due to the obstruction. The adjustments and/or the updated flying lane can include a buffer distance from the new obstruction. The new obstruction can be detected by the one or more vehicles 10 based on hardware thereon and communicated to the ATC.

In one aspect, a method for controlling a vehicle, the method comprising: generating a multi-dimensional model of a vehicle operating in a 3D environment; determining a hand control gesture as captured by a plurality of cameras or sensors in the vehicle, wherein a sequence of finger, palm or hand movements represents a vehicle control request; determining vehicle control options based on the model, a current state of the vehicle and the environment of the vehicle; and controlling the vehicle to operate based on the model and the 3D environment. Based on LIDAR, radar, and camera images, the system can generate 3D models for navigation purposes. The 3D models are then crowd-sourced to the cloud and a high resolution 3D map of the region above the ground is generated.

Implementations may include one or more of the following. In another aspect, a vehicle includes: a cab with an optional passenger seat with optional steering control; a propulsion unit having a rotating blade and an engine to rotate the blade; sensors to capture 3D data around the vehicle; a processor on-board the vehicle or located near a communication tower to receive sensor outputs and create a high definition 3D map; the cab having a moveable actuator coupled to the propulsion unit to move the propulsion unit between a first position above the cab during lift-off and a second position during lateral flight.

An exemplary process can fuse data for 3D models used for car navigation. Data fusion can based on sensor based detection of objects, change in weather and traffic, and holiday/emergency conditions, among others. The process checks all the sensors for change in weather (2004), detection of object (2002) and the GPS for current traffic conditions (2006). For each given sensor for detecting objects in a vehicle's environment, the process generates a 3D model of the given sensor's field of view; obstacle information from front cars using vehicle-vehicle communication (DRSC); neighboring car driver preference information; traffic information including emergency information. The process can adjust one or more characteristics of the plurality of 3D models based on the received weather information to account for an impact of the actual or expected weather conditions on one or more of the plurality of sensors. After the adjusting, aggregating, by a processor, the plurality of 3D models to generate a comprehensive 3D model; combining the comprehensive 3D model with detailed map information; and using the combined comprehensive 3D model with detailed map information to maneuver the vehicle. The process checks sensors for object detection (2008) and then checks for confirmations from other vehicles over V2V communication such as DSRC and then generates 3D model therefrom. The process can also check for weather change (2004) and correlate the weather change to generate an updated 3D model. Similarly, the process integrates traffic flow information (2006) and updates the 3D model as needed.

In one aspect, an obstacle detection system for an air space includes: one or more air vehicles each having a plurality of environmental sensors; a processor with a neural network in at least one vehicle or in at least one communication tower (edge processor) to receive sensor data and identify the obstacle in the air space from sensor outputs.

In another aspect, a method for controlling a vehicle includes generating a multi-dimensional model of a vehicle operating in a 3D environment; identifying an obstacle; determining vehicle control options based on the model, a current state of the vehicle and the environment of the vehicle; and controlling the vehicle to operate based on the model and the 3D environment. Based on LIDAR, radar, and camera images, the system can generate 3D models for navigation purposes.

Implementations may include one or more of the following. The obstacle can be detected by radar when the vehicle is in an approved lane that is not aware of the obstacle in advance. Non-limiting examples of static obstructions which are permanent include buildings, mountains, cell towers, utility lines, bridges, etc. Non-limiting examples of static obstructions which are temporary include tents, parked utility vehicles, etc. Temporary and permanent static obstructions can be managed the same with the temporary obstructions having a Time To Remove (TTR) parameter which can remove it from the database. Moving vehicles 10 are one example of dynamic obstructions. The ATC 89 can notify the vehicles 10 of other vehicles 10 and the vehicles 10 can also communicate the detection of the vehicles 10 as well as other dynamic and static obstructions to the ATC. The obstructions can include dynamic obstructions, and the characteristics comprise size, shape, speed, direction, altitude, and heading. The characteristics can be determined based on analyzing multiple images or video over time. The vehicle 10 method 1200 can further include receiving notifications from the air traffic control system related to previously detected obstructions; and updating the air traffic control system based on the detection of the previously detected obstructions. The characteristics are for an obstruction database maintained by the air traffic control system.

The vehicle's cameras, along with radar and lidar, automatically capture and classify dynamic/static obstacles encountered and classify the obstacles using neural networks (NN). The NN receives camera images along with radar/lidar data to help distinguish obstacles to avoid during the flight. One NN used is generative adversarial networks (GANs) are deep neural net architectures comprised of two nets, pitting one against the other (thus the "adversarial"). One neural network, called the generator, generates new data instances, while the other, the discriminator, evaluates them for authenticity; i.e. the discriminator decides whether each instance of data that it reviews belongs to the actual training dataset or not. The generator is creating new, synthetic images that it passes to the discriminator. It does so in the hopes that they, too, will be deemed authentic, even though they are fake. The goal of the generator is to generate passable obstacles. The goal of the discriminator is to identify images coming from the generator as obstacles. Here are the steps a GAN takes: The generator takes in random numbers and returns an image. This generated image is fed into the discriminator alongside a stream of images taken from the actual, ground-truth dataset. The discriminator takes in both real and fake images and returns probabilities, a number between 0 and 1, with 1 representing a prediction of authenticity and 0 representing fake, resulting in a double feedback loop. The discriminator is in a feedback loop with the ground truth of the images. The generator is in a feedback loop with the discriminator.

In yet another aspect, a flight obstacle detector includes: sensors including radar or lidar; a noise vector provided to a generator network to provide synthesized obstacles; camera(s) providing images; a discriminator network coupled to the camera and the generator network, the discriminator network and generator network iteratively trained to identify a flight obstacle; abstract the obstacle to a bounding box such as a pyramid (mountain), cylinder (building), rectangle (building) with parameters of each object and location and height of the obstacle; search obstacle DB based on location and parameters and if no entry matches the obstacle, then add a new entry with the abstraction along with location/height of obstacle, and an image and 360 deg video.

The systems and methods provide a mechanism in the ATC 89 to characterize detected obstructions at or near the ground. In an embodiment, the detected obstructions are dynamic obstructions, i.e., moving at or near the ground. Examples of dynamic obstructions can include, without limitation, other vehicles 10, vehicles on the ground, cranes on the ground, and the like. Generally, dynamic obstruction management includes managing other vehicles 10 at or near the ground and managing objects on the ground which are moving which could either interfere with landing or with low-flying vehicles 10. In an embodiment, the vehicles 10 are equipped to locally detect and identify dynamic obstructions for avoidance thereof and to notify the ATC 89 for management thereof to update the obstacle database.

Further, the detected obstructions can be static obstructions, i.e., not moving, which can be temporary or permanent. The ATC 89 can accurately define the location of the detected obstructions, for example, a virtual rectangle, pyramid, cylinder, etc. defined by location coordinates and altitude. The defined location can be managed and determined between the ATC 89 and the vehicles 10 as well as communicated to the vehicles 10 for flight avoidance. That is, the defined location can be a "no-fly" zone for the vehicles 10. Importantly, the defined location can be precise since it is expected that there are a significant number of obstructions at or near the ground and the vehicles 10 need to coordinate their flight to avoid these obstructions. In this manner, the systems and methods seek to minimize the no-fly zones.

Further, the present disclosure relates to obstruction detection systems and methods with air traffic control systems for vehicles 10. Specifically, the systems and methods use a framework of an air traffic control system which uses wireless (cell) networks to communicate with various vehicles 10. Through such communication, the air traffic control system receives continuous updates related to existing obstructions whether temporary or permanent, maintains a database of present obstructions, and updates the various vehicles 10 with associated obstructions in their flight plan. The systems and methods can further direct vehicles 10 to investigate, capture data, and provide such data for analysis to detect and identify obstructions for addition in the database. The systems and methods can make use of the vast data collection equipment on vehicles 10, such as cameras, radar, etc. to properly identify and classify obstructions.

Through the data capture equipment, the vehicles 10 are adapted to detect potential obstructions and detect operational data (speed, direction, altitude, heading, location, etc.). For newly detected obstacles, the vehicles 10 are adapted to transfer the operational data to the servers 92. Sensors on the vehicles 10 can capture identification data, photos, video, etc. and upload. In an embodiment, the vehicles 10 are provided advanced notification of obstructions and capable of local data processing of the identification data to verify the obstructions. If the local data processing determines an obstruction is already known, i.e., provided in a notification from the servers 92, the vehicle 10 does not require any further processing or data transfer of the identification data, i.e., this obstruction is already detected.

On the other hand, if the vehicle 10 detects a potential obstruction, i.e., one that it has not been notified of, based on the local data processing, the vehicle 10 can perform data transfer of newly identified obstruction data to the servers 92.

The servers 92 are configured to manage the obstruction DB 820, namely to update the entries therein. The servers 92 are configured to receive operational data from the vehicles 10 under control for management thereof. Specifically, the servers 92 are configured to manage the flight plans of the vehicles 10 200, and, in particular with respect to obstructions, for advanced notification of future obstructions in the flight plan.

The servers 92 are configured to receive the detection of potential obstructions. The vehicles 10 can either simply notify the servers 92 of a potential obstruction as well as provide the identification data for the servers 92 to perform identification and analysis. Upon receipt of any data from the vehicles 10 200 related to obstructions (a mere notification, actual photos, etc.), the servers 92 are configured to correlate this data with the DB 820. If the data matches an entry that exists in the DB, the servers 92 can update any information related to the obstruction such as last seen date.

If the servers 92 detect that the potential obstruction does not exist in the DB, the servers 92 add an entry in the DB, perform identification if possible from the identification data, and potentially instruct a vehicle 10 to identify in the future. For example, if the servers 92 can identify the potential obstruction from the identification data, the servers 92 can create the DB entry and populate it with the identified data. The servers 92 can analyze the identification data, as well as request human review, using pattern recognition to identify what the obstruction is, what its characteristics are (height, size, permanency, etc.). If the servers 92 do not have enough identification data, the servers 92 can instruct the identifying vehicle 10 or another vehicle 10 in proximity in the future to obtain specific identification data for the purposes of identification.

The obstructions can be stored and managed in an obstruction database (DB) communicatively coupled to the servers 92 and part of the Air traffic control system 300. Obstructions can be temporary or permanent and managed accordingly. Thus, the DB 820 can include an entry for each obstruction with location (e.g., GPS coordinates), size (height), and permanence. Temporary obstructions can be ones that are transient in nature, such as a scaffold, construction equipment, other vehicles 10 in flight, etc. Permanent obstructions can be buildings, power lines, cell towers, geographic (mountains), etc. For the permanence, each entry in the DB can either be marked as permanent or temporary with a Time to Remove (TTR). The TTR can be how long the entry remains in the DB. The permanence is determined by the servers 92 as described herein.

In one aspect, a mapping system for an air space includes: a plurality of air vehicles each having a plurality of environmental sensors; a processor in at least one vehicle or in at least one communication tower (edge processor) to receive sensor data and create a 3D model of the air space from successive air vehicle sensor outputs.

Implementations may include one or more of the following. In another exemplary system for crowd-sourcing navigation data, a crowdsourcing server is in communication with a plurality of vehicles 1 . . . n. The vehicles perform peer-to-peer discovery and crowd-sourced navigation. The system receives proximity services for a group of vehicles traveling a predetermined route using peer-to-peer discovery, receives crowdsourcing data from said plurality of vehicles, sharing crowdsourcing data to the group of vehicles (or a subsequent group of vehicles) traveling the route of interest. Such information can be used in providing navigation guidance to the vehicle traveling the route using the crowdsourced data. In one aspect, the vehicles traveling the same route can be determined using a vehicle to vehicle communication protocol that facilitate identifying peers based upon encoded signals during peer discovery in a peer to peer network. The system can be WiFi or cellular based such as the Proximity Services, among others. In one embodiment, the identification of peers based upon encoded signals during peer discovery in a peer to peer network can be done. For example, direct signaling that partitions a time-frequency resource into a number of segments can be utilized to communicate an identifier within a peer discovery interval; thus, a particular segment selected for transmission can signal a portion of the identifier, while the remainder can be signaled based upon tones communicated within the selected segment. Moreover, a subset of symbols within the resource can be reserved (e.g., unused) to enable identifying and/or correcting timing offset. Further, signaling can be effectuated over a plurality of peer discovery intervals such that partial identifiers communicated during each of the peer discovery intervals can be linked (e.g., based upon overlapping bits and/or bloom filter information). The method can include transmitting a first partial identifier during a first peer discovery interval. Also, the method can comprise transmitting a second partial identifier during a second peer discovery interval. Further, the method can include generating bloom filter information based upon the combination of the first partial identifier and the second partial identifier. Moreover, the method can comprise transmitting the bloom filter information to enable a peer to link the first partial identifier and the second partial identifier. Another embodiment communicates using LTE Direct, a device-to-device technology that enables discovering thousands of devices and their services in the proximity of ~500 m, in a privacy sensitive and battery efficient way. This allows the discovery to be "Always ON" and autonomous, without drastically affecting the device battery life. LTE Direct uses radio signals—called 'expressions'—which can be private and discreet (targeted securely for certain audiences only) or public (transmitted so that any application can receive them). Public expressions are a common language available to any application to discover each other, and this is the door to consumer utility and adoption. Public expressions exponentially expand the field of value. For example, vehicles that share same driving segments can broadcast expressions indicating their path(s). The system detects vehicles in the same segment as part of the proximity services for capturing and sharing crowd-sourced navigation data. Public expressions combine all applications—all value—into one single network, thereby expanding the utility of the system.

In one aspect, the process includes detecting the closing of a lane using the crowdsourcing data; predicting an avoidance maneuver using the crowdsourcing data; predicting a congestion with respect to a segment of the route of the at least one vehicle using the crowdsourcing data; and predicting traffic light patterns using the crowdsourcing data. Implementation can include one of the following. The system can determine the presence of obstacles in a flight lane by monitoring a pattern of vehicle avoidance of a particular location of the lane. The obstacles can be a new tower or smoke from a recent volcano eruption, among others. The vehicular avoidance information can be sent to vehicles that are planning to use that particular road section to optimize. The system can share prior vehicle's avoidance maneuver by monitoring change of vehicle direction and distance traveled at a close vicinity of a location on the route of a lead vehicle; and determining an avoidance maneuver in response to a ratio of change of vehicle direction and distance traveled being less than a predetermined threshold value. The system can determine a route based at least in part on an amount of time predicted for travelling from a starting location to a destination location of the route using the crowdsourcing data; and determining a route based at least in part on a predicted fuel consumption of the route using the crowdsourcing data. The determining information corresponding to a route of interest to at least one vehicle further can include monitoring a distance traveled by the at least one vehicle after reaching a destination, and predicting availability of parking spaces at the destination based at least in part on the distance traveled; and monitoring an amount of time traveled by the at least one vehicle after reaching a destination, and predicting availability of parking spaces at the destination based at least in part on the amount of time traveled. The determining information corresponding to a route of interest to at least one vehicle further comprises: measuring a time taken to travel a predefined percent of the route until the at least one vehicle comes to a halt at a predetermined location; and predicting an average amount of time used to find parking at the predetermined location using the time taken to travel a predefined percent of the route. The determining information corresponding to a route of interest to at least one vehicle further comprises at least one of: determining popularity of a fueling station along the route; determining type of fuel sold at the fueling station along the route; determining popularity of a business along the route; and determining popularity of a rest area along the route.

Next, a system to crowd-source the updates of precision maps with data from smart vehicles is detailed. In embodiments, crowd-sourced obstacle data can be used to update a map with precision. Obstacles can be trees, poles, new buildings, among others. Crowd-sourced information is updated into the map and annotated by time, weather and periodicity. The detected obstacle information may include a geographic location of the vehicle and a predetermined map of the lane. The computer system may determine the geographic location of the obstacle by, for example, using a laser rangefinder or light detection and ranging (LIDAR) unit to estimate a distance from the obstacle to the at least two objects near the vehicle and determining the geographic location of the obstacle using triangulation, for example. Such information is updated into the map system and marked as temporal. During use, if recent vehicles take defensive driving around the temporary obstacle, the map adds the obstacles to the map for the route guidance module. If recent vehicles drive the lane as though the obstacle does not exist, the system removes the obstacle from the map database, but keeps track of the history in case it is a periodic obstacle. The obstacle information is also reported to government agency for repair/maintenance. In another embodiment, if vehicles fly through the lane with a smooth line or curve, but abruptly brakes, the system infers that the lane has obstacles, for example, and the bad infrastructure is reported for path planning (to add more travel time, or to change the route to avoid the bad lane infrastructure if it is long. The new information is used to update a digital map that lacks the current information or that contains inaccuracies or may be incomplete. The digital map stored in the map database may be updated using the information processed by a map matching module, matched segment module, and unmatched segment module. The map matching module, once it has received obstacle location and GPS traces, processes obstacle locations and GPS traces by matching them to a lane defined in the digital map. The map matching module matches the obstacles and the GPS traces with the most likely lane positions corresponding to a viable route through the digital map by using the processor to execute a matching algorithm. In one example, the matching algorithm may be a Viterbi matching algorithm. Where the GPS traces do match a lane defined in the digital map, the matched trace to which the GPS traces match and obstacle information are sent to the matched segment module for further processing as will be described below. Where the GPS traces do not match a lane defined in the digital map, the unmatched trace to which the GPS traces are correlated with and the obstacle position information are sent to the unmatched segment module for further processing. The matched segment module and unmatched segment module both provide metadata to the map updating module. The metadata may include obstacle metadata lane geometry refinement metadata, lane closure and reopening metadata, missing intersection metadata, missing lane data and one-way correction metadata. The map updating module updates the digital map in the map database.

The process to update maps using crowd-sourced data may begin with the unmatched segment module clustering the unmatched GPS traces received from the map matching module. Many available algorithms may be suitable for this process, but in one example, an agglomerative clustering algorithm that iteratively compares GPS traces with each other and combines those that fall within a predetermined tolerance into a cluster may be used. One example of such and algorithm uses the Hausdorff distance as its distance measure in the clustering algorithm. Once the cluster is selected, the unmatched segment module may produce a single lane geometry for a cluster of unmatched GPS traces using a centerline fitting procedure in which the single lane geometry describes a new lane segment with the obstacle which is not described in the current map database. In one example, a polygonal principal curve algorithm or a Trace Clustering Algorithm (TCI) algorithm can be used. The digital map can be modified to include the new lane, including possibly new intersections in the base map and any associated pointers or indices updated.

In one aspect, an obstacle detection system for an air space includes: one or more air vehicles each having a plurality of environmental sensors; a processor with a neural network in at least one vehicle or in at least one communication tower (edge processor) to receive sensor data and avoid the obstacle in the air space from sensor outputs.

Implementations may include one or more of the following. The vehicle generally follows its planned path, which is initially a linear path from point A to point B as guided by cameras, GPS, lidar/radar and the flight computer. The linear path becomes zig-zags or other non linear paths to handle known obstacles and then the linear path is resumed as that is the shortest distance, until the vehicle 10 encounters an unexpected obstacle as detected by cameras and sensors. Based mainly on camera detection but also through lidar/radar, the system can detect new obstacles that require a workaround of the flight plan. Once the unexpected obstacle (not in the flight plan submitted for approval) is detected, the system attempts to communicate with the obstacle using vehicle-to-vehicle ("V2V") communication. If there is no reply from the unknown obstacle, the obstacle may be a large bird or a human controlled drone whose intent can't be ascertained. If so, the system provides collision avoidance by modeling potential collisions based on algorithms taking into account vehicle size, speed, direction and wind load; and wind speed and direction. The operational data can include speed, direction, altitude, heading, and location of the vehicle, and wherein the future flight plan can be determined based on the size of the vehicle 10 and the vehicle 10 speed, direction, and wind load. The process can further include providing the flying lane assignment to the vehicle 10, wherein the flying lane assignment is selected from a plurality of flying lane assignments to maximize collision-free trajectories based on the static or dynamic obstruction. The vehicle 10 performs an evasive maneuver by slowing down, reversing course, moving above or below the obstacle, or a combination thereof, and the process can further include managing ground hold time for a plurality of vehicles 10 to manage airspace, i.e., minimize ground hold time for vehicles, safely maximize flight time for all airspace users. The evasive maneuver instructions utilize six degrees of freedom in movement of the vehicle. The changes can include instructions to change direction, instructions to change flying lane(s), instruction to land and where the vehicle should target for landing, full route modification with an emphasis on route optimization while avoiding the negative impact of the conflicting vehicles, instructions to speed up or slow down, instructions to change altitude, instructions to hold position for a specific or indefinite time period, instructions to move to a safe position away from the potential collision and either hold in the air or on the ground for a specific or indefinite time period, instructions to land very quickly, instructions to land very slowly, instructions to circle, and the like. When the obstacle is safely behind the vehicle 10, then the vehicle resumes its planned path.

The unplanned obstacle can be unexpected weather or terrorist attack, for example. The changes can include instructions to change direction, instructions to change flying lane(s), instruction to land and where the drone should target for landing, full route modification with an emphasis on route optimization while avoiding the negative impact of the weather event, instructions to speed up or slow down, instructions to change altitude, instructions to hold position for a specific or indefinite time period, instructions to move to a safe position away from the weather event and either hold in the air or on the ground for a specific or indefinite time period, instructions to land very quickly, instructions to land very slowly, instructions to circle, and the like. When the obstacle is safely behind the vehicle 10, the vehicle resumes its planned path.

If the obstacle can communicate via V2V, the vehicles can collaborate in a self-organizing traffic control system by creating an ad-hoc vehicle-based network facilitated by V2V communication. In this context, V2V communication enables development of an inter-vehicle control plan ("IVCP") that can resolve a travel-priority conflict in the potential-conflict zone which, if left unresolved, could result in a collision for flying vehicles. Generally, An IVCP includes a set of travel instructions that is communicated to vehicles participating in the ad-hoc network for the particular potential-conflict zone. For example, these instructions can include a sequence by which vehicles approaching from different directions may proceed through a potential-conflict zone, the speed at which vehicles approaching a conflict zone should be traveling, the lateral/vertical profiles of the flying vehicle so that conflict may be avoided using 3D solutions, and so forth. One important aspect of the IVCP is that the instructions are tailored for the specific vehicles participating in a conflict and are also coordinated with the other vehicles participating in the conflict so as to resolve the conflict without incident. Additionally, this coordination can assist with optimizing vehicle flow through a potential-travel-priority conflict zone as a function of traffic volume, flight lane conditions, known or predicted travel routes for vehicles near the conflict zone, and/or a priority status of one or more of such vehicles.

The method for autonomous navigation with unknown obstacle handling includes: submit a flight plan handling known obstacles for approval; obtain approval and travel using approved flight lane; detect incoming unexpected obstacle using camera, lidar, radar, and other sensors; interrogate approaching obstacle with V2V communication; if no reply, take evasive action to bypass obstacle, and else select a traffic coordinator TC (the selected communication tower or a lead vehicle if there is no communication tower); TC broadcasts status as the traffic coordinator and establishes an inter-vehicle traffic control plan ("IVCP"); TC communicates IVCP to the other vehicles approaching the potential-flight-conflict zone. Optionally, TC periodically re-broadcast its identity and re-broadcast the IVCP to confirm control of the potential-conflict zone and inform any newly arrived vehicles.

In one embodiment, a V2V communications system may be designed and configured to receive signals from at least one other vehicle within the ad-hoc vehicle-based network at issue that have the same or a similar V2V communications system. These signals can include information characterizing the type of vehicle, its weight, its speed, relevant traffic and weather conditions, the manner of approach of a vehicle, direction, latitude/longitude position, and a priority status for the vehicle, among many others. A V2V communications system may also be designed and configured to provide a communications link between vehicles approaching a potential travel-priority conflict zone in order to elect a traffic coordinator (or leader), collect data, and perform analyses so as to create the IVCP, as well as to communicate the IVCP to the participating vehicles.

In an example, if the obstacle causes a discontinuity to arise with respect to the planned flight lanes of one or more vehicles in the ad-hoc network, the system takes the following steps:

1. The discontinuity is identified;
2. Limitations are identified applicable to the end user's system and the source;
3. A navigational database is accessed to determine known waypoints that can be used to remove the discontinuity;
4. Create unique waypoint and maneuver instructions specific to each vehicle; and
5. Determine real time operational restrictions, and user preference, to generate specific communications protocols to invoke a flight information message free from discontinuities for all vehicles in the adhoc network.

Solutions by the TC can use Time-Based Flow Management, or TBFM, predicts what time all the flights will get to the point in the air where they start to change travel path a predetermined time before they get there. This key point in accurately predicting the arrival enables the TC to determine the most efficient schedule to get each flight to this spot. TBFM then builds a 4-dimensional (latitude, longitude, altitude and time) trajectory for each flight. That is, it decides the exact times the vehicle needs to be at certain intermediate points along the way in order to get to its scheduled time to begin to make its path change. Controllers receive these scheduled times and guide the flights so that each vehicle reaches its intermediate points at the right time while maintaining the required separation between the vehicles (time-based metering). The TC can delay flights slightly by assigning them a slower speed or a different altitude. Time-based metering is more effective the more airspace controllers have available. Adjacent Center Metering (ACM) increases the amount of airspace and time controllers can use to maneuver aircraft to meet their scheduled times of arrival and expands the benefits of time-based metering to aircraft that are farther away from the arrival airport.

Another implementation to solve the discontinuity facing members of the adhoc network is detailed next. This implementation plans a flight path of an aircraft based on a pigeon-inspired optimization (PIO) method as follows: establish trajectory prediction model with uncertainty; initialize the route to be optimized by the pigeon-inspired algorithm according to the route information in the specified area, and initialize the parameters such as the dimension D of the search space, pigeon population, iteration number, and geomagnetic factor R in the pigeon-inspired optimization algorithm; set the speed and position of each pigeon at random, calculate the fitness value according to the fitness function, find the current optimal path, and store each parameter of the current optimal path and solve the minimization problem of costs for a particular path; apply map and compass operator to update the speed and position of each pigeon; perform landmark operations, sort all pigeons according to fitness values, lower-adapted pigeons follow the adapted pigeons and find the center of the flock (destination), all pigeons will fly directly to their destination; determine whether the maximum number of iterations is reached, and if not, repeat the operation of map and compass and landmark until the number of iterations reaches the maximum number of iterations of landmark operator. More details are in Application 20190035286, the content of which is incorporated by reference.

Once the traffic coordinator creates the IVCP and communicates to vehicles approaching a potential-travel-priority-conflict zone in the above-described steps, the vehicles can then participate in the IVCP. In one example, IVCP instructions are communicated to the vehicles participating in the ad-hoc vehicle-based network corresponding to the potential-travel-priority-conflict zone by providing each vehicle with a virtual traffic control to change speed, lateral/vertical profile of the vehicle.

There are occasions that all vehicles must yield to a priority vehicle (fire/ambulance, among others). The method includes resolving a potential vehicular travel-priority conflict by: communicating with approaching vehicles so as to collect data relevant to an incipient conflict, creating an IVCP to avoid or resolve the conflict, communicating the IVCP to the vehicles participating in the potential conflict, receiving a priority-request message from a priority vehicle proximate to the potential conflict, and transmitting a priority-granted message to the priority vehicle.

The navigation may be implemented in the IVC system with a processor in communication with a network that is generally: 1) programmed with instructions for performing steps of a method of the present disclosure; 2) capable of transmitting, receiving, and/or storing data necessary to execute such steps; and 3) capable of providing any user interface that may be needed for a user to interact with the system, including setting the system up for a vehicle priority managing session, among other things. Those skilled in the art will readily appreciate that aspects of the present disclosure can be implemented with and/or within any one or more of numerous devices, ranging from self-contained devices, such as dedicated IVC devices that are either mobile or permanently mounted to vehicles, mobile phones, smartphones, tablet computers, laptop computers, to networks each having two or more of any of these devices, among others. Fundamentally, there is no limitation on the physical construct of An IVC system, as long as it can provide one or more of the features and functionality described herein. In some embodiments, depending on specific implementation, one or more steps of method and/or any other method(s) incorporating features/functionality disclosed herein may be implemented substantially in real-time. The network can be a Cellular V2X (C-V2X) is a 3GPP standard describing a technology to achieve the V2X requirements. C-V2X is an alternative to 802.11p, the IEEE specified standard for V2V and other forms of V2X communications. An alternative to cellular V2X technology is dedicated short-range communications ("DSRC") technology. The system can also use both or any other V2V communication standards.

The IVC system may include, for example, a V2V communications system, a processor, IVC software, a physical memory, a user interface, and an optional vehicle interface. These elements can be used together, in whole or in part, to create an IVCP, communicate An IVCP to other vehicles, receive An IVCP from another vehicle, and execute the instructions supplied by the IVCP, depending on the configuration of the IVC system and the needs of the particular IVCP ad-hoc vehicle-based network under consideration. The IVC system can also optionally include an on-board location database and/or a travel-route database. The V2V communications system may be configured to transmit and receive signals communicating IVCP instructions using any one or more of a variety of protocols. For example, a V2V communications system may broadcast signals transmitting IVCP instructions periodically from a vehicle through a process known in the art as "beaconing." As part of the beaconing process, the information described above is communicated at regular intervals and throughout a given geographic area surrounding the vehicle performing the beaconing. Beaconing signals may include, for example, velocity, heading, vehicle type, acceleration (using an in-vehicle accelerometer), vehicle priority status, a network address or other network identifier for the originator, a unique beacon-signal identifier, a timestamp, a lane identifier, and/or an indication of whether the originator is currently a traffic coordinator, among others. In one specific example, beaconing can utilize a beacon packet with the following composition: ||Packet Type|Unique Packet ID|Timestamp|Unique Vehicle Address ID|Coordinates|Direction|Vertical Profile|Horizontal Profile|Speed|VTL Leaded||. These beaconing signals (e.g., packets) can be received and/or retransmitted by another IVC system similar to the originating system through a V2V system. Furthermore, beaconing signals can be used in cooperation with an onboard location database. The use of a location database with periodically repeated beaconing signals can permit an IVC system to track the location of proximate vehicles. Even further, when a location database and beaconing signals are used along with a travel-route database, An IVC system can anticipate travel-priority conflict zones because the system is informed of, at the minimum, the location and velocity of proximate vehicles in the context of known travel-routes. In some examples, this can permit An IVC system to adapt to local vehicle densities and to anticipate, and accommodate, density trends.

The V2V communications system may also or alternatively be designed and configured to transmit and receive signals using non-beaconing protocols as well, such as signals transmitted to or from another proximate vehicle directly, for example using a handshake, push, or pull protocol, among others. Or, in yet another example, the above-described signals can be communicated between vehicles using a method known in the art as "Geocasting." In this method, vehicles can communicate with other vehicles regionally proximate but out of DSRC range by using intervening vehicles as transponders that propagate the DSRC signal. Those skilled in the art will appreciate that beaconing, Geocasting, and direct transmission are but a selection of the many existing techniques that can be used in connection with the teachings of the present disclosure.

As noted above, IVC system may optionally include a vehicle interface that can interact directly with the operative functionality of the vehicle, such as in a semi-autonomous or fully autonomous vehicle or in autonomous flying methods, thereby automatically implementing the IVCP little to no input from the vehicle operator, if any. For example, upon receipt or creation of An IVCP, a vehicle interface may, through operative connections to the various vehicle systems (e.g., propulsion, steering, braking, directional signal, etc.) direct the vehicle to conform to the IVCP. A vehicle interface can also provide vehicle data and information in order to better inform an IVC system in the creation of the IVCP. For example, a vehicle interface can provide velocity, heading, vertical/lateral profile, vehicle type, acceleration (using an in-vehicle accelerometer), vehicle priority status, and other information relevant to the creation of the IVCP to a processor in the IVC system. This information can then be used by the processor in cooperation with IVC software to create an IVCP. Of course, this information may also be communicated via a V2V communications system to another vehicle, such as one that has been elected as a traffic coordinator and charged with creating the IVCP.

When two or more vehicles meet at a conflict zone, the IVC systems of the vehicles communicate with each other in order to establish an IVCP that utilizes an ad-hoc communication network usable to resolve travel-priority conflicts. In one example, the vehicles communicate with each other using DSRC that can use IEEE 802.11(p) communication protocol via DSRC-capable radios in order to receive and transmit relevant information. Other examples of methods by which vehicles can communicate include other radio-frequency communication protocols, cellular communications (including 1G-5G, etc.), Wi-Fi, Wi-Fi enabled internet, WiMAX, laser or other light-based communication or data transfer, and others, as well as combinations thereof.

A variety of inputs can be used to identify anticipated priority conflicts and establish the IVCP that is subsequently communicated to the other vehicles approaching the travel-priority conflict zone. For example, one type of input includes vehicle-specific metrics. Such metrics may include, but are not limited to, velocity of travel, vertical/lateral profile, distance from the conflict zone, vehicle weight, indicia of traffic congestion, vehicle type, vehicle priority, and direction of travel. Other types of inputs can include known travel-route features stored in a travel-route database and/or predicted travel-route features derived therefrom. Flying vehicles approaching a potential travel-conflict zone communicate with each other, using one or more of the methods and systems described above, to get commands from a designated cell tower that can provide a coordinated set of IVCP instructions to vehicles participating in the ad-hoc vehicle-based network established to avoid any real conflicts that could occur in the potential travel-priority conflict (traffic coordinator). Alternatively, the traffic coordinator can be elected from among candidates in the ad-hoc vehicle-based network based on any one or more of a number of different factors, including those factors that indicate the ability to stop safely before a conflict zone, the ability to influence the traffic flow through the conflict zone, the traffic density on the various approaches to the travel-priority conflict zone, past waiting times, and others. For example, a subset of candidates for coordinators may be identified as those leading their respective queue of vehicles on a given approach to a priority-conflict zone. In this example, these vehicles will be the first to arrive at the conflict zone, and are therefore more likely to be in communicative contact with vehicles approaching the conflict zone from other directions. This arrangement facilitates, but is not required for, V2V communication. Furthermore, those vehicles leading their respective queues can prevent the vehicles trailing them from proceeding further, thereby controlling the vehicular traffic flow if so required by the IVCP. Other factors that can be used to elect the coordinator include, for example, the ability to hover safely before entering the potential travel-priority-conflict zone, the presence of possible barriers to V2V communication, a priority status of one or more vehicles approaching the potential conflict zone, referred to herein as a "priority vehicle" (e.g., emergency-service vehicles, mass-transit vehicles, vehicles involved in a funeral procession, etc.), traffic planning policies favoring higher traffic flow in a given direction.

In one embodiment to optimize traffic flow over a geographic area containing many actual, anticipated, or potential travel priority conflicts, an intersection-based communication device/sensor can inform the IVC system by providing traffic-related information or by providing recommended route information, as supplied by a central coordinator (ground control or lead vehicle, among others). For example, either through communication methods described above (including beaconing and Geocasting, among others), or through information collected directly using techniques well known to those skilled in the art, an intersection-based communication device/sensor can gauge the degree of proximate congestion. This information can then be communicated using any communication method known to those skilled in the art, including both wired and wireless techniques, to the central coordinator. The central coordinator, having been provided with analogous information from other travel-priority conflict zones over a geographic area containing a plurality of such zones, can provide one or more intersection-based communication devices/sensors with, for example, recommended directions for some or all of associated IVCPs, which may be determined as a function of one or more priority vehicles' travel-routes, positions, and/or other information received from and/or otherwise regarding one or more priority vehicles. These recommendations can then be communicated from the intersection-based communication device/sensor to one or more IVC systems using the techniques and methods previously described. Furthermore, the central coordinator can use information collected not only to provide information to An IVC system to inform its decision making process, such as by providing a known route for a priority vehicle received from an independent entity, such as a fire-house, police station, or municipal government, but the central coordinator can also dictate instructions to IVC systems, thereby centralizing coordination of traffic flow.

The traffic coordinator (the selected communication tower or a lead vehicle if there is no communication tower) can broadcast its status as the traffic coordinator and once elected, the coordinator can establish an IVCP, as described above, and communicate it to the other vehicles approaching the potential-travel-priority-conflict zone. Optionally, the coordinator can periodically re-broadcast its identity as traffic coordinator and re-broadcast the IVCP to confirm control of the potential-conflict zone and inform any newly arrived vehicles.

Once the traffic coordinator creates the IVCP and communicates to vehicles approaching a potential-travel-priority-conflict zone in the above-described steps, the vehicles can then participate in the IVCP. In one example, IVCP instructions are communicated to the vehicles participating in the ad-hoc vehicle-based network corresponding to the potential-travel-priority-conflict zone by providing each vehicle with a virtual traffic control to change speed, lateral/vertical profile of the vehicle to establish the IVCP.

In some embodiments, IVC systems can include mechanisms that allow certain vehicles to have higher priority than other vehicles in having the right of way at intersections. This embodiment would, for example, facilitate and expedite the motion of priority vehicles through traffic in urban areas in the case of an emergency and/or in another type priority situation. To enable such a priority scheme, one or more of two mechanisms may be utilized: detection of a priority vehicle when it approaches and leaves an intersection and a priority assignment scheme. In some embodiments, prioritization may involve three or more levels of priority. For example, in one scheme, three priority levels are provided: a highest priority for emergency vehicles en route to an emergency, an intermediate priority for mass-transit vehicles carrying multiple passengers, and lowest priority for private passenger cars. In this example, the IVC system clears the route for the highest priority vehicles as quickly and efficiently as possible, overriding any normal IVCP to create a high-priority IVCP. For intermediate-priority vehicles, the IVC system may weigh the travel directions and/or lanes containing mass-transit vehicles in a manner that allows each of those travel directions and/or lanes to clear more quickly than they would if a non-priority vehicle were present in place of each mass-transit vehicle.

In order to allow for detection of a priority vehicle, upon approaching a travel-priority conflict zone, a priority vehicle may periodically broadcast a priority-request message to announce its presence and demand for priority until it receives a priority-granted message from a traffic coordinator.

The IVC system, such as an IVC system of an elected traffic coordinator, may receive a priority-request message from the priority vehicle, and, the IVC system may transmit a priority-granted message to the priority vehicle. Priority-request messages and priority-granted messages may contain substantially the same or similar information to a beaconing signal, though they may additionally or alternatively contain an indication of the priority level of the priority vehicle (e.g., emergency priority status, public transit priority status, funeral procession priority status, etc.), travel-route information for the priority vehicle, network identifiers for any current and/or past priority vehicles that have been granted priority and/or traffic coordinators that have granted priority, and/or one or more potential-conflict zone identifiers. Notably, in some embodiments, a traffic coordinator may additionally or alternatively detect the presence of the priority vehicle by analyzing beaconing signals originating from the priority vehicle, which may in some embodiments contain any of the information that may otherwise be contained in priority-request messages. After receiving a priority-granted message, the priority vehicle may be required to inform one or more other vehicles, such as a current traffic coordinator, of its departure from a given potential-conflict zone via a priority-clear message so that any vehicles proximate to the zone can resume standard IVCP operation. Priority-clear messages may contain substantially the same or similar information to a beaconing signal, though either may additionally include a potential-conflict zone identifier. In order to provide a priority-clear message, when a priority vehicle exits or is within a certain time or distance of exiting a potential-conflict zone, it may periodically broadcast a priority-clear message for a period of time, which An IVC system on the priority vehicle may determine as a function of the priority vehicle's location and/or velocity, the nature of the potential-conflict zone, and/or other similar parameters. If priority-clear messages do not reach the intended recipient(s), such as an elected traffic coordinator, the IVC system of the traffic coordinator can deduce the departure of the priority vehicle by detecting an absence of beaconing signals originating from the priority vehicle for a certain period of time (i.e., a time-out period).

In one aspect, an air control system includes a network of communication towers with ground control modules thereon; a traffic control computer; a plurality of air vehicles each providing flight plans with travel segments in advance to the traffic control computer for approval, wherein the traffic control computer shares approved flight plans to the ground control modules positioned in each travel segment for tracking the vehicle and performing local air traffic control.

Implementations may include one or more of the following. The control is hierarchical, from national to state to city to city zones. The flight plan can include flight lanes as defined below. A flight plan conflict controller can arbitrate conflicting plans whose paths collide.

The ATC can include obstacle detection system for an air space includes: one or more air vehicles each having a plurality of environmental sensors; a processor with a neural network in at least one vehicle or in at least one communication tower (edge processor) to receive sensor data and identify the obstacle in the air space from sensor outputs.

The ATC 89 can be part of the flight control in the vehicle, and also can be external operated by the local ground control station (GCS), or a combination of internal and external ATC 89 for redundancy in coverage. The ATC 89 can be tiered where control can be done at the cell level, city level, state level, or national level, among others. One of the cellular towers can be the local ground control station communicably coupled to the at least one vehicle. Specifically, the GCS may include communication means (such as a transceiver) to communicate with the vehicle via a network, such as radio network. Optionally, the network may be a bidirectional network to facilitate two-way communication therethrough. In another embodiment, the GCS may be a mobile device (such as a remote-control device) communicably coupled to the at least one vehicle. According to an embodiment, the GCS may include equipment such as processors, memory, display screens, and so forth.

In an embodiment, operation of the at least one vehicle may be controlled completely autonomously using on-board computers. In another embodiment, operation of the at least one vehicle may be controlled at least partially by the Ground Control Station. In such embodiment, a human operator at the GCS may operate the at least one vehicle. In the external ATC 89 GCS embodiment, the vehicle 10 flies from cell to cell and receives navigation assistance/command from one of the cell towers designated as a controller. The controller communicates with one server 92. In one example, exemplary three cell towers provide associated cell coverage areas for describing location determination of the vehicle 10. Typically, for a cell site, in rural locations, the coverage areas can be about 5 miles in radius whereas, in urban locations, the coverage areas can be about 0.5 to 2 miles in radius. One aspect of the ATC 89 is to maintain a precise location at all time of the vehicles. This can be accomplished in a plurality of ways, including a combination of techniques such as triangulation based on the multiple cell towers, location identifiers from GPS/GLONASS transmitted over the cell network from vehicles, sensors in the vehicle 10 for determining altitude, speed, etc., and the like.

Server 92 is distributed and shares information on each cell. The maintained data can include current battery and/or fuel status for each of the plurality of vehicles 10, and wherein the processing for the delivery application authorization and management can include checking the current battery and/or fuel status to ensure the sufficiency to provide a current delivery, for each of the plurality of vehicles 10. The maintained data can include photographs and/or video of a delivery location, and wherein the processing for the delivery application authorization and management can include checking the delivery location is clear for landing and/or dropping a package, for each of the plurality of vehicles 10. The maintained data can include photographs and/or video of a delivery location, and wherein the processing for the delivery application authorization and management comprises, for each of the plurality of vehicles 10, checking the delivery location for a delivery technique including one of landing, dropping via a tether, dropping to a doorstep, dropping to a mailbox, dropping to a porch, and dropping to a garage. The plurality of vehicles 10 can be configured to constrain flight based on coverage of the plurality of cell towers. The constrained flight can include one or more of pre-configuring the plurality of vehicles 10 to operate only where the coverage exists, monitoring cell signal strength by the plurality of vehicles 10 and adjusting flight based therein, and a combination thereof.

The server 92 can act as the ATC. One function performed by the ATC 89 is separation assurance through altitude and flying lane coordination in addition to the aforementioned air traffic control functions, package delivery authorization and management, landing authorization and management, etc. As the ATC 89 has monitored data from various vehicles 10, the ATC 89 can keep track of specific flight plans as well as cause changes in real time to ensure specific altitude and vector headings, i.e., a flight lane. For example, the ATC 89 can include a specific geography of interest, and there can be adjacent ATCs that communicate to one another and share some overlap in the geography for handoffs. The ATC 89 can make assumptions on future flight behavior based on the current data and then direct vehicles 10 based thereon. The ATC 89 can also communicate with commercial aviation air traffic control systems for limited data exchange to ensure the vehicles 10 does not interfere with commercial aircraft or fly in no-fly zones. The server's method of communicating flight data between a plurality of systems can include receiving data indicative of flight objects. Flight information is extracted from the flight objects and rendered for viewing and editing along with real time airspace environment data pertaining to the flight information. Modifications to the flight information are received and updates to the flight objects are generated. Messages representative of the updated flight objects are generated that are compatible with subscriber systems. The generated messages are communicated to the subscriber systems across the one or more networks.

The systems and methods provide a hierarchical monitoring approach where zones or geographic regions of coverage are aggregated into a consolidated view for monitoring and control. The zones or geographic regions can provide local monitoring and control while the consolidated view can provide national monitoring and control in addition to local monitoring and control through a drill-down process. A consolidated server can aggregate data from various sources of control for zones or geographic regions. From this consolidated server, monitoring and control can be performed for any vehicle 10 communicatively coupled to a wireless network.

In one embodiment, a national level server 92 runs code to: communicate with a plurality of local servers each configured to communicate with a plurality of vehicles 10 in a geographic or zone coverage; consolidate data from the plurality of local servers to provide a summary of successively larger geography having a plurality of geographic or zone coverages; provide the summary data via a Graphical User Interface (GUI); and perform one or more functions via the GUI for air traffic control and monitoring at an individual vehicle 10 level or group level as desired.

The geographic boundary can be based on zip codes, county or township boundaries, geometric shapes, etc. The process 2300 can include coordinating the data and analyzing between servers which manage adjacent regions. The process 2300 can include determining a plurality of flying lanes including lanes which are fully within a single geographic region and lanes which traverse a plurality of geographic regions; and routing the one or more vehicles 10 in corresponding flying lanes. The process can include handing off control of specific vehicles 10 between servers based on transit in the lanes which traverse a plurality of geographic regions. The one or more vehicles 10 are routed to corresponding flying lanes to maximize collision-free trajectories based on static obstructions, minimize travel time, and manage congestion in the geographic region. The process can include receiving flight data from the one or more vehicles 10; and updating air traffic, congestion, and obstructions based on the flight data. The one or more vehicles 10 each can include an antenna communicatively coupled to the one or more wireless networks, and wherein the flight is constrained based on the antenna monitoring cell signal strength during the flight and adjusting the flight based therein whenever the cell signal strength is lost or degraded.

In a further embodiment, a drone air traffic control system includes a processor and a network interface communicatively coupled to one another; and memory storing instructions that, when executed, cause the processor to: communicate to one or more Unmanned Aerial Vehicles (vehicles 10) via one or more wireless networks to manage vehicle 10 flight in a geographic region of a plurality of geographic regions, wherein the air traffic control system has one or more servers configured to manage each geographic region which is predetermined based on a geographic boundary, wherein the one or more vehicles 10 are configured to maintain their flight in the plurality of geographic regions based on coverage or connectivity to the one or more wireless networks; obtain data related to the one or more vehicles 10, wherein the data includes flight operational data, flight plan data, and sensor data related to obstructions and other vehicles 10; analyze and storing the data for each geographic region; and manage flight of the one or more vehicles 10 in corresponding geographic regions based on the data.

In one aspect, a flight management system includes: a flight planning system that defines a trip as composed of one or more waypoints connected by one or more flight lanes, and wherein each vehicle has a plurality of environmental sensors; a processor with a neural network in at least one vehicle or in at least one communication tower (edge processor) to receive sensor data and to monitor vehicle passage through planned waypoint(s).

In another aspect, a flight management system for an air space includes: a map system that divides air space into layers of grids, each grid supporting a lane of air travel for one or more air vehicles; a processor with a neural network in at least one vehicle or in at least one communication tower (edge processor) to receive sensor data and to center the vehicle in the lane from sensor outputs, and further to navigate all waypoints in a flight plan.

Implementations may include one or more of the following. A waypoint is a reference point in physical space used for purposes of navigation for vehicles 10. Waypoints on mapping programs provide a convenient mechanism to show location, start and end points, etc. The plurality of waypoints each includes a latitude and longitude coordinate defining a point about which an area is defined for covering a portion of the geographic region. The size of the area can be based on whether the area covers an urban region, a suburban region, and a rural region in the geographic area, wherein the size is smaller for the urban region than for the suburban region and the rural region, and wherein the size is smaller for the suburban region than for the rural region. Each of the plurality of waypoints can include an altitude range set based on flight altitudes of the plurality of vehicles 10.

The waypoints can be used to provide operators and pilots visual information related to one or more vehicles 10. The waypoints can also be managed by the ATC 89 which uses one or more wireless networks and by associated vehicles 10 in communication with the air traffic control system. The waypoints can be defined based on the geography, e.g., different sizes for dense urban areas, suburban metro areas, and rural areas. The ATC 89 can maintain a status of each waypoint, e.g., clear, obstructed, or unknown. The status can be continually updated and managed with the vehicles 10 and used for routing the vehicles 10.

In an embodiment, the ATC uses a plurality of waypoints to manage air traffic in a geographic region. Again, waypoints are sets of coordinates that identify a point in physical space. The waypoints can include longitude and latitude as well as an altitude. For example, waypoints can be defined over some area, for example, a square, rectangle, hexagon, or some other geometric shape, covering some amount of area. The waypoints can cover a set area, such as every foot to hundred feet or some other distance. In an embodiment, waypoints can be set between 1' to 50' in dense urban regions, between 1' to 100' in metropolitan or suburban regions, and between 1' to 1000' in rural regions. Waypoints can also include an altitude. For UAV flights generally constrained to several hundred feet, the waypoints can either altitude or segment the altitude in a similar manner as the area. For example, the altitude can be separated in 100' increments, etc. Accordingly, the defined waypoints can blanket an entire geographic region for management. The waypoints can be detected by the vehicles 10 using location identification components such as GPS. A typical GPS receiver can locate a waypoint with an accuracy of three meters or better when used with land-based assisting technologies such as the Wide Area Augmentation System (WAAS).

The flight plan includes defining the flight paths based on specifying two or more waypoints of the plurality of waypoints. A flight path can be defined by one of specifying a start waypoint and an end waypoint and allowing a vehicle 10 to determine a path therebetween locally; and specifying a start waypoint and an end waypoint and a plurality of intermediate waypoints between the start waypoint and the end waypoint. The waypoint management method can score for the plurality of waypoints to determine the reliability and accuracy of the updates. The ATC 89 can include an obstruction database comprising a data structure for each of the plurality of waypoints defining a unique identifier of a location and the obstruction status, and wherein the obstruction status comprises one of clear, obstructed, and unknown. The waypoint management can update the obstruction status for each of the plurality of waypoints in the obstruction database based on the received updates.

The ATC 89 and the vehicles 10 can use the waypoints for various purposes including i) flight path definition, ii) start and end point definition, iii) tracking of vehicles 10 in flight, iv) measuring the reliability and accuracy of information from particular vehicles 10, v) visualizations of vehicle 10 flight, and the like. For flight path definition, the waypoints can be a collection of points defining how a particular vehicle 10 should fly. In an embodiment, the flight path can be defined with waypoints across the entire flight path. In another embodiment, the flight path can be defined by various marker waypoints allowing the particular vehicle 10 the opportunity to determine flight paths between the marker waypoints locally. In a further embodiment, the flight path is defined solely by the start and end waypoints, and the vehicle 10 locally determines the flight path based thereon.

The intermediate waypoints are monitored and used to manage the vehicle 10 in flight. In an embodiment, the vehicle 10 can provide updates to the ATC 89 based on obstruction detection as described herein. These updates can be used to update the status of the waypoint directory in the DB. The ATC 89 can use the waypoints as a mechanism to track the vehicles 10. This can include waypoint rules such as no vehicle 10 can be in a certain proximity to another vehicle 10 based on the waypoints, speed, and direction. This can include proactive notifications based on the current waypoint, speed, and direction, and the like.

In an embodiment, waypoints can be used for measuring the reliability and accuracy of information from particular vehicles 10. Again, the waypoints provide a mechanism to define the geography. The Air traffic control system 300 is configured to receive updates from vehicles 10 about the waypoints. The ATC 89 can determine the reliability and accuracy of the updates based on crowd-sourcing the updates. Specifically, the Air traffic control system 300 can receive an update which either confirms the current status or changes the current status. For example, assume a waypoint is currently clear, and an update is provided which says the waypoint is clear, then this vehicle 10 providing the update is likely accurate. Conversely, assume a waypoint is currently clear, and an update is provided which says the waypoint is now obstructed, but a short time later, another update from another vehicle 10 says the waypoint is clear, this may reflect inaccurate information. Based on comparisons between vehicles 10 and their associated waypoint updates, scoring can occur for the vehicles 10 to determine reliability and accuracy. This is useful for the ATC 89 to implement status update changes—preference may be given to vehicles 10 with higher priority.

In another embodiment, an Air Traffic Control (ATC) system for Aerial Vehicles 10 includes a network interface and one or more processors communicatively coupled to one another, wherein the network interface is communicatively coupled to a plurality of vehicles 10 via one or more wireless networks; and memory storing instructions that, when executed, cause the one or more processors to communicate with a plurality of vehicles 10 via one or more wireless networks comprising at least one cellular network; receive updates related to an obstruction status of each of a plurality of waypoints from the plurality of vehicles 10, wherein the plurality of waypoints are defined over a geographic region under control of the ATC 89 system; and manage flight paths, landing, and take-off of the plurality of vehicles 10 in the geographic region based on the obstruction status of each of the plurality of waypoints.

In a further embodiment, a non-transitory computer-readable medium comprising instructions that, when executed, cause one or more processors to perform steps of communicating with a plurality of vehicles 10 via one or more wireless networks comprising at least one cellular network; receiving updates related to an obstruction status of each of a plurality of waypoints from the plurality of vehicles 10, wherein the plurality of waypoints are defined over a geographic region under control of the ATC 89 system; and managing flight paths, landing, and take-off of the plurality of vehicles 10 in the geographic region based on the obstruction status of each of the plurality of waypoints.

In one aspect, an airway management system for an air space includes: a map system that divides air space into layers of grids, each grid supporting an airway of air travel for one or more air vehicles each having a plurality of environmental sensors; a processor with a neural network in at least one vehicle or in at least one communication tower (edge processor) to receive sensor data and to center the vehicle in the airway from sensor outputs.

Implementations may include one or more of the following. Each airway can be registered to landmarks on a physical map for recognition and correlation. For example, 3D airspace maps from 3Dairspace.org can be used. Google Earth is loaded on your computer, you only need to double-click to launch the map inside Google Earth and see airspace classifications in 2D or 3D. The system can use the FAA's geoTIFF files of its sectional charts. Inserting the geoTIFF into a CAD program can provide the exact position position of a project on the sectional chart with the FAA file containing the geoTIFF, an HTML help file, and a TFW positioning file.

The vehicle 10 can use data from camera and lidar/radar to center itself in the assigned airway. The airway is specified in 3D coordinates as a series of vectors that the vehicle 10 can follow. Airways are geographical paths for flight and are created, managed, and assigned by the ATC 89. In an embodiment, the airway are based on Federal Aviation Administration (FAA) input, policies, and standards. The airway are dynamically managed and modified based on the FAA input, other air traffic, weather, obstructions, and the like. The ATC 89 can be configured to route vehicles 10 to and from airway including based on dynamically changing airway, and to keep lateral separations between vehicles operating in the same airway or at the same altitude and in the same proximity or geography, and with collision avoidance through ATC 89 over wireless networks.

In another embodiment, multiple ATC 89 systems can manage vehicles 10 over a geographic region with existing wireless networks providing connectivity to the vehicles 10. For example, the boundaries can be based on Zip code boundaries or some other existing boundary. The multiple ATC 89 systems can manage vehicles 10 in their region based on these boundaries, coordinate vehicle 10 traffic between regions, provide redundant coverage for adjacent regions, etc. Also, with the boundaries, the ATC 89 systems can develop, manage, and integrate airway with the boundaries.

For lateral separations between vehicles operating in the same airway or at the same altitude and in the same proximity or geography, the distance between vehicles 10 is standardized and set based on the purpose of a particular flying airway. For example, the airway may be an entry and exit airway allowing for vehicles 10 taking off to enter the ATC 89, an intermediate airway that allows for some speed but also puts vehicles 10 in a position to move into an entry/exit airway, a high-speed airway (express) at a higher altitude allowing for vehicles 10 to quickly reach their destination, and the like.

In an embodiment, standard distances between vehicles 10 may be closer in lower altitude/entry and exit airways where vehicle 10 speeds may be lower than higher altitude airways. Standard distances between vehicles 10 may be further in high altitude airways due to increased speed of the vehicles 10 and allow for more time for speed and course corrections and to avoid collisions.

The distance between vehicles 10 can be changed at any time and new instructions sent to vehicles 10, from the ATC 89 via the wireless networks 302, 304, to require speed changes or to hold position. The new instructions can be based on changes in weather and more specifically storms and rain, changes in wind speed and dealing with imprecise wind speed forecasts that impact drone speed and fuel usage (battery, gas), obstructions entering or expected to enter the flying airway(s), a vehicle 10 experiencing a problem such as limited battery power or fuel left, temporary flight restrictions that may include restricted airspace, and the like.

The lateral separation accounts for vehicles 10 entering and leaving airway to account for the required takeoff, landing, and possible hovering or delivery of products by vehicles 10 that must exit airway to achieve their objectives. All communications to and from vehicles 10 occur over the wireless networks to and from the ATC 89 and/or backup ATC centers. The airspeed for vehicles 10 can be measured and/or authorized in knots and/or miles per hour (mph) within and outside of the airway to achieve appropriate lateral separations within the airway. The objective of these procedures is to ensure safe and efficient drone flights in the United States airspace.

The plurality of airways can include airways for entry and exit allowing the one or more vehicles 10 to take off or land, airways for intermediate flight which are positioned adjacent to the airways for entry and exit, and airways for high speed at a higher altitude than the airways for intermediate flight. Distances between vehicles 10 can be set closer in the airways for entry and exit than in the airways for intermediate flight than in the airways for high speed. The new instruction can be based on a change in weather comprising storms or rain. The new instruction can be based on a change in wind speed and based on wind speed forecasts and associated impact on one or more vehicles 10 and their fuel usage. The new instruction can be based on obstructions entering or expected to enter the flying airway.

In another embodiment, an air traffic control system includes one or more servers each comprising a network interface, a processor, and memory; and a database communicatively coupled to the one or more servers, wherein the network interface in each of the one or more servers is communicatively coupled to one or more vehicles via a plurality of wireless networks at least one of which comprises a cellular network, wherein a plurality of airway are defined and standardized in the geographic region each based on a specific purpose, and wherein the one or more servers are configured to communicate to the one or more vehicles 10 over the one or more wireless networks; determine an associated airway of the plurality of airway for each of the one or more vehicles 10; communicate the associated airway to the one or more vehicles 10 over the one or more wireless networks; receive feedback from the one or more vehicles 10 via one or more wireless networks during flight in the associated flying airway; and provide a new instruction to the one or more vehicles 10 based on the feedback.

Navigation methods can receive an associated airway of the plurality of airway from the air traffic control system over the one or more wireless networks; provide feedback to the air traffic control system via the one or more wireless networks during flight in the associated flying airway; receive a new instruction from the air traffic control system based on the feedback; and implement the new instruction.

In one aspect, a neural network is trained to generate flight plans from historical data. In another aspect, a vehicle includes: one or more air vehicles each having a plurality of environmental sensors; a processor with a neural network in at least one vehicle or in at least one communication tower (edge processor) to receive sensor data and follow a pre-approved flight plan based from sensor outputs.

Implementations may include one or more of the following.

Flight planning is the process of producing a flight plan to describe a proposed aircraft flight. It involves two safety-critical aspects: fuel calculation, to ensure that the aircraft can safely reach the destination, and compliance with air traffic control requirements, to minimize the risk of midair collision. In addition, flight planners normally wish to minimize flight cost through appropriate choice of route, height, and speed, and by loading the minimum necessary fuel on board. Air Traffic Services (ATS) use the completed flight plan for separation of aircraft in air traffic management services, including tracking and finding lost aircraft, during search and rescue (SAR) missions.

In one implementation, historical flight data, along with air traffic controller instructions are provided to a deep learning network, which after training, predicts the flight path based on history. The system predicts flown route based on direct-to and heading instructions as the training data follow reality that controllers like to minimize the number of instructions to pilots. The future trajectory of the vehicle is modeled as a sequence of 4D coordinates that are correlated with its realized trajectory, last filed flight plan, which is a sequence of 2D waypoints, and weather conditions in the vicinity. One implementation is designed as a "sequence to sequence learning" problem, in which the input sequence is the flight plan and the output is the actual flight trajectory. The sequential learning problem is solved by an encoder-decoder recurrent neural network structure, where the encoder learns from the flight plan and the decoder integrates the weather information and recursively "translates" the embedded flight plan information into a full 4D trajectory. Convolution layers can be used into the decoder network pipeline to extract representations from the high-dimension weather features.

A neural network examines flight data and is trained to generate one or more flight plan for a single flight. The system can generate an electronic plan for air traffic control and a plan for direct download into an onboard flight management system. The flight planning system is to calculate how much energy (battery or gas) is needed in the air navigation process by an aircraft when flying from an origin to a destination. The vehicle must also carry some reserve fuel to allow for unforeseen circumstances, such as an inaccurate weather forecast, or ATC traffic control requiring an aircraft to fly at a lower-than-optimal altitude due to congestion, or the addition of last-minute passengers whose weight was not accounted for when the flight plan was prepared. There is often more than one possible route between two airports. Subject to safety requirements, costs are minimized by appropriate choice of route, speed, and height.

Vehicles fly on airways under the direction of air traffic control. An airway has no physical existence, but can be thought of as a motorway in the sky. On an ordinary motorway, cars use different airways to avoid collisions, while on an airway, aircraft fly at different flight levels to avoid collisions. One can often see planes passing directly above or below one's own. Charts showing airways are published and are usually updated every 4 weeks, coinciding with the AIRAC cycle. AIRAC (Aeronautical Information Regulation and Control) occurs every fourth Thursday, when every country publishes its changes, which are usually to airways. Each airway starts and finishes at a waypoint, and may contain some intermediate waypoints as well. Waypoints use five letters (e.g., PILOX), and those that double as non-directional beacons use three or two (TNN, WK). Airways may cross or join at a waypoint, so an aircraft can change from one airway to another at such points. A complete route between airports often uses several airways. Where there is no suitable airway between two waypoints, and using airways would result in a somewhat roundabout route, air traffic control may allow a direct waypoint-to-waypoint routing, which does not use an airway (often abbreviated in flight plans as "DCT"). Most waypoints are classified as compulsory reporting points; that is, the onboard flight management system reports the aircraft's position to air traffic control as the aircraft passes a waypoint. Two main types of waypoints can be used: a named waypoint appears on aviation charts with a known latitude and longitude; and a geographic waypoint is a temporary position used in a flight plan, usually in an area where there are no named waypoints (e.g., most oceans in the Southern Hemisphere). The geographic waypoints have latitudes and longitudes that are a whole number of degrees. Complete routes are determined using airway(s) from origin to destination. Most flights over land fall into this category. Airway(s) from origin to an ocean edge, then an ocean track, then airway(s) from ocean edge to destination. Most flights over northern oceans fall into this category. Airway(s) from origin to an ocean edge, then a free-flight area across an ocean, then airway(s) from ocean edge to destination. Most flights over southern oceans fall into this category. Free-flight area from origin to destination can be done, air traffic control still requires a position report about once an hour. Flight planning systems organize this by inserting geographic waypoints at suitable intervals. The particular route to be flown determines the ground distance to cover, while winds on that route determine the air distance to be flown. Each inter-waypoint portion of an airway may have different rules as to which flight levels may be used. Total aircraft weight at any point determines the highest flight level which can be used. Cruising at a higher flight level generally requires less fuel than at a lower flight level, but extra climb fuel may be needed to get up to the higher flight level (it is this extra climb fuel and the different fuel consumption rate that cause discontinuities). The neural network determines a least-cost flight based only on time; fuel, fuel/time, or fuel costs and time costs and overflight charges. Despite all the effort taken to optimize flight plans, there are certain circumstances in which it is advantageous to file suboptimal plans. In busy airspace with a number of competing vehicles, the optimum routes and preferred altitudes may be oversubscribed. This problem can be worse in busy periods, such as when everyone wants to arrive as soon as it opens for the day. If all the aircraft file optimal flight plans then to avoid overloading, air traffic control may refuse permission for some of the flight plans or delay the allocated takeoff slots. To avoid this a suboptimal flight plan can be filed, asking for an inefficiently low altitude or a longer, less congested route.

The system automatically generates flight plans, secondary, or alternate flight plans, where the generated flight plans are free of obstacles or discontinuities. If obstacles, weather, or other vehicle's plans conflict with the present plan (discontinuity) exist, the discontinuities are automatically removed and a discontinuity-free flight plan is generated. In an example, if a discontinuity is identified the efficiency and operational flight object system is configured to perform the following steps: 1. The discontinuity is identified in the flight plan; 2. Limitations are identified applicable to the end user's system and the source; 3. A navigational database is accessed to determine known waypoints that can be used to remove the discontinuity; 4. Create unique waypoint and maneuver instructions specific to each vehicle; and 5. Determine real time operational restrictions, and user preference, to generate specific communications protocols to invoke a flight information message free from discontinuities for the user.

Additionally, a revision of a flight plan includes deleting or adding waypoints, modifying the position of waypoints, or modifying the characteristics pertaining to the waypoints or legs between waypoints, such as the manner in which the aircraft maneuvers, aircraft speed, time of arrival at the waypoint, or altitude. The characteristics for various waypoints or legs, segments joined by waypoints or fixes, further examples include weather bands. A weather band is a collection of environmental information for a specific or series of spatial points, such as a specific altitude or a series of three- or four-dimensional points in space and time. Starting from a line from origin to destination, the deviation includes flying over, under, or around the obstacles in 3D space and time (the 4th dimension).

Once approved, the system can generate graphical depictions such as a depiction of a lateral profile of a flight plan, a vertical profile of a flight plan, and a speed profile associated with the lateral portion of the flight plan. Graphical depictions of an active flight plan and actual flight information can be done in conjunction with multiple flight plans, flight histories, and real time flight information. The UI highlights or annunciates specific flight information history such as past flight plans specific to that aircraft or flight, or flight information from any flight may be applied for comparison. Any flight, and its flight information, may be used for comparison as long as at least one flight information parameter can be correlated to the current flight selection. The correlation parameters can be manually selected or automated. Automation is the preferred method to detect the flights and flight information that is of closet match. For example, the options can be configured by similar flight route, portion of a flight route, speeds, altitude, aircraft type, date range, origin, destination, departure time, arrival time, tail number, pilot's name, or flight number. In one illustrative example, a flight plan includes an estimated time to reach a waypoint. When the aircraft actually crosses the waypoint, the event is captured by cell towers on the ground to determine the actual crossing time and send a message including the actual crossing time to the server. The actual crossing time can be displayed and recorded automatically on the user's computing device by mobile application, and an update to the original flight plan is generated and made available for viewing on the user's computing device.

An authorized user can dynamically make changes to a flight plan and communicate the changes across multiple or local systems and subscribers. The changes are synchronized across the multiple or local systems. In order to accomplish this synchronization, messages are automatically generated for each of the systems' and subscriber's communication protocols. The systems and subscribers include the on-board flight management system, mobile devices, local agencies, and ATC. The changes, their status, and associated information can be viewed in real-time. By providing a way to update flight plans from heterogeneous systems, dynamic updates to flight plans from various sources can be accommodated in an efficient manner.

An approved user (pilot, dispatcher, air traffic controller) can view a graphical depiction of an active flight plan in conjunction with multiple flight plans and flight histories. In one embodiment, specific flight history data, past flight plan, or flight history most related to the active flight plan is highlighted or annunciated. Various options are configurable by the user. For example, options can be configured by similar route, speeds, altitude, aircraft type, date range, origin, destination, departure time, arrival time, tail number, pilot's name, or flight number of one or more airline operators. In one embodiment, all data stored in the flight history database are searched, and the flights or flight data most analogous to the active flight plan are identified.

In one implementation, the ATC 89 is compatible with NASA's UTM system to enable safe and efficient low-altitude airspace operations by providing services such as airspace design, corridors, dynamic geofencing, severe weather and wind avoidance, congestion management, terrain avoidance, route planning and re-routing, separation management, sequencing and spacing, and contingency management. UTM could provide to human managers the data to make strategic decisions related to initiation, continuation, and termination of airspace operations to ensure that only authenticated vehicle could operate in the airspace. In its most mature form, the UTM system could be developed using autonomy characteristics that include self-configuration, self-optimization and self-protection. The self-configuration aspect could determine whether the operations should continue given the current and/or predicted wind/weather conditions.

One embodiment is a Portable ATC 89 system, which would move from between geographical areas and support operations such as precision agriculture and disaster relief. The second type of system would be a Persistent ATC 89 system, which would support low-altitude operations and provide continuous coverage for a geographical area. Either system would require persistent communication, navigation, and surveillance (CNS) coverage to track, ensure, and monitor conformance.

Flight plans may be used to document basic information such as departure and arrival points, estimated time en route, various waypoints that the aircraft must traverse enroute, information pertaining to those waypoints, such as actual or estimated altitude and speed of the aircraft at those waypoints, information relating to legs of the flight between those waypoints, and aircraft predicted performance. This type of flight plan may be used to construct a flight trajectory including the various legs of the flight, which are connected to the various waypoints along the route. Flight plans may be used to construct a flight trajectory including the various legs of the flight which are connected to various waypoints along the route. The flight trajectory may include a lateral trajectory defined in the horizontal plane and a vertical trajectory defined in the vertical plane. The flight trajectory may also include the element of time across the horizontal and vertical planes. Flight intent information generally refers to the future flight trajectory of an aircraft expressed as a four-dimensional profile until destination. Flight prediction information also relates to the future flight trajectory, however it is generally limited to a pilot's perspective of information pertinent to the flight. Flight intent information may contain additional flight parameters required by ground systems.

In one aspect, a neural network is trained to generate flight plans from historical data, and such generated plans can be used to approve the flight based on cost factors, among others. In another aspect, a vehicle includes: one or more air vehicles each having a plurality of environmental sensors; a processor with a neural network in at least one vehicle or in at least one communication tower (edge processor) to receive sensor data and follow a pre-approved flight plan based from sensor outputs.

Implementations may include one or more of the following.

Ground systems would use the additional information to perform functions such as the issuance of speed or time clearances. An exemplary flight approval process to the ATC 89 includes:

Start with a direct line between origin and destination and identify waypoints (110)

Look up known obstacles and deviate around obstacles (112)

Look up weather issues and deviate around problematic weather (114)

Look up conflicting filed flight plans and deviate around conflicts with other vehicles (116)

Submit flight plan with origin and destination to approval service (118)

If rejected, provide revised plan and resubmit (120)

During flight, if new obstacles are detected, deviate around new obstacle and update the ATC 89 with new info on the new obstacle (122).

In one aspect, an air control system includes a network of communication towers with ground control modules thereon; a traffic control computer; a plurality of air vehicles each providing flight plans with travel segments in advance to the traffic control computer for approval, wherein the traffic control computer shares approved flight plans to the ground control modules positioned in each travel segment for tracking the vehicle and performing local air traffic control, and wherein each vehicle operates at a reduced power mode based on the approved plan until an unexpected obstacle is encountered, where additional sensors are powered on to help the vehicle navigate. The additional sensors can be on the communication towers to save cost in case of package delivery drones, where cost considerations outweigh the need for absolute perfection in anti collision (such as those for humans).

Implementations may include one or more of the following. The pre-approved flight plan reduces the surprises that may pop up during the flight, requiring fewer resources for continuous autonomous flight navigation which consumes power. Further, the pre-cleared flight plan means that other autonomous vehicles should not interfere with the present vehicle's travel, absent some abnormalities, in which case the autonomous system takes over to avoid the obstacle. Safety is improved. Safety is further enhanced when vehicles travel as a group. Further, fuel efficiency is improved as the lift is improved for all members of the flock traveling together.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed is:

1. A system, comprising:
    a urine receptacle adapted to be worn as underwear on a genital region to remove urine from a person, the receptacle including one or more drain channels and a thermal barrier, the one or more drain channels coupled to one side of the thermal barrier to protect the person during a trip;
    a sealed chamber coupled to the opposite side of the thermal barrier and having a metal evaporator with an alloy therein to generate hydrogen gas from the urine;
    a fuel cell stack configured to receive the generated hydrogen gas from the sealed chamber;
    an energy storage device to store energy from the fuel cell stack;
    a biosensor powered from the energy storage device; and
    a pump coupled to the urine receptacle and the sealed chamber to remove the fluid away from a skin of the person and dispose the urine to the alloy to generate hydrogen gas in the sealed chamber.

2. The system of claim 1, wherein the alloy comprises a nano-structured magnesium or manganese alloy.

3. The system of claim 1, wherein the alloy comprises a nano-structured aluminum alloy.

4. The system of claim 1, wherein the aluminum alloy comprises an anodic matrix including aluminum, an aluminum alloy or an aluminum-based composition; and a cathodic disperse phase comprising a second metal, second alloy or other second metal-based composition selected from the group consisting of: tin (Sn), magnesium (Mg), silicon (Si), bismuth (Bi), lead (Pb), gallium (Ga), indium (In), zinc (Zn), carbon (C), and mixtures and alloys thereof wherein said cathodic disperse phase forms galvanic couples with the anodic matrix and produce hydrogen gas when said galvanic metal microstructure contacts the urine.

5. The system of claim 1, further comprising a power converter coupled to the fuel cell stack to regulate power to a load.

6. The system of claim 1, wherein the energy storage device includes a supercapacitor or a lithium battery.

7. The system of claim 1, wherein the biosensor is configured to detect a glucose level or a cholesterol level.

8. The system of claim 1, wherein the biosensor is positioned in the receptacle to detect a heart rate, a respiratory rate, a temperature, and an activity level from a crotch area.

9. The system of claim 1, wherein heated air is generated as an exothermic reaction to form hydrogen, comprising a garment with channels in the garment to receive urine and channels to provide heated air to warm or dry the garment.

10. The system of claim 1, wherein the biosensor is configured to detect blood pressure level.

11. The system of claim 1, further comprising a camera coupled to one of the drain channels to detect urine color level to determine health condition or a stone particle in the urine.

12. The system of claim 1, wherein the alloy comprises a dissimilar metal in contact with aluminum so as to cause galvanic corrosion.

13. The system of claim 1, wherein the alloy is milled.

14. The system of claim 1, further comprising an optical blood pressure measurement sensor coupled to one of the channels.

15. The system of claim 1, wherein the receptacle comprises a multilayer assembly including a urine drain channel and a heated air tubing.

16. The system of claim 15, comprising a fan coupled to the heated air tubing and a temperature regulator coupled to the fan.

17. The system of claim 1, comprising a processor or a neural network coupled to the energy storage unit to process data from a sensor configured to be coupled to the skin.

18. The system of claim 17, wherein the sensor determines heart rate and blood flow velocity.

19. The system of claim 17, wherein the sensor comprises an optical sensor whose output is calibrated against an approved blood pressure monitor and blood pressure is estimated during operation.

* * * * *